(12) United States Patent
He et al.

(10) Patent No.: US 7,892,773 B2
(45) Date of Patent: Feb. 22, 2011

(54) ANTIBODIES TO HUMAN NK3-RELATED PROSTATE SPECIFIC GENE 1 PROTEINS

(75) Inventors: Wei-Wu He, Columbia, MD (US); Kenneth C. Carter, North Potomac, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 109 days.

(21) Appl. No.: 12/059,797

(22) Filed: Mar. 31, 2008

(65) Prior Publication Data

US 2008/0227127 A1 Sep. 18, 2008

Related U.S. Application Data

(62) Division of application No. 10/614,275, filed on Jul. 8, 2003, now Pat. No. 7,351,694, which is a division of application No. 09/105,470, filed on Jun. 26, 1998, now Pat. No. 6,617,129.

(60) Provisional application No. 60/051,080, filed on Jun. 27, 1997.

(51) Int. Cl.
*G01N 33/53* (2006.01)
*C07K 16/00* (2006.01)
*C07K 7/08* (2006.01)
*C12N 7/00* (2006.01)
*C12N 5/10* (2006.01)
*C12N 15/63* (2006.01)
*C07K 14/00* (2006.01)

(52) U.S. Cl. .............. 435/7.92; 436/501; 530/324; 530/350; 530/387.9; 536/23.1

(58) Field of Classification Search .............. 435/7.92; 436/501; 530/324, 350, 387.8; 536/23.1
See application file for complete search history.

(56) References Cited

U.S. PATENT DOCUMENTS

| 5,194,596 | A | 3/1993 | Tischer et al. |
| 5,350,836 | A | 9/1994 | Kopchick et al. |
| 6,617,129 | B2 | 9/2003 | He et al. |
| 7,351,694 | B2 | 4/2008 | He et al. |
| 2003/0022275 | A1 | 1/2003 | He et al. |
| 2004/0014668 | A1 | 1/2004 | He et al. |

FOREIGN PATENT DOCUMENTS

| WO | WO-95/32214 | 11/1995 |
| WO | WO-97/20942 | 6/1997 |
| WO | WO-99/00498 | 1/1999 |

OTHER PUBLICATIONS

Bova, G.S. et al., "Homozygous Deletion and Frequent Allelic Loss of Chromosome 8p22 Loci in Human Prostrate Cancer," *Cancer Res.*, 53:3869-3873 (1993).

Gehring, W.J. et al., Homeodoma in Proteins, *Annu. Rev. Biochem.*, 63:487-526 (1994).

Ichikawa, T. et al., "Suppression of Metastasis of Rat Prostatic Cancer by Introducing Human Chromosome 8," *Cancer Res.*, 54:2299-2302 (1994).

Kim, Y. and M. Nirenberg, "*Drosophila* NK-homeobox genes," *Proc. Natl. Acad. Sci. USA*, 86:7716-7720 (1989).

Kissinger, C.R. et al., "Crystal Structure of an engrailed Homeodomain-DNA Complex at 2.8 Å Resolution: A Framework for Understanding Homeodomain-DNA Interactions," *Cell*, 63:579-590 (1990).

Konig, J.J. et al., "Cytogenetic characterization of several androgen responsive and unresponsive sublines of the human prostatic carcinoma cell line LNCaP," *Urol. Res.*, 17:79-86 (1989).

Krumlauf, R., "*Hox* Genes in Vertebrate Development," *Cell* 78:191-201 (1994).

Laughon, A. and M.P. Scott, "Sequence of a *Drosophila* segmentation gene: protein structure homology with DNA-binding proteins," *Nature* 310:25-31 (1984).

Lints, T.J. et al., "*Nkx*-2.5: a novel murine homeobox gene expressed in early heart progenitor cells and their myogenic descendants," *Development* 119:419-431 (1993).

Macoska, J.A. et al., "Evidence for Three Tumor Suppressor Gene Loci on Chromosome 8p in Human Prostate Cancer," *Cancer Res.* 55:5390-5395 (1995).

MacGrogan, D. et al., "Loss of Chromosome Arm 8p Loci in Prostate Cancer: Mapping by Quantitative Allelic Imbalance," *Genes, Chromosomes & Cancer* 10:151-159 (1994).

McGinnis, W. and R. Krumlauf, "Homeobox Genes and Axial Patterning," *Cell* 68:283-302 (1992).

Otting, G. et al., "Protein-DNA contacts in the structure of a homeodomain-DNA complex determined by nuclear magnetic resonance spectroscopy in solution," *EMBO J.* 9:3085-3092 (1990).

Price, M. et al., "Regional Expression of the Homeobox Gene *Nkx*-2.2 in the Developing Mammalian Forebrain," *Neuron* 8:241-255 (1992).

Shepherd, J.C.W. et al., "Fly and frog homoeo domains show homologies with yeast mating type regulatory proteins," *Nature* 310:70-71 (1984).

Stein, S. et al., "Checklist: Vertebrate homeobox genes," *Mech. Develop.* 55:91-108 (1996).

Suzuki, H. et al., "Localization of a Tumor Suppressor Gene Associated With Progression of Human Prostate Cancer Within a 1.2 Mb Region of 8p22-p21.3," *Genes, Chromosomes & Cancer* 13:168-174 (1995).

(Continued)

*Primary Examiner*—Lynn Bristol

(57) ABSTRACT

The present invention relates to a novel member of the NK family of homeobox genes. In particular, isolated nucleic acid molecules are provided encoding the human NK-3 prostate specific gene 1 (NKX3.1) protein. NKX3.1 polypeptides are also provided as are vectors, host cells and recombinant methods for producing the same. The invention further relates to screening methods for identifying agonists and antagonists of NKX3.1 activity. Also provided are diagnostic methods for detecting prostate cancer and other cancers and therapeutic methods for prostate cancer and other cancers.

16 Claims, 13 Drawing Sheets

OTHER PUBLICATIONS

Trapman, J. et al., "Loss of Heterozygosity of Chromosome 8 Microsatellite Loci Implicates a Candidate Tumor Suppressor Gene between the Loci *D8S87* and *D8S133* in Human Prostate Cancer," *Cancer Res.* 54:6061-6064 (1994).

Vocke, C.D. et al., "Analysis of 99 Microdissected Prostate Carcinomas Reveals a High Frequency of Allelic Loss on Chromosome 8p12-21," *Cancer Res.* 56:2411-2416 (May 1996).

NCBI Entrez, Genbank Report, Accession No. T72229, Hillier, L. et al. (1995).

NCBI Entrez, Genbank Report, Accession No. T65197, Hillier, L. et al. (1995).

NCBI Entrez, Genbank Report, Accession No. F11981, Auffray, C. et al. (1995).

NCBI Entrez, Genbank Report, Accession No. F13543, Auffray, C. et al. (1995).

NCBI Entrez, Genbank Report, Accession No. R08437, Hillier, L. et al. (1995).

NCBI Entrez, Genbank Report, Accession No. R30778, Hillier, L. et al. (1995).

NCBI Entrez, Genbank Report, Accession No. AA077087, Touchman, J.W. et al. (Oct. 1996).

NCBI Entrez, Genbank Report, Accession No. W50633, Marra, M. et al. (May 1996).

NCBI Entrez, Genbank Report, Accession No. W59023, Marra, M. et al. (Jun. 1996).

NCBI Entrez, Genbank Report, Accession No. W77296, Marra, M. et al. (Jun. 1996).

NCBI Entrez, Genbank Report, Accession No. W99235, Marra, M. et al. (Jul. 1996).

NCBI Entrez, Genbank Report, Accession No. AA019401, Hillier, L. et al. (Aug. 1996).

NCBI Entrez, Genbank Report, Accession No. F14521, Wintero, A.K. et al. (Sep. 1996).

NCBI Entrez, Genbank Report, Accession No. AA082163, Hillier, L. et al. (Oct. 1996).

NCBI Entrez, Genbank Report, Accession No. AA126727, Hillier, L. et al. (Nov. 1996).

NCBI Entrez, Genbank Report, Accession No. AA181926, Hillier, L. et al. (Jan. 1997).

NCBI Entrez, Genbank Report, Accession No. AA187553, Hillier, L. et al. (Jan. 1997).

NCBI Entrez, Genbank Report, Accession No. AA017789, Marra, M. et al. (Jan. 1997).

NCBI Entrez, Genbank Report, Accession No. AA063092, Hillier, L. et al. (Feb. 1997).

NCBI Entrez, Genbank Report, Accession No. AA063646, Hillier, L. et al. (Feb. 1997).

NCBI Entrez, Genbank Report, Accession No. AA062412, Marra, M. et al. (Feb. 1997).

NCBI Entrez, Genbank Report, Accession No. AA154256, Marra, M. et al. (Feb. 1997).

NCBI Entrez, Genbank Report, Accession No. AA145840, Marra, M. et al. (Feb. 1997).

NCBI Entrez, Genbank Report, Accession No. AA238720, Marra, M. et al. (Mar. 1997).

NCBI Entrez, Genbank Report, Accession No. AA268724, Marra, M. et al. (Mar. 1997).

NCBI Entrez, Genbank Report, Accession No. AA305563, Adams, M.D. et al. (Apr. 1997).

NCBI Entrez, Genbank Report, Accession No. AA386139, Adams, M.D. et al. (Apr. 1997).

NCBI Entrez, Genbank Report, Accession No. AA053456, Hillier, L. et al. (May 1997).

NCBI Entrez, Genbank Report, Accession No. AA453083, Hillier, L. et al. (Jun. 1997).

NCBI Entrez, Genbank Report, Accession No. AA472699, Marra, M. et al. (Jun. 1997).

NCBI Entrez, Genbank Report, Accession No. AA522394, Marra, M. et al. (Jul. 1997).

NCBI Entrez, Genbank Report, Accession No. AA494677, Clark, M. et al. (Jun. 1997).

NCBI Entrez, Genbank Report, Accession No. AA542622, Clark, M. et al. (Jul. 1997).

NCBI Entrez, Genbank Report, Accession No. C26874, Yamamoto, K. And Sasaki, T. (Aug. 1997).

NCBI Entrez, Genbank Report, Accession No. AA492170, NCI-CGAP (Aug. 1997).

NCBI Entrez, Genbank Report, Accession No. AA560411, Marra, M. et al. (Aug. 1997).

NCBI Entrez, Genbank Report, Accession No. AA576890, NCI-CGAP (Sep. 1997).

NCBI Entrez, Genbank Report, Accession No. C74515, Sasaki, T. and Yamamoto, K. (Sep. 1997).

NCBI Entrez, Genbank Report, Accession No. AA613299, NCI-CGAP (Oct. 1997).

NCBI Entrez, Genbank Report, Accession No. AA655699, Marra, M. et al. (Nov. 1997).

NCBI Entrez, Genbank Report, Accession No. AA672108, Marra, M. et al. (Nov. 1997).

NCBI Entrez, Genbank Report, Accession No. R90038, Newman, T. et al. (Dec. 1997).

NCBI Entrez, Genbank Report, Accession No. AA173231, Hillier, L. et al. (Mar. 1998).

NCBI Entrez, Genbank Report, Accession No. AA847809, NCI-CGAP (Mar. 1998).

NCBI Entrez, Genbank Report, Accession No. AA892555, Lee, N.H. et al. (Apr. 1998).

NCBI Entrez, Genbank Report, Accession No. AA799346, Lee, N.H. et al. (Apr. 1998).

NCBI Entrez, Genbank Report, Accession No. AA892985, Lee, N.H. et al. (Jun. 1998).

NCBI Entrez, Genbank Report, Accession No. AA782978, NCI-CGAP (Dec. 1998).

NCBI Entrez, Genbank Report, Accession No. AA855030, NCI-CGAP (Jan. 1999).

GenBank Database Document Reader, Accession No. U80669, Prescott, J.L. et al. (Dec. 1996).

Bieberich, C.J. et al., "Prostate-specific and Androgen-dependent Expression of a Novel Homeobox Gene," *J. Biol. Chem.* 271:31779-31782 (Dec. 1996).

He, W.W. et al., "A Novel Human Prostate-Specific, Androgen-Regulated Homeobox Gene (*NKX3.1*) That Maps to 8p21, a Region Frequently Deleted in Prostate Cancer," *Genomics* 43:69-77 (Jul. 1997).

Prescott, J.L. et al., "Isolation and Androgen Regulation of the Human Homeobox cDNA, *NKX3.1*," *The Prostate* 35:71-80 (Apr. 1998).

Sciavolino, P.J. et al., "Tissue-Specific Expression of Murine *Nkx3.1* in the Male Urogenital System," *Develop. Dynamics* 209:127-138 (Apr. 1997).

Voeller, H.J. et al., "Coding Region of *NKX3.1*, a Prostate-Specific Homeobox Gene on 8p21, Is Not Mutated in Human Prostate Cancers," *Cancer Res.* 57:4455-4459 (Oct. 1997).

EMBL Database, Accession No. U73460, Bieberich, C.J. et al., "Mus musculus homeobox-containing protein Nkx-3.1 mRNA, complete cds" (Dec. 1996).

EMBL Database, Accession No. U80669, Prescott, J.S. et al. "Human androgen regulated homeobox protein (NKX3.1) mRNA, complete cds" (Dec. 1996).

Avraham et al., GenBank Accession No. J03224 (Apr. 1991).

Bourdon et al., GenBank Accession No. K02934 (Jun. 1990).

Ohgi et al., *J. Biochem.*, vol. 109, p. 776-785 (1991).

J. Rudinger, Peptide Hormones, Edited by J.A. Parsons, University Park Press, Baltimore, p. 1-7 (Jun. 1976).

Kaye et al., "A single amino acid substitution results in a retinoblastoma protein defective in phosphorylation and oncoprotein bindng," Sep. 1990, *Proc. Natl. Acad. Sci.*, vol. 87, pp. 6922-6926.

Rudinger et al., "Characteristics of the amino acids as components of a peptide hormone sequence," 1976, pp. 1-7.

Hillier et al., Accession No. HO2119, 1995.

Gayle et al., "Identification of Regions in Interleukin-1α Important for Activity," *J. Biol. Chem.*, 268(29):22105-22111 (Oct. 15, 1993).

Zurawski et al., "Definition and spatial location of mouse interleukin-2 residues that interact with its heterotrimeric receptor," *EMBO J.*, 12:5113-5119 (1993).

Loeb et al., "Complete mutagenesis of the HIV-1 protease," *Nature*, 340:397-400 (Aug. 3, 1989).
Inouye et al., "Site-specific mutagenesis of human follistatin," *Biochem. Biophys. Res. Comm.*, 179(1):352-358 (Aug. 30, 1991).
Gloss et al., "Contribution to Catalysis and Stability of the Five Cysteines in *Escherichia coli* Aspartate Aminotransferase. Preparation and Properties of a Cysteine-Free Enzyme," *Biochemistry*, 31:32-39 (1992).
Prescott, J.L. And D.J. Tindall, "Androgen Regulation of a Novel Human Prostate-Specific Homeobox-Containing Gene, PSX-1," *Washington, DC, 1996 International Symposium on Biology of Prostate Growth* (Mar. 28, 1996) (University abstract).
Sciavolino et al., "Role of the Homeobox Gene Psx-1 in Normal Development and Prostate Cancer," *Washington, DC, 1996 International Symposium on Biology of Prostate Growth* (Mar. 28, 1996) (University abstract).
Arps et al., "Cytogenetic Survey of 32 Cancers of the Prostate," *Cancer Genet. Cytogenet.*, 66:93-99 (1993).
Pykett et al., "Loss of Chromosome 8p Sequences in Human Breast Carcinoma Cell Lines," *Cancer Genet. Cytogenet.*, 76:23-28 (1994).
Lundgren et al., "Cytogenetic Analysis of 57 Primary Prostatic Adenocarcinomas," *Genes Chrom. Cancer*, 4:16-24 (1992).
Bergerheim et al., "Deletion Mapping of Chromosomes 8, 10, and 16 in Human Prostatic Carcinoma," *Genes Chrom. Cancer*, 3:215-220 (1991).
Steadman et al., "DNA-binding sequence of the human prostate-specific homeodomain protein NKX3.1," *Nucleic Acids Res.*, 28(12):2389-2395 (2000).
ATCC Search Output (pp. 1-8) (As cited by the Examiner in U.S. Appl. No. 10/614,275), (Sep. 20, 2006).
Benjamin, et al., Development 125:1591-1598 (1998).
Vukicevic, et al., PNAS USA 93:9021-9026 (1996).
Massague, Cell 49:437-438 (1987).
Pilbeam, et al., Bone 14:717-720 (1993).
Skolnick, et al., Trends in Biotech 18:34-39 (2000).
Bork, Genome Research 10:398-400 (2000).
Doerks, et al., Trends in Genetics 14:248-250 (1998).
Smith, et al., Nature Biotechnology 15:1222-1223 (1997).
Brenner, Trends in Genetics 15:132-133 (1999).
Bork, Trends in Genetics 12:425-427 (1996).
Bowie, et al., Science 247:1306-1310 (1990).
Alberts et al., Molecular Biology of the Cell, 3$^{rd}$ edition, 1994, p. 465.
Genes VI (1997) by Benjamin Lewin.
Greenbaum, et al., Genome Biology vol. 4, Issue 9, pp. 117.1-117.8 (2003).
Burgess, et al., Journal of Cell Biology vol. 111:2129-2138 (Nov. 1990).
Lazar, et al., Molecular and Cellular Biology, vol. 8, No. 3, 1247-1252 (Mar. 1988).
Schwartz, et al., Proc. Natl. Acad. Sci. USA, vol. 84:6408-6411 (1987).
Lin, et al., Biochemistry USA, vol. 14:1559-1563 (1975).
Sciavolino, et al., Developmental Dynamics, 209:127-138 (May 1997).
Sequence Alignment Output for aa 124-183 SEQ ID No. 2 and Sciavolino (1 page) (As cited by the Examiner in U.S. Appl. No. 10/614,275), (Sep. 20, 2006).
Bieberich, et al., J. Biol. Chem. 271:31779-31782 (Dec. 13, 1996).
Sequence Alignment Output for aa 124-183 of SEQ ID No. 2 and Bieberich (1 page) (As cited by the Examiner in U.S. Appl. No. 10/614,275), (Sep. 20, 2006).
NCBI Entrez, Genbank Report, Accession No. U91540, He, et al. (Sep. 3, 1997).
NCBI Entrez, Genbank Report, Accession No. AAD11628, Yuan, et al. (Feb. 2, 1999).
NCBI Entrez, Genbank Report, Accession No. AF043244, Koseki, et al. (Sep. 10, 1998).
NCBI Entrez, Genbank Report, Accession No. U67843, Stock, et al. (Oct. 16, 1996).
NCBI Entrez, Genbank Report, Accession No. AF060570, Yuan, et al. (Feb. 2, 1999).
NCBI Entrez, Genbank Report, Accession No. NP_006158, Bowen, et al. (May 16, 2010).
EPO Communication, Application No. 98 931 606.2, 7 pages, Nov. 3, 2004.
WO99/00498 PCT International Search Report, Dec. 4, 1998.
Current Protocols in Molecular Biology, John Wiley and Sons (eds.), N. Y., Supplement 35, p. 2.10.7 and p. A.2.5 (1996).
Declaration of Kenneth Carter and Wei-Wu He, U.S. Appl. No. 09/105,740, 5 pages including Exhibit A, B and C, Submitted Dec. 28, 2000.
NCBI Entrez, Genbank Report, Accession No. NM_006167.3, Bowen, et al. (May 16, 2010).
NCBI Entrez, Genbank Report, Accession No. AAA41837, Avraham, S. et al. (Apr. 1993).
NCBI Entrez, Genbank Report, Accession No. AAA42171, Bourdon, M.A. (Apr. 1993).
NCBI Entrez, Genbank Report, Accession No. AAC34993, Koseki, et al. (Sep. 1998).
NCBI Entrez, Genbank Report, Accession No. AAC52956, Bieberich, et al. (Dec. 1996).
NCBI Entrez, Genbank Report, Accession No. AAC60026, Stock, et al. (Oct. 1996).
NCBI Entrez, Genbank Report; Accession No. U88542, Sciavolino, et al. (May 20, 1997).
NCBI Entrez, Genbank Report, Accession No. AAB68662, He, et al. (Sep. 3, 1997).
NCBI Entrez, Genbank Report, Accession No. AAB38747.1, Prescott, et al. (Dec. 10, 1996).

```
      10                  30                  50
ATGCTCAGGGTTCCGGAGCCGCGGCCCGGGGAGGCGAAAGCGGAGGGGGCCGCGCCGCCG
 M  L  R  V  P  E  P  R  P  G  E  A  K  A  E  G  A  A  P  P
      70                  90                 110
ACCCCGTCCAAGCCGCTCACGTCCTTCCTCATCCAGGACATCCTGCGGGACGGCGCGCAG
 T  P  S  K  P  L  T  S  F  L  I  Q  D  I  L  R  D  G  A  Q
     130                 150                 170
CGGCAAGGCGGCCGCACGAGCAGCCAGAGACAGCGCGACCCGGAGCCGGAGCCAGAGCCA
 R  Q  G  G  R  T  S  S  Q  R  Q  R  D  P  E  P  E  P  E  P
     190                 210                 230
GAGCCAGAGGGAGGACGCAGCCGCGCCCGGGCGCAGAACGACCAGCTGAGCACCGGGCCC
 E  P  E  G  G  R  S  R  A  G  A  Q  N  D  Q  L  S  T  G  P
     250                 270                 290
CGCGCCGCGCCGGAGCAGGCCGAGACGCTGGCAGAGACCGAGCCAGAAAGGCACTTGGGG
 R  A  A  P  E  E  A  E  T  L  A  E  T  E  P  E  R  H  L  G
     310                 330                 350
TCTTATCTGTTGGACTCTGAAAACACTTCAGGCGCCCTTCCAAGGCTTCCCCAAACCCCT
 S  Y  L  L  D  S  E  N  T  S  G  A  L  P  R  L  P  Q  T  P
     370                 390                 410
AAGCAGCCGCAGAAGCGCTCCCGAGCTGCCTTCTCCCACACTCAGGTGATCGAGTTGGAG
 K  Q  P  Q  K  R  S  R  A  A  F  S  H  T  Q  V  I  E  L  E
     430                 450                 470
AGGAAGTTCAGCCATCAGAAGTACCTGTCGGCCCCTGAACGGGCCCACCTGGCCAAGAAC
 R  K  F  S  H  Q  K  Y  L  S  A  P  E  R  A  H  L  A  K  N
     490                 510                 530
CTCAAGCTCACGGAGACCCAAGTGAAGATATGGTTCCAGAACAGACGCTATAAGACTAAG
 L  K  L  T  E  T  Q  V  K  I  W  F  Q  N  R  R  Y  K  T  K
     550                 570                 590
CGAAAGCAGCTCTCCTCGGAGCTGGGAGACTTGGAGAAGCACTCCTCTTTGCCGGCCCTG
 R  K  Q  L  S  S  E  L  G  D  L  E  K  H  S  S  L  P  A  L
     610                 630                 650
AAAGAGGAGGCCTTCTCCCGGGCCTCCCTGGTCTCCGTGTATAACAGCTATCCTTACTAC
 K  E  E  A  F  S  R  A  S  L  V  S  V  Y  N  S  Y  P  Y  Y
     670                 690
CCATACCTGTACTGCGTGGGCAGCTGGAGCCCAGCTTTTGGGTAA
 P  Y  L  Y  C  V  G  S  W  S  P  A  F  G  *
```

FIG.1

```
       10                    30                      50
ATGCTCAGGGTTCCGGAGCCGCGGCCCGGGGAGCCGAAAGCGGAGGGGGCCGCGCCGCCG
 M  L  R  V  P  E  P  R  P  G  E  A  K  A  E  G  A  A  P  P
       70                    90                     110
ACCCCGTCCAAGCCGCTCACGTCCTTCCTCATCCAGGACATCCTGCGGGACGGCGCGCAG
 T  P  S  K  P  L  T  S  F  L  I  Q  D  I  L  R  D  G  A  Q
      130                   150                     170
CGGCAAGGCGGCCGCACGAGCAGCCAGAGACAGTGCGACCCGGAGCCGGAGCCAGAGCCA
 R  Q  G  G  R  T  S  S  Q  R  Q  C  D  P  E  P  E  P  E  P
      190                   210                     230
GAGCCAGAGGGAGGACGCAGCCGCGCCGGGGCGCAGAACGACCAGCTGAGCACCGGGCCC
 E  P  E  G  G  R  S  R  A  G  A  Q  N  D  Q  L  S  T  G  P
      250                   270                     290
CGCGCCGCGCCGGAGGAGGCCGAGACGCTGGCAGAGACCGAGCCAGAAAGGCACTTGGGG
 R  A  A  P  E  E  A  E  T  L  A  E  T  E  P  E  R  H  L  G
      310                   330                     350
TCTTATCTGTTGGACTCTGAAAACACTTCAGGCGCCCTTCCAAGGCTTCCCCAAACCCCT
 S  Y  L  L  D  S  E  N  T  S  G  A  L  P  R  L  P  Q  T  P
      370                   390                     410
AAGCAGCCGCAGAAGCGCTCCCGAGCTGCCTTCTCCCACACTCAGGTGATCGAGTTGGAG
 K  Q  P  Q  K  R  S  R  A  A  F  S  H  T  Q  V  I  E  L  E
      430                   450                     470
AGGAAGTTCAGCCATCAGAAGTACCTGTCGGCCCCTGAACGGGCCCACCTGGCCAAGAAC
 R  K  F  S  H  Q  K  Y  L  S  A  P  E  R  A  H  L  A  K  N
      490                   510                     530
CTCAAGCTCACGGAGACCCAAGTGAAGATATGGTTCCAGAACAGACGCTATAAGACTAAG
 L  K  L  T  E  T  Q  V  K  I  W  F  Q  N  R  R  Y  K  T  K
      550                   570                     590
CGAAAGCAGCTCTCCTCGGAGCTGGGAGACTTGGAGAAGCACTCCTCTTTGCCGGCCCTG
 R  K  Q  L  S  S  E  L  G  D  L  E  K  H  S  S  L  P  A  L
      610                   630                     650
AAAGAGGAGGCCTTCTCCCGGGCCTCCCTGGTCTCCGTGTATAACAGCTATCCTTACTAC
 K  E  E  A  F  S  R  A  S  L  V  S  V  Y  N  S  Y  P  Y  Y
      670                   690
CCATACCTGTACTGCGTGGGCAGCTGGAGCCCAGCTTTTGGGTAA
 P  Y  L  Y  C  V  G  S  W  S  P  A  F  G  *
```

FIG.2

```
               10              20            30
NKX3.1  QKRSRAA-FSHTQVIELERKFSHQKYLSAPERA
NK-3    KKRSRAA-FSHAQVFELERRFAQQRYLSGPERS
NK-2    KKRKRVLFTKAQTYELERRFRQQRYLSAPERE
NK-4    KRKPR-VLFSQAQVLELCRFRLKKYLTGAERE 40            50           60
NKX3.1  HLAKNLKLTETQVKIWFQNRRYKTKRKQ
NK-3    EMAKSLRLTETQVKIWFQNRRYKTKRKQ
NK-2    HLASLIRLTPTQVKIWFQNHRYKTKR-A
NK-4    IIAQKLNLSATQVKIWFQNRRYKSKRGD
```

FIG. 3A

```
Mouse  MLRVAEPREPRVEAGGRSPWAAPPTQSKRLTSFLIQDILRDRAER-CGHSGNP-QHSPDRRDSA
Human  MLRVPEPRPGEAKAEGAAPPTP--SKPLTSFLIQDILRDGAQRQCGRTSSQRQCDPEPEPEPE Mouse  PEPDKAGGRGVAPEDPPSIRHSPAETP--TEPESDAHFETYLLDCEHNPQDLASAPQVTKQP
Human  PEGGRSRAGAQNDQLSTGPRAAPEEAETLAETEPE-R-HLGSYLLDSENTSGALPRLPQTPKQP Mouse  QKRSRAAFSHTQVIELERKFSHQKYLSAPERAHLAKNLKLTETQVKIWFQNRRYKTKRKQ
Human  QKRSRAAFSHTQVIELERKFSHQKYLSAPERAHLAKNLKLTETQVKIWFQNRRYKTKRKQ Mouse  LSEDLGQLEKVSPLSLPALKDDSLPSTSLVSVYITSYPYYPYLYCLGSW-PSFW
Human  LSSELGDLEKHSSL--PALKEEAFSRASLVSVYNSYPYYPYLYCMGSWSPAFG
```

N-TERMINAL REGION 43.1% IDENTITY

HOMEODOMAIN 100% IDENTITY

C-TERMINAL REGION 64.7% IDENTITY

FIG. 3B

```
   1  AATTAACCCT CACTAAAGGG AACAAAAGCT GGAGCTCCAC
  41  CGCCGTGGCG GCCGCGTAAT ACGACTCACT ATAGGGCGAA
  81  GAATTCGGAT CTATCAATCT GCATCCTTCT TTCAGAACCA
 121  TTTGATGTAA GTTTCATAAA TCTTGTGCCT TTGCTCCTAC
 161  TTACTTCAGT GTTTATTTCC TAAAAATATT CTCTTGTACA
 201  CTGACAGTAC AATGTGCAAT TTCAGTAAAT TTAACATTAA
 241  TTCAATACTT CCATCATCGA CCTGACACTG AGACTCATGC
 281  CTGTAGTCCT GGCACTTTGA GAGGCCAAGG CAGGAGGATC
 321  ACTTGAATCC AGGAAATCGA GGCTGCAGTG AGTTATGATG
 361  GCATCACTGC ACTCCAGCCT GGGCGGCAGA GGGAGACCCT
 401  GTCCGTAAAA AACAGAAGAG AAAAGACAAG GAAAGAAAAT
 441  ACTTCCATCA TCTCTGTTCC ACTTTCGTCT GTTGTCACGG
 481  TACCGTCCAG TCCAGTCACA GTACCGGTTG GACCAATCTG
 521  GCTAACCCAT TGTTTAGCCA ATGGGTTACA TGTTAACAGT
 561  TGGTAATCTG CAAAAAGAGT ATGCTGATGT TCTTTTGAAC
 601  TACTTTTTTA AATGCAGTTT TTGCATTTGT CCCTGGCCTA
 641  AAACGCCTTC CATCCGTCTG GAAACTTTTC AAAAGGATGG
 681  TATGTCATGT GTCTGGGGAG GAAGGAAAGT TAACAGGTTA
 721  TTGCGGATAA AGGAACCACC AAAGAAAACC ACTTCTGCAA
 761  CGGGAAAAGG CTTTGGCAAA GGTGTTTTCC TTCTTTCAGC
 801  CTGGGGTCTG GCTGCACCTA CTTGTCATGC CTCTTTGAGG
 841  TCGTAGATAT TGCAGATCTG AGTTTGCACC ATCTCTCCCA
 881  GAGAGAGAGA CCACCCAGAA CTCTCACGGT ACCGCGCGGC
 921  TGCAGTGACT GCGTGCTCAT CCCCTGTAAT TGGCTCTGAC
 961  GGTCCTGAAG AGCTAACTGG ACTGTTTGTC TTGATCGTCC
1001  CATCCCCAGG AGCTTCTCTC TGCTGCGGGT GGGTTGGGGC
1041  AGAGGAGCCC CGCTTTGGGG TGCGCTCCTG GCCTGGGAAA
1081  ACGGCTCAGG GCGGACGGAC GACAGCTGGA GAAGGAGAGG
1121  AAATTGGGGA AGGAGAGGGA ATTGGGGAAG GAGAGGGAAC
1161  TGGGGAAGGA ATCCCCTAGG GAGGAGCGGA GCGGCGGCACT
1201  GCTCAGGGCT CGCAGATCGG CGGGGTCACC TGGGGCTCAG
1241  GGCGGCCAAT CCGCGGCGCG GCCCGTCCCG CGGCCAATGG
1281  GAGGGCGGCG CGGCCCCGCTC CCCTGGGCTA TAAGCGAGCC
1321  GGGAGGCGGA AAGTGAAAGC GGTGCGGGCC GGGCGGGTGC
1361  ATTCAGGCCA AGGCGGGCCC GCCGGGATGC TCAGCGGTTCC
1401  GGAGCCGCGG CCCGGGGAGG CGAAAGCGGA GGGGGCCGCG
1441  CCGCCGACCC CGTCCAAGCC GCTCACGTCC TTCCTCATCC
1481  AGGACATCCT GCGGGACGGC GCCCAGCGGC AAGGCGGCCG
1521  CACGAGCAGC CAGAGACAGC GCGACCCGGA GCCGGAGCCA
1561  GAGCCAGAGC CAGAGGGAGG ACGCAGCCGC GCCGGGGCGC
```

FIG. 5A

```
1601 AGAACGACCA GCTGAGCACC GGGCCCCGCG CCGCGCCGGA
1641 CGAGGCCGAG ACGCTGGCAG AGACCGAGCC AGGTAAGCGG
1681 CGAGGCCGGG GAAGGGCGGC AGCCCAAGGC GGACCCCCAG
1721 AGCTCGGGGT GCAGGGACGC GGGGCTCCGC GGCCACAGGC
1761 AGAGGGACCT TCCCGCCTCC GCAGCCACGC GCGCGCCCCC
1801 GGAATGAACC CTGAGCCCCA GCGTCAGGGC GGCGCAGGAT
1841 TCTGACACCG CAGGATTCGC CCGGTTCCGT GCCTTCCGTT
1881 CCCTGGGGCT CAGAAGCCGG CGCGACTGCA GCGCCACCGC
1921 CTTCCACCGT CCCAGGAGCG GATCCCGCCC CGCGCCACCC
1961 GCGATCGGCC CCAGCCCCCC GGTAGTTATG AGAANTAATA
2001 ATAACTTATT AACAGTGACA AAGCAGCGGT TGACCAGCAA
2041 AGCCTCCGTG TGCTTCCCAA TCCCGTGGGC AGTAAAGCGG
2081 TATATTCGGG GTTCCCTCCG GTGTCCAGGA GAGAGAGTCC
2121 ACTTATTTTC TTTCCTGTCA CTTCTGATGA GGCGACCGAA
2161 CGCCTCGTTT AGCGAAGAGG GAATTAAAGC CCAGAATGAG
2201 CCTGCCTCTG CGTCTCCAGT GGCACAAGCC CTCTCTTGCC
2241 CACCTCGATC CTAACACCGG ATGTCTTTTG GTCTGGCCTT
2281 CCCGGGTATC TTGTTCCACG GCATTTTCCC TGCCTCCCTC
2321 TCCCGCCTCT CCTCAGCACA CAGATCCAGA ATCCCCATAT
2361 AATTCTACTA GACAGTAGGG AGAAAGTTCA ACCACGAAAC
2401 GTCTCTAACT TTGGGTTCTT GATGATTCTT AGCAAATGAA
2441 TGCGTAATAA ACATATTTAC TCACTCTTCA CTCCGGAGAG
2481 CTCCTTAGTC ATGTCAAAAA AGTGAAATGT ATCCACGATG
2521 ACAGTGGGCT GTTTGTTCAC TCACTAAAGA GATAAGCGTG
2561 GATTGAATTC TCTTCTCTTC CCTGCTAACA TGTAACTTTT
2601 GTCTTCCCAT CCCTCCTTCC CCACTCTCCT TTCCAGAAAG
2641 GCACTTGGGG TCTTATCTGT TGGACTCTGA AAACACTTCA
2681 GCCGCCCTTC CAAGGCTTCC CCAAACCCCT AAGCAGCCGC
2721 AGAAGCGCTC CCGAGCTGCC TTCTCCCACA CTCAGGTGAT
2761 CGAGTTGGAG AGGAAGTTCA GCCATCAGAA GTACCTGTCG
2801 GCCCCTGAAC GGGCCCACCT GGCCAAGAAC CTCAAGCTCA
2841 CGGAGACCCA AGTGAAGATA TGGTTCCAGA ACAGACGCTA
2881 TAAGACTAAG CGAAAGCAGC TCTCCTCGGA GCTGGGAGAC
2921 TTGGAGAAGC ACTCCTCTTT GCCCGCCCTG AAAGAGGAGG
2961 CCTTCTCCCG GCCTCCCTG GTCTCCGTGT ATAACAGCTA
3001 TCCTTACTAC CCATACCTGT ACTGCGTGGG CAGCTCGAGC
3041 CCAGCTTTTG GGTAATGCCA GCTCAGGTGA CAACCATTAT
3081 GATCAAAAAC TGCCTTCCCC ACGGTGTCTC TATGAAAAGC
3121 ACAAGGGCCC AAGGTCAGCC AGCAACAGGT CTGCACACCA
3161 AAGCTATTCG AGATTTCCGT CGAAATCTCA GATTCTTCAC
```

FIG.5B

```
3201 TGGTGAGACA ATGAAACAAC AGAGACAGTG AAAGTTTTAA
3241 TACCTAAGTC ATTCCTCCAG TGCATACTGT AGGTCATTTT
3281 TTTTGGTTCT GGCTACCTGT TTGAAGGGGA GAGAGGGAAA
3321 ATCAAGTGGT ATTTTCCAGC ACTTTGTATG ATTTTGGATG
3361 AGTTGTACAC CCAAGGATTC TGTTATGCAA CTCCATCCTC
3401 CTGTGTCACT GAATATCAAC TCTGAAAGAG CAAACCTAAC
3441 AGGAGAAAGG ACAACCAGGA TGAGGATGTC ACCAACTGAA
3481 TTAAACTC
```

1 AAGCTTAAAAAACTGCAAAAAATAGTTTGACTTGTGAGCGGATAACAAT

50 TAAGATGTACCCAATTGTGAGCGGATAACAATTCACACATTAA

94 AGAGGAGAAAATTA CATATG

-35

Operator 1

-10

Operator 2

ANTIBODIES TO HUMAN NK3-RELATED PROSTATE SPECIFIC GENE 1 PROTEINS

This application is a divisional of U.S. application Ser. No. 10/614,275, filed Jul. 8, 2003, (now U.S. Pat. No. 7,351,694, issued Apr. 1, 2008), which is a divisional of U.S. application Ser. No. 09/105,470, filed Jun. 26, 1998 (now U.S. Pat. No. 6,617,129, issued Sept. 9, 2003), which claims benefit under 35 U.S.C. §119(e) of U.S. Provisional Application No. 60/051,080 filed Jun. 27, 1997, each of which is incorporated by reference herein in its entirety.

BACKGROUND OF THE INVENTION

1. Field of the Invention

The present invention relates to a novel member of the NK family of homeobox genes. More specifically, isolated nucleic acid molecules are provided encoding a human NK-3 related prostate specific gene (NKX3.1). NKX3.1 polypeptides are also provided, as are vectors, host cells and recombinant methods for producing the same. The invention further relates to screening methods for identifying agonists and antagonists of NKX3.1 activity. Also provided are diagnostic methods for detecting prostate cancer and other cancers and therapeutic methods for prostate cancer and other cancers.

2. Related Art

The discovery of the homeobox as a conserved DNA sequence element in several *Drosophila* genes responsible for controlling the identity of body segments prompted searches for related genes in other organisms. Homeoboxes have since been discovered in the genome of all metazoan organisms, and several hundred unique homeobox genes have been defined in mice and humans (Gehring, W. J. et al., *Annu. Rev. Biochem.* 63:487-526 (1994); Stein, S. et al., *Mech. Develop.* 55:91-108 (1996)). The homeobox encodes a 60-amino acid domain, termed the homeodomain, that includes a helix-turn-helix motif recognized to be structurally-related to the DNA binding domain of several procaryotic proteins and to the products of the yeast mating type locus (Laughon, A. and Scott, M. P., *Nature* 310:25-31 (1984); Shepherd, J. C. W. et al., *Nature* 310:70-71 (1984)). NMR and crystallographic analyses have confirmed that the homeodomain binds DNA (Kissinger, C. R. et al., *Cell* 63:579-590 (1990); Otting, G. et al., *EMBO J.* 9:3085-3092 (1990)). As predicted by the nature of the phenotypes produced when these genes are mutated, both biochemical and genetic analyses have established that the products of homeobox genes are transcriptional regulatory molecules (McGinnis, W. and Krumlauf, R., *Cell* 68:283-302 (1992)).

The predicted amino acid sequence of the known homeodomains serves as the principal identifier that allows them to be classified into a minimum of 20 distinct groups (Gehring, W. J. et al., *Annu. Rev. Biochem.* 63:487-526 (1994); Stein, S. et al., *Mech. Develop.* 55:91-108 (1996)). The NK family of homeobox genes, first defined by four related *Drosophila* genes, NK-1 through NK-4, can be separated into two distinct classes. NK-2, -3 and -4 are more related to each other than to other homeobox genes, whereas NK-1 is a more distant relative (Kim, Y. and Nirenberg, M., *Proc. Natl. Acad. Sci. USA* 86:7716-7720 (1989)). In mouse, six NK-2-like genes have been identified (Price, M. et al., *Neuron* 8:241-255 (1992); Lints, T. J. et al., *Development* 119:419-431 (1993)). Three of these are more related to NK-2 than the others, which may themselves form a distinct subclass (Lints, T. J. et al., *Development* 119:419-431 (1993)).

The majority of studies aimed at characterizing the functions of homeobox genes have focused principally on their developmental roles (McGinnis, W. and Krumlauf, R., *Cell* 68:283-302 91992); Krumlauf, R., *Cell* 78:191-201 (1994)). A prominent example is the Hox family of genes, whose members have been demonstrated to play critical roles in pattern formation during embryogenesis along the anteroposterior body axis of divergent species (Krumlauf, R., *Cell* 78:191-201 (1994)). Some of the Hox genes, as well as members of other classes of homeobox genes, are also expressed during organogenesis, and a few of these have been reported to be expressed in adult tissues. Surprisingly, the potential roles of homeobox genes in fully differentiated tissues and organs have received comparatively little attention. However, the need for patterning functions to maintain the differentiated states of cell populations and to direct the renewal of specific cell types in adults is axiomatic.

The mechanisms involved in the development and maintenance of prostatic tissue are poorly understood. Although it has been recognized for years that normal development and continued expression in adults of the male secondary sexual phenotype is androgen-dependent, there is relatively little known about the genes on which androgens act or the downstream pathways that lead to development of differentiated tissue. As with prostate development, the fundamental mechanisms underlying prostate cancer also remain obscure, however, androgen regulation and the loss thereof plays a critical role. In both developing and mature prostate, the maintenance of prostate-specific cellular functions requires continuous stimulation by androgens; in prostate cancer tissue, the reciprocal loss of this cellular differentiation, which occurs during progression of the disease, is largely concomitant with a loss of androgen responsiveness by prostatic cells. Identifying the genes involved in either of these largely opposing process, will likely lead to a greater understanding of the fundamental mechanisms involved in both.

Thus far, no genes are known to play a key role in the progressive loss of differentiated phenotype seen in prostate cancer tissue, but various studies indicate the presence of one or more genes on human chromosome 8p that suppress the occurrence and/or progression of the disease. Several investigators have found, based on loss of heterozygosity (LOH) studies, that chromosome bands 8p21 contain loci that are deleted in up to 80% of prostate cancer tissues (Suzuki, et al., *Genes, Chromosomes and Cancer* 13:168-174 (1995), Bova et al., *Cancer Res.* 53:3869-3873 (1993), MacGrogan et al., *Genes, Chromosomes and Cancer* 10:151-159 (1994), Trapman et al., *Cancer Res.* 54:6061-6064 (1994), Macoska, et al., *Cancer Res.* 55:5390-5395 (1995), and Vocke et al., *Cancer Res.* 56:2411-2416 (1996)). In addition, the introduction of human chromosome 8 into the highly metastatic Dunning rat prostate cancer cell line significantly reduces its metastatic potential (Ichikawa et al, *Cancer Res.* 54:2299-2302 (1994)). The loss of 8p during the derivation of subclones from the human prostate cancer line, LNCaP, is correlated with loss of androgen responsiveness (Konig et al., *Urol. Res.* 17:79-86 (1989)).

SUMMARY OF THE INVENTION

A prostate-specific human gene (NKX3.1) which maps to 8p21 and encodes a homeodomain-containing protein related to the *Drosophila* NK gene family was cloned. The gene may play a role in both prostate development and the androgen-driven maintenance of prostatic differentiation in adults. The expression of NKX3.1 in adult humans is restricted to prostate and testes and when assayed in several cell lines, including three lines derived from prostate carcinoma tissue, the gene was expressed solely in the androgen-dependent prostate carcinoma cell line LNCaP. A detailed study of NKX3.1 expression in LNCaP cells has demonstrated that the gene is transcriptionally regulated by androgens. Thus, the new prostate-specific gene NKX3.1 is a candidate for playing a central role in the opposing processes of androgen-driven differentiation of prostatic tissue and loss of that differentiation during the progression of prostate cancer.

Thus, the present invention provides isolated nucleic acid molecules comprising a polynucleotide encoding the human NK-3 related prostate specific gene 1 (NKX3.1) polypeptide having the amino acid sequence shown in FIG. 1 or 2 (SEQ ID NOs:2 or 4) or the amino acid sequence encoded by the cDNA clone deposited as ATCC Deposit Number 209006 on Apr. 28, 1997. The present invention also provides isolated nucleic acid molecules comprising a polynucleotide encoding the human NK-3 related prostate specific gene 1 (HPFCA19) polypeptide having the amino acid sequence encoded by the genomic clone deposited as ATCC Deposit Number 209005 on Apr. 28, 1997.

The present invention also relates to recombinant vectors, which include the isolated nucleic acid molecules of the present invention, and to host cells containing the recombinant vectors, as well as to methods of making such vectors and host cells and for using them for production of NKX3.1 polypeptides or peptides by recombinant techniques.

The invention further provides an isolated NKX3.1 polypeptide having an amino acid sequence encoded by a polynucleotide described herein.

The present invention also provides a screening method for identifying compounds capable of enhancing or inhibiting a cellular response induced by the NKX3.1, which involves contacting cells which express the NKX3.1 with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

The invention provides a diagnostic method useful for diagnosis of prostate cancer and other cancers.

An additional aspect of the invention is related to a method for treating an individual in need of an increased level of NKX3.1 activity in the body comprising administering to such an individual a composition comprising a therapeutically effective amount of an isolated NKX3.1 polypeptide of the invention or an agonist thereof.

BRIEF DESCRIPTION OF THE FIGURES

FIG. 1 shows the nucleotide (SEQ ID NO:1) and deduced amino acid (SEQ ID NO:2) sequences of NKX3.1. Amino acid residues from about 124 to about 183 constitute a homeodomain (underlined region in FIG. 1). The protein has a deduced molecular weight of about 26 kDa.

FIG. 2 shows the nucleotide (SEQ ID NO:3) and deduced amino acid (SEQ ID NO:4) sequences of NKX3.1. Amino acid residues from about 124 to about 183 constitute a homeodomain (underlined region in FIG. 2). The nucleotide sequence differs from that of SEQ ID NO:1 by one nucleotide. The protein has a deduced molecular weight of about 26 kDa and differs from the protein shown in FIG. 1 (SEQ ID NO: 2) by one amino acid.

FIG. 3 (A) shows the regions of similarity between the amino acid sequences of the NKX3.1 protein (SEQ ID NO:2) NK-3, NK-2 and NK-4 (SEQ ID NOs:5-7). (B) shows the regions of similarity between the amino acid sequences of human and mouse NKX3.1 (SEQ ID NOs:9-14).

FIGS. 5A-C show the nucleotide sequence (SEQ ID NO:8) of the genomic clone of NKX3.1 which includes the promoter region. The consensus "CAT" and "TATA" boxes and the first ATG are underlined.

FIG. 6 shows a schematic representation of the pHE4a expression vector (SEQ ID NO:25). The locations of the kanamycin resistance marker gene, the multiple cloning site linker region, the oriC sequence, and the lacIq coding sequence are indicated.

FIG. 7 shows the nucleotide sequence of the regulatory elements of the pHE4a promoter (SEQ ID NO:26). The two lac operator sequences, the Shine-Delgarno sequence (S/D), and the terminal HindIII and NdeI restriction sites (italicized) are indicated.

DETAILED DESCRIPTION

Figure 4A:
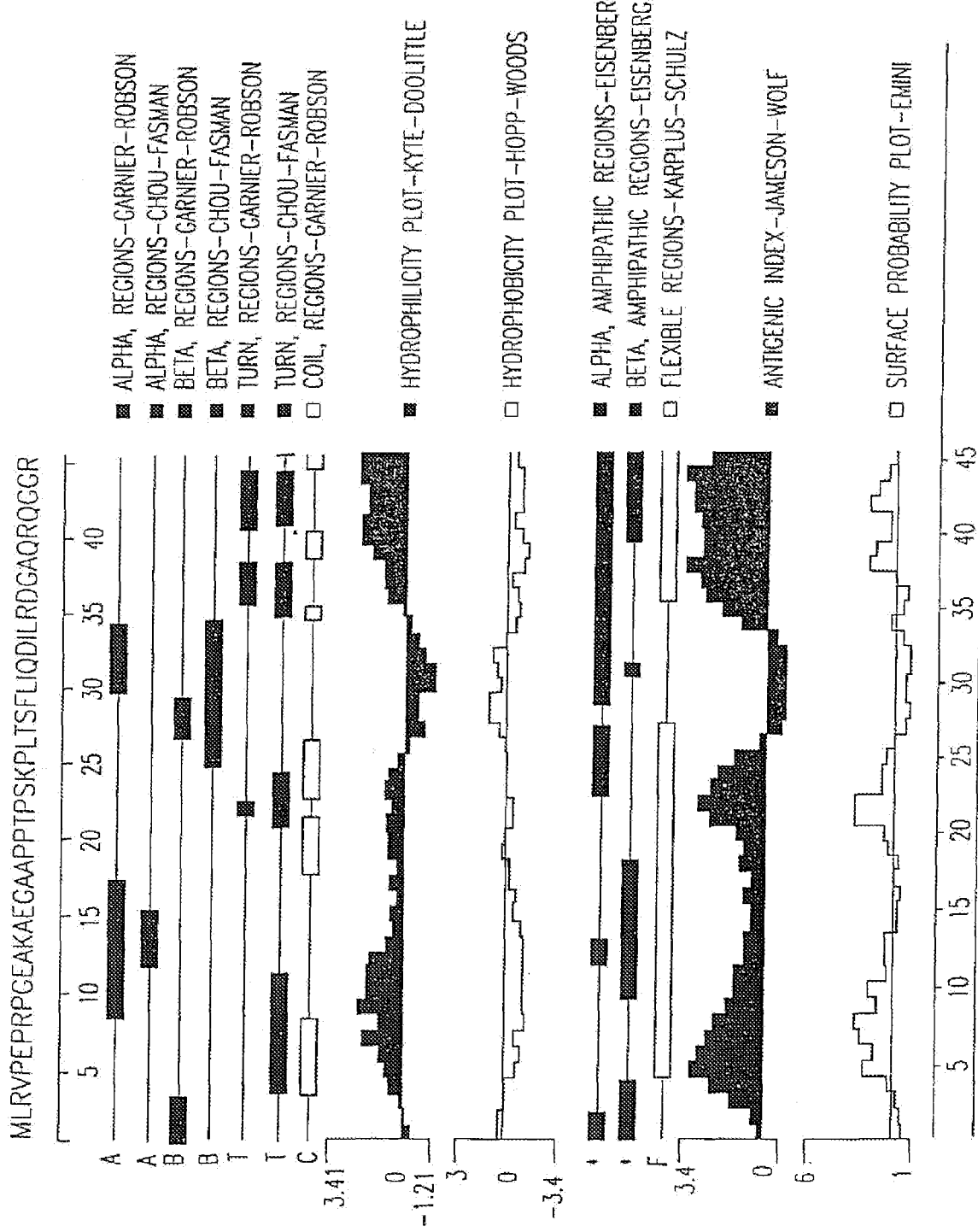
FIGS. 4A-F show an analysis of the NKX3.1 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 1-13, 18-24, 35-89, 103-113, 117-130, 173-185 in FIG. 1 (SEQ ID NO:2 or 4) correspond to the shown highly antigenic regions of the NKX3.1 protein.
Figure 4B:
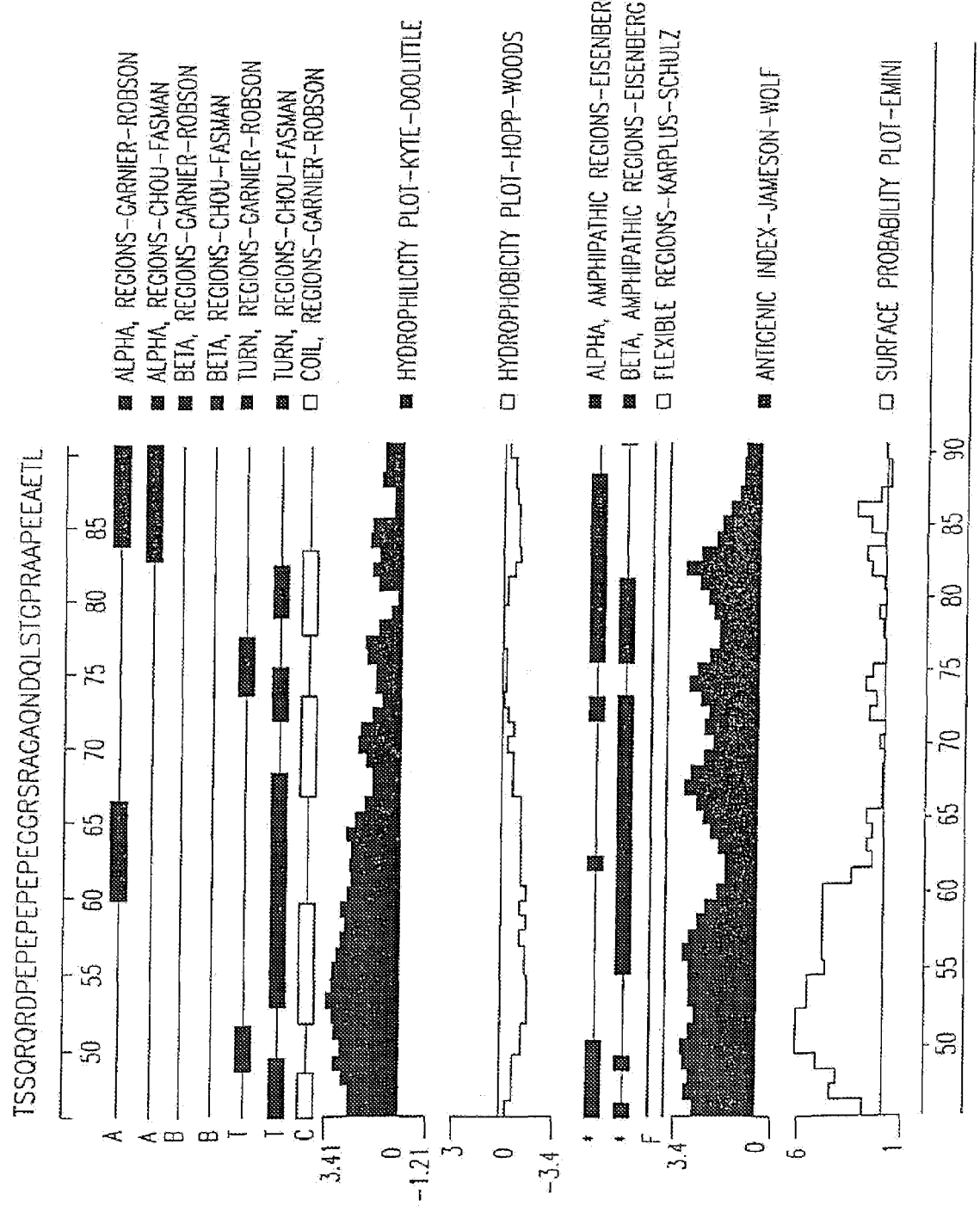
Figure 4C:
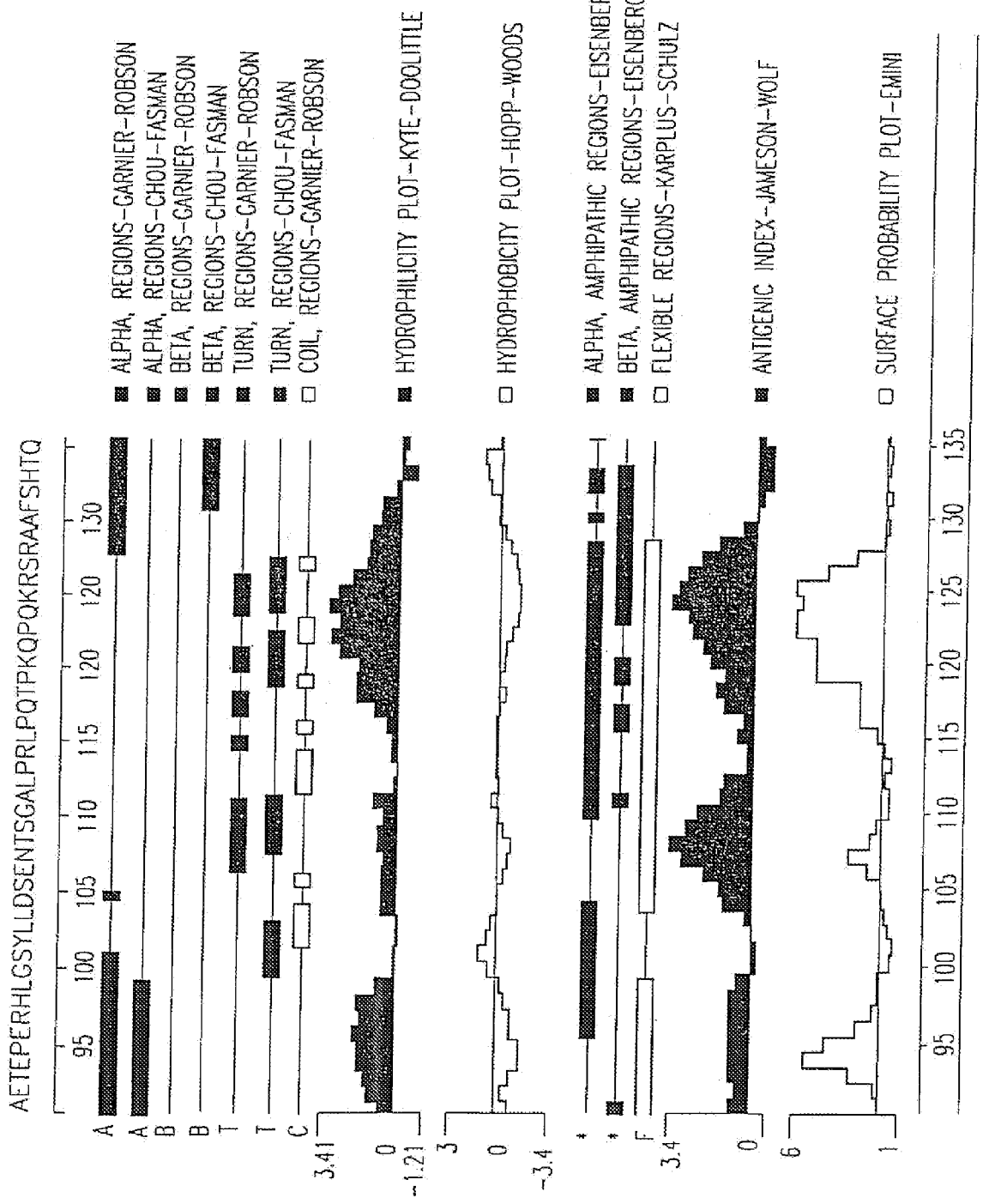
Figure 4D:
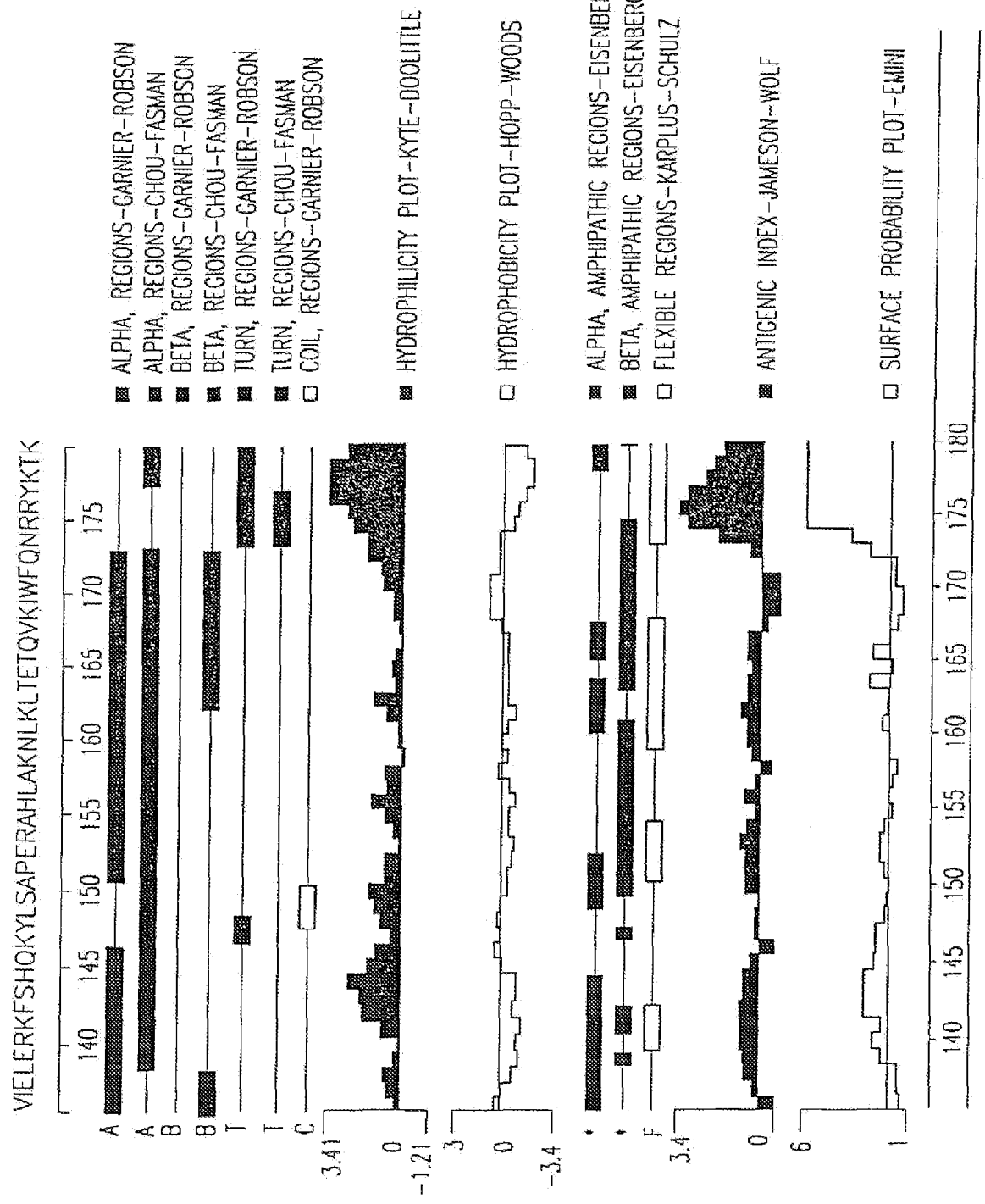
Figure 4E:
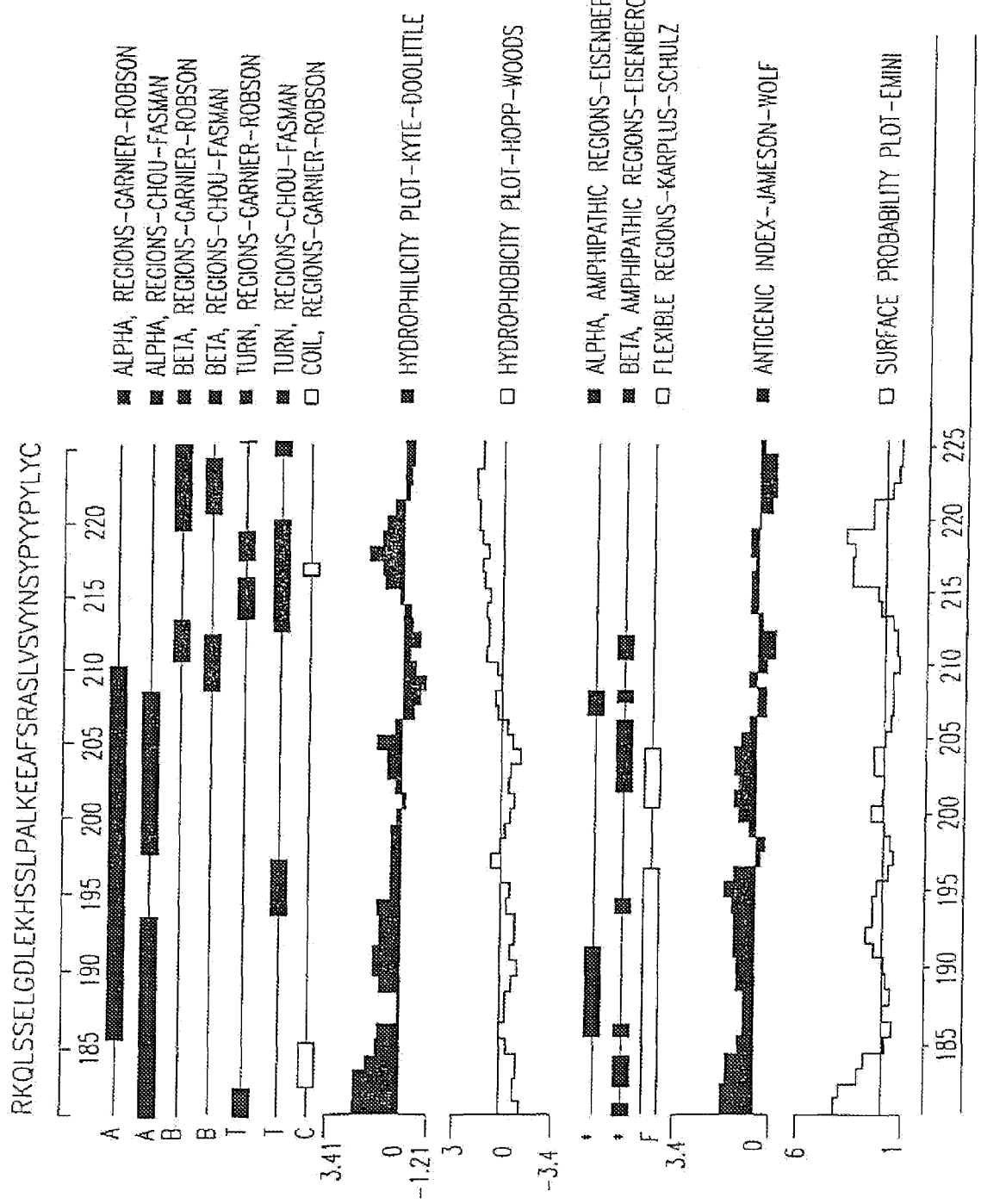
Figure 4F:
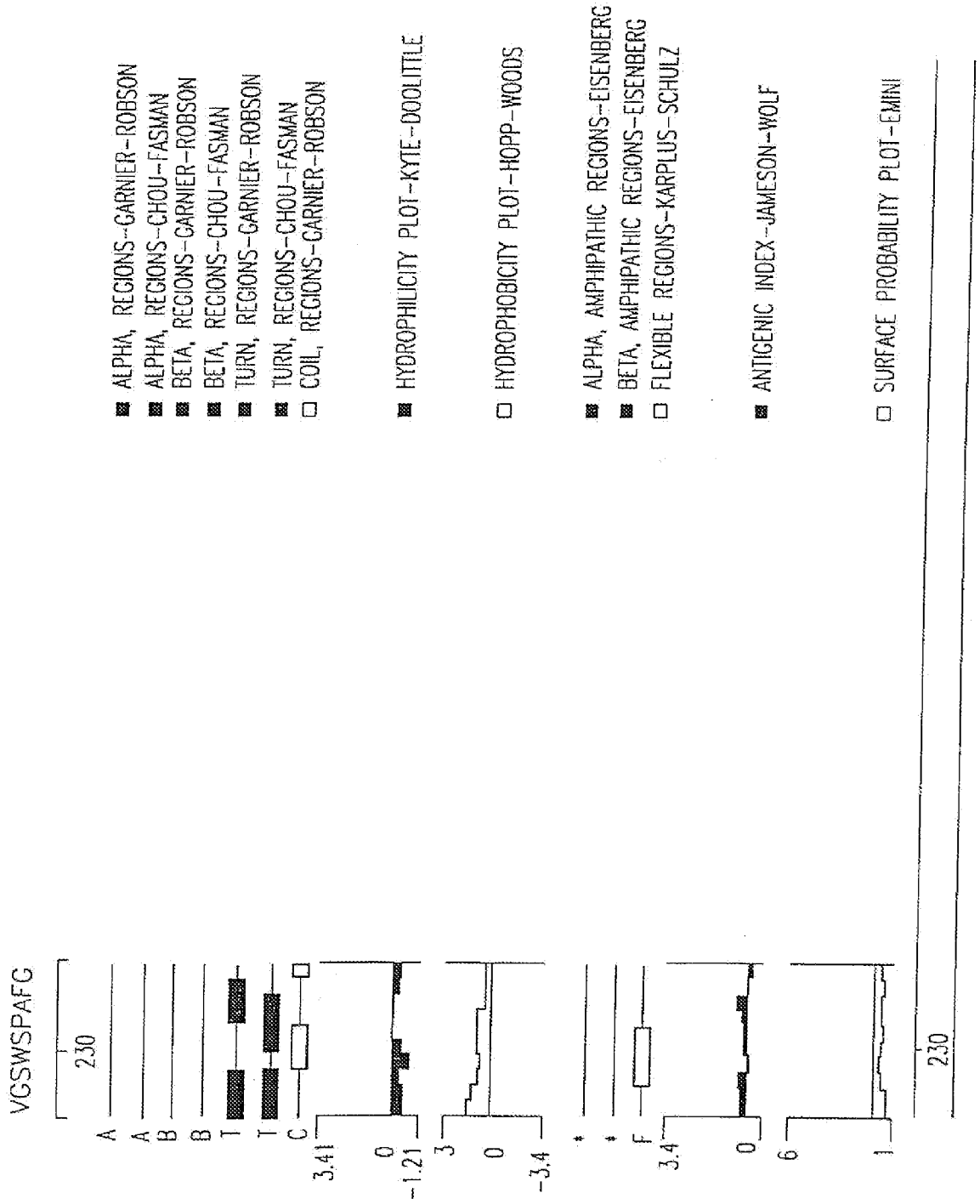

The present invention provides isolated nucleic acid molecules comprising a polynucleotide encoding a NKX3.1 polypeptide having the amino acid sequence shown in FIG. 1 or 2 (SEQ ID NO:2 or SEQ ID NO:4), which was determined by sequencing a cloned cDNA. The NKX3.1 protein of the present invention shares sequence homology with NK-3, NK-2 and NK-4 (FIG. 3) (SEQ ID NOs:5-7). The nucleotide sequence of the genomic clone shown in FIG. 5 (SEQ ID NO:8) was obtained by sequencing the PSX-lambda-1 (NKX3.1) clone, which was deposited on Apr. 28, 1997 at the American Type Culture Collection, Patent Depository, 10801 University Boulevard, Manassas, Va. 20110-2209, and given accession number 209005. The nucleotide sequence shown in FIG. 1 or 2 (SEQ ID NO: 1 or SEQ ID NO:3) was obtained by sequencing the HPFCA19 clone, which was deposited on Apr. 28, 1997 at the American Type Culture Collection Patent Depository, 10801 University Boulevard, Manassas, Va. 20110-2209, and given accession number 209006. The cDNA clone is contained in the pBLUESCRIPT™ SK(-) plasmid (STRATAGENE™, La Jolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIG. 1, 2 or 5, a nucleic acid molecule of the present invention encoding a NKX3.1 polypeptide may be obtained using standard cloning and screening procedures, such as those for cloning cDNAs using mRNA as starting material. Illustrative of the invention, the cDNA clone HPFCA19, which was deposited at the ATCC™ on Apr. 28, 1997, and given accession number 209006, was discovered in cDNA libraries HO169 (HPFC), S0150 (HPIA) and a cDNA library derived from normal prostate tissue. The NKX3.1 nucleotide sequences of FIG. 1 or 2 (SEQ ID NOs: 1 or 3) contain an open reading frame encoding a protein of 234 amino acid residues, with an initiation codon at positions 1-3 of the nucleotide sequence in FIG. 1 or 2 (SEQ ID NOs: 1 or 3), and a deduced molecular weight of about 26 kDa. Within the homeodomain, the NKX3.1 protein shown in FIG. 1 or 2 (SEQ ID NOs:2 or 4) is about 77% identical to NK-3, 63% identical to NK-2 and 53% identical to NK-4 (FIG. 3A). The nucleotide sequence of the genomic clone is shown in FIG. 5 (SEQ ID NO:8).

The murine NKX3.1 gene was isolated from a genomic library by hybridization with a human NKX3.1 probe containing the homeobox sequence. Using the human probe to screen a mouse genomic Pst I library, a single strongly-hybridizing colony was identified. Sequence analysis revealed that the human NKX3.1 protein shown in FIG. 1 (SEQ ID NO:2) and the mouse homolog shown in FIG. 3A are about 43% identical at the N-terminal regions, they have 100% identity in the homeodomain region and are about 67% identical in their C-terminal regions (FIG. 3B).

The newly identified gene of the present invention is most closely related to the *drosophila* NK-3 gene (47/60 aa identity within the homeodomain) and, thus, was named NKX3.1. The longest stretch of complete identity spans aa 40-60 of the homeodomain and is uniquely conserved between NK-3 and NKX3.1. This region includes the area between helices II and III of the consensus homeodomain and the entire length of the helix III, suggesting common subtlety in the structure and function of this portion of the *drosophila* and *mammalian* NK-3-like genes as compared with the other NK family members. The homeodomain of NKX3.1, is identical to the mouse sequence, and shares block of homology with each of the core *Drosophila* NK family members, NK-2, NK-3, and NK-4. The longest stretch of homology is within a strongly conserved block from aa 43-58 of the homeodomain including a tyrosine at position 54, which is a common feature of the NK family of genes and their known vertebrate homologues (Lintz, et al., *Development* 119:419-431 (1994); Gehring et al, *Annu. Rev. Biochem.* 63:487-526 (1994)). NKX3.1 and its mouse counterpart represent the first mammalian homologues of the *drosophila* NK-3 gene.

Typical of most vertebrate homeobox genes, the open reading frame of NKX3.1 is divided between two exons, the second of which contains the entire homeobox region. Each of the analyzed cDNAs terminated approximately 200 Kb beyond the end of the open reading frame and based on the transcription start site predicted from the genomic sequence, this region of the mature mRNA would account for just greater than 1 Kb of processed message. However, Northern analyses indicates that the mature NKX3.1 mRNA is approximately 3.5 Kb long (See, Example 4 below) indicating the presence of a long 3' untranslated region (<3.5 Kb) which is likely encoded within the second exon, as seen with the newly identified mouse gene.

Thus, the present invention provides a nucleotide sequence encoding the NKX3.1 polypeptide having the amino acid sequence encoded by the cDNA clone HPFCA19 deposited as ATCC™ Deposit Number 209006 and as shown in FIG. 1 or 2 (SEQ ID NOs:2 or 4).

As one of ordinary skill would appreciate, due to the possibilities of sequencing errors, the predicted NKX3.1 polypeptide encoded by the deposited clones comprise about 234 amino acids, but may be anywhere in the range of 220 to 250 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in FIG. 1 or 2 (SEQ ID NOs: 1 or 3); DNA molecules comprising the coding sequence for the NKX3.1 protein shown in FIGS. 1, 2 (SEQ ID NOs:2 or 4); and DNA molecules which comprise a sequence substantially different from those described above but which, due to the degeneracy of the genetic code, still encode the NKX3.1 protein. Of course, the genetic code is well known in the art. Thus, it would be routine for one skilled in the art to generate such degenerate variants.

In addition, the invention provides nucleic acid molecules having nucleotide sequences related to extensive portions of SEQ ID NO: 1 or 3 which have been determined from the following related Genbank cDNA clones: AA492170 (SEQ ID NO:27) and AA855030 (SEQ ID NO:28).

In addition, the invention provides nucleic acid molecules having nucleotide sequences related to extensive portions of SEQ ID NO: 1 or 3 which have been determined from the following related cDNA clones: HPIAA91R (SEQ ID NO:29) and HAWAU13R (SEQ ID NO:30).

In another aspect, the invention provides isolated nucleic acid molecules encoding the NKX3.1 polypeptide having an amino acid sequence encoded by the deposited clones contained in the plasmid deposited as ATCC™ Deposit No. 209005 or 209006 on Apr. 28, 1997. Preferably, this nucleic acid molecule will encode the polypeptide encoded by the above-described deposited clones. The invention further provides an isolated nucleic acid molecule having the nucleotide sequence shown in FIG. 1, 2 or 5 (SEQ ID NOs: 1, 3 or 8) or the nucleotide sequence of the NKX3.1 cDNA or genomic sequence contained in the above-described deposited clones, or a nucleic acid molecule having a sequence complementary to one of the above sequences. Such isolated molecules, particularly DNA molecules, are useful as probes for gene mapping, by in situ hybridization with chromosomes, and for detecting expression of the NKX3.1 gene in human tissue, for instance, by Northern blot analysis.

The present invention is further directed to fragments of the isolated nucleic acid molecules described herein. By a fragment of an isolated nucleic acid molecule having the nucleotide sequence of the deposited clones or the nucleotide sequence shown in FIG. 1, 2 or 5 (SEQ ID NOs: 1, 3 or 8) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 75, 100, 125, 150, 175, 200, 225, 250, 300, 325, 350, 375, 400, 425, 450, 475, 500, 525, 550, 575, 600, 625, 650, 675, or 700 nt in length are also useful according to the present invention as are fragments corresponding to most, if not all, of the nucleotide sequence of the deposited clones or as shown in FIG. 1, 2 or 5 (SEQ ID NOs: 1, 3 or 8). By a fragment at least 20 nt in length, for example, is intended fragments which include 20 or more contiguous bases from the nucleotide sequence of the deposited clones or the nucleotide sequence as shown in FIG. 1, 2 or 5 (SEQ ID NOs: 1, 3 or 8).

Preferred nucleic acid fragments of the present invention include nucleic acid molecules encoding epitope-bearing portions of the NKX3.1 protein. In particular, such nucleic acid fragments of the present invention include nucleic acid molecules encoding: a polypeptide comprising amino acid residues from about 1 to about 13 in FIG. 1 or 2 (SEQ ID NOs:2 or 4); a polypeptide comprising amino acid residues from about 18 to about 24 in FIG. 1 or 2 (SEQ ID NOs:2 or 4); a polypeptide comprising amino acid residues from about 35 to about 89 in FIG. 1 or 2 (SEQ ID NOs:2 or 4); a polypeptide comprising amino acid residues from about 103 to about 113 in FIG. 1 or 2 (SEQ ID NOs:2 or 4); a polypeptide comprising amino acid residues from about 117 to about 130 in FIG. 1 or 2 (SEQ ID NOs:2 or 4); and a polypeptide comprising amino acid residues from about 173 to about 185 in FIG. 1 or 2 (SEQ ID NO:2 or 4). The inventors have determined that the above polypeptide fragments are antigenic regions of the NKX3.1 protein. Methods for determining other such epitope-bearing portions of the NKX3.1 protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the deposited clones contained in ATCC™ Deposit 209005 or 209006. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited clones or the nucleotide sequence as shown in FIG. 1, 2 or 5 (SEQ ID NOs: 1, 3 or 8). Of course, a polynucleotide which hybridizes only to a poly A sequence (such as the 3' terminal poly(A) tract of the NKX3.1 nucleotide sequence shown in FIG. 1, 2 or 5 (SEQ ID NOs: 1, 3 or 8), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a NKX3.1 polypeptide may include, but are not limited to those encoding the amino acid sequence of the polypeptide, by itself, the coding sequence for the polypeptide and additional sequences, such as those encoding an amino acid leader or secretory sequence, such as a pre-, or pro- or prepro-protein sequence; the coding sequence of the polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the NKX3.1 fused to Fc at the N- or C-terminus.

The present invention further relates to variants of the nucleic acid molecules of the present invention, which encode portions, analogs or derivatives of the NKX3.1 protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the NKX3.1 protein or portions thereof. Also especially preferred in this regard are conservative substitutions.

Further embodiments of the invention include isolated nucleic acid molecules comprising a polynucleotide having a nucleotide sequence at least 95%, 96%, 97%, 98% or 99% identical to (a) a nucleotide sequence encoding the polypeptide having the amino acid sequence in SEQ ID NOs:2 or 4; (b) a nucleotide sequence encoding the polypeptide having the amino acid sequence in SEQ ID NOs:2 or 4, but lacking the N-terminal methionine; (c) a nucleotide sequence encoding the full-length NKX3.1 polypeptide having the complete amino acid sequence encoded by the clone contained in ATCC™ Deposit No. 209005 or 209006; (d) a nucleotide sequence encoding the homeodomain of the NKX3.1 polypeptide (predicted to constitute amino acid residues 123-153 in FIG. 1 or 2 [SEQ ID NOs: 2 or 4]); or (e) a nucleotide sequence complementary to any of the nucleotide sequences in (a), (b), (c) or (d).

By a polynucleotide having a nucleotide sequence at least, for example, 95% "identical" to a reference nucleotide sequence encoding a NKX3.1 polypeptide is intended that the nucleotide sequence of the polynucleotide is identical to the reference sequence except that the polynucleotide sequence may include up to five point mutations per each 100 nucleotides of the reference nucleotide sequence encoding the NKX3.1 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in FIG. 1, 2 or 5 or to the nucleotides sequence of the deposited clones can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequence shown in FIG. 1, 2 or 5 (SEQ ID NOs: 1, 3 or 8) or to the nucleic acid sequence of the deposited clones, irrespective of whether they encode a polypeptide having NKX3.1 activity. This is because even where a particular nucleic acid molecule does not encode a polypeptide having NKX3.1 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having NKX3.1 activity include, inter alia, (1) isolating the NKX3.1 gene or allelic variants thereof in a cDNA library; (2) in situ hybridization (e.g., "FISH") to metaphase chromosomal spreads to provide precise chromosomal location of the NKX3.1 gene, as described in Verma et al., *Human Chromosomes: A Manual of Basic Techniques*, Pergamon Press, New York (1988); and Northern Blot analysis for detecting NKX3.1 mRNA expression in specific tissues.

Preferred, however, are nucleic acid molecules having sequences at least 95%, 96%, 97%, 98% or 99% identical to the nucleic acid sequence shown in FIG. 1, 2 or 5 (SEQ ID NOs: 1, 3 or 8) or to the nucleic acid sequence of the deposited clones which do, in fact, encode a polypeptide having NKX3.1 protein activity. By "a polypeptide having NKX3.1 activity" is intended polypeptides exhibiting activity similar, but not necessarily identical, to an activity of the NKX3.1 protein of the invention, as measured in a particular biological assay. For example, NKX3.1 protein activity can be measured using the DNA binding experiment set forth in Example 7 below.

Of course, due to the degeneracy of the genetic code, one of ordinary skill in the art will immediately recognize that a large number of the nucleic acid molecules having a sequence at least 95%, 96%, 97%, 98%, or 99% identical to the nucleic acid sequence of the deposited clones or the nucleic acid sequence shown in FIG. 1, 2 or 5 (SEQ ID NOs: 1, 3 or 8) will encode a polypeptide "having NKX3.1 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having NKX3.1 protein activity. This is because the skilled artisan is fully aware of amino acid substitutions that are either less likely or not likely to significantly affect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306-1310 (1990), wherein the authors indicate that proteins are surprisingly tolerant of amino acid substitutions.

Vectors and Host Cells

The present invention also relates to vectors which include the isolated DNA molecules of the present invention, host cells which are genetically engineered with the recombinant vectors, and the production of NKX3.1 polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

In addition to the use of expression vectors in the practice of the present invention, the present invention further includes novel expression vectors comprising operator and promoter elements operatively linked to nucleotide sequences encoding a protein of interest. One example of such a vector is pHE4a which is described in detail below.

Figures 5C, 6:
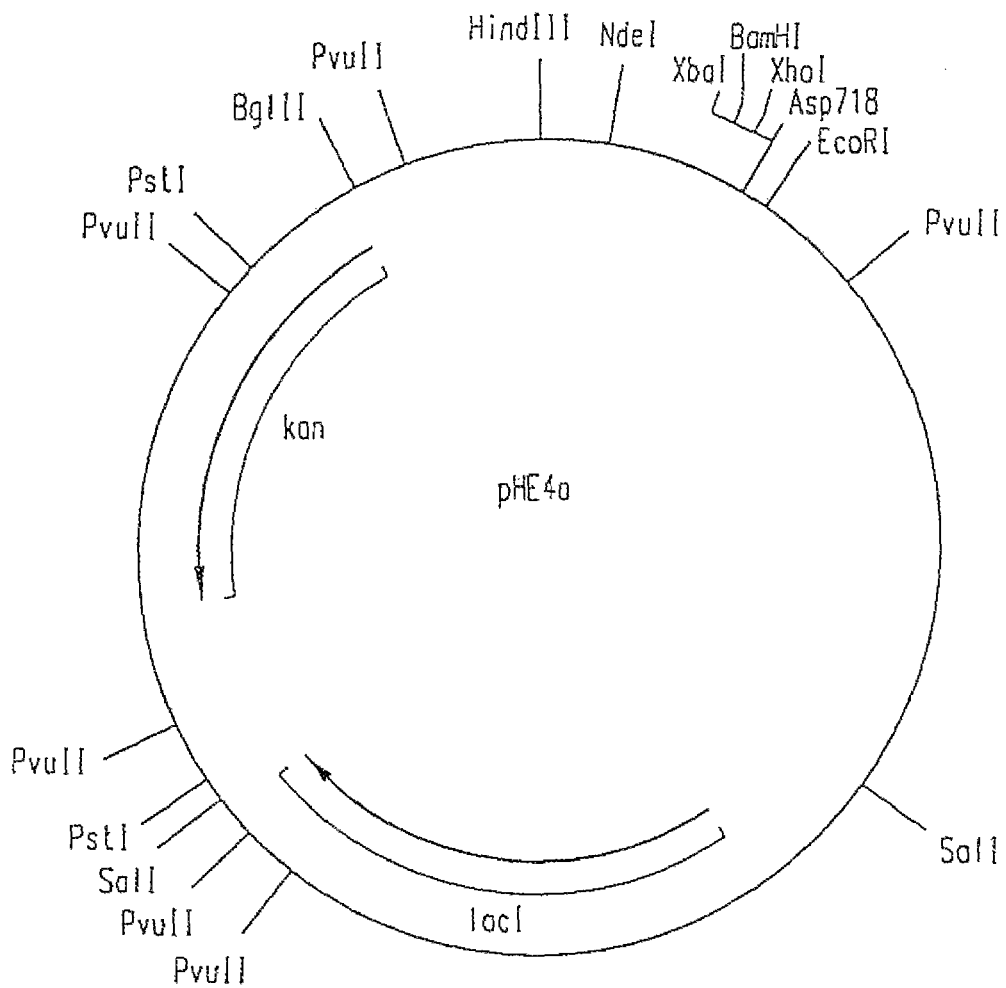

As summarized in FIGS. 6 and 7, components of the pHE4a vector (SEQ ID NO:25) include: 1) a neomycinphosphotransferase gene as a selection marker, 2) an *E. coli* origin of replication, 3) a T5 phage promoter sequence, 4) two lac operator sequences, 5) a Shine-Delgarno sequence, 6) the lactose operon repressor gene (lacIq) and 7) a multiple cloning site linker region. The origin of replication (oriC) is derived from pUC19 (LTI, Gaithersburg, Md.). The promoter sequence and operator sequences were made synthetically. Synthetic production of nucleic acid sequences is well known in the art. CLONTECH™ 95/96 Catalog, pages 215-216, CLONTECH™, 1020 East Meadow Circle, Palo Alto, Calif. 94303. The pHE4a vector was deposited with the ATCC™ on Feb. 25, 1998, and given accession number 209645.

A nucleotide sequence encoding NKX3.1 (SEQ ID Nos: 1 or 3), is operatively linked to the promoter and operator of pHE4a by restricting the vector with NdeI and either XbaI, BamHI, XhoI, or Asp718, and isolating the larger fragment (the multiple cloning site region is about 310 nucleotides) on a gel. The nucleotide sequence encoding NKX3.1 (SEQ ID NO: 1 or 3) having the appropriate restriction sites is generated, for example, according to the PCR protocol described in Example 1, using PCR primers having restriction sites for NdeI (as the 5' primer) and either XbaI, BamHI, XhoI, or Asp718 (as the 3' primer). The PCR insert is gel purified and restricted with compatible enzymes. The insert and vector are ligated according to standard protocols.

As noted above, the pHE4a vector contains a lacIq gene. LacIq is an allele of the lacI gene which confers tight regulation of the lac operator. Amann, E. et al., *Gene* 69:301-315 (1988); Stark, M., *Gene* 51:255-267 (1987). The lacIq gene encodes a repressor protein which binds to lac operator sequences and blocks transcription of down-stream (i.e., 3') sequences. However, the lacIq gene product dissociates from the lac operator in the presence of either lactose or certain lactose analogs, e.g., isopropyl B-D-thiogalactopyranoside (IPTG). NKX3.1 thus is not produced in appreciable quantities in uninduced host cells containing the pHE4a vector. Induction of these host cells by the addition of an agent such as IPTG, however, results in the expression of the NKX3.1 coding sequence.

The promoter/operator sequences of the pHE4a vector (SEQ ID NO:26) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., TEXTBOOK OF BIOCHEMISTRY WITH CLINICAL CORRELATIONS, 4th Edition (1997), pages 802-807.

The pHE4 series of vectors contain all of the components of the pHE4a vector except for the NKX3.1 coding sequence. Features of the pHE4a vectors include optimized synthetic T5 phage promoter, lac operator, and Shine-Delagarno sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4a vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vectors useful for the production of the proteins of the present invention. This aspect of the invention is exemplified by the pHE4a vector (SEQ ID NO:25).

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from STRATAGENE™; and ptrc99a, pKK223-3, pKK233-3, pDR540, pRIT5 available from PHARMACIA™. Among preferred eukaryotic vectors are pWLNEO, pSV2CAT, pOG44, pXT1 and pSG available from STRATAGENE™; and pSVK3, pBPV, pMSG and pSVL available from PHARMACIA™. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, D. Bennett et al., *Journal of Molecular Recognition*, Vol. 8:52-58 (1995) and K. Johanson et al., *The Journal of Biological Chemistry*, Vol. 270, No. 16:9459-9471 (1995).

The NKX3.1 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

NKX3.1 Polypeptides and Fragments

The invention further provides an isolated NKX3.1 polypeptide having the amino acid sequence encoded by the deposited clones, or the amino acid sequence in FIG. 1 or 2 (SEQ ID NOs:2 or 4), or a peptide or polypeptide comprising a portion of the above polypeptides.

It will be recognized in the art that some amino acid sequences of the NKX3.1 polypeptide can be varied without significant effect of the structure or function of the protein. If such differences in sequence are contemplated, it should be remembered that there will be critical areas on the protein which determine activity.

Thus, the invention further includes variations of the NKX3.1 polypeptide which show substantial NKX3.1 polypeptide activity or which include regions of NKX3.1 protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Thus, the fragment, derivative or analog of the polypeptide of FIG. 1 or 2 (SEQ ID NOs:2 or 4), or that encoded by the deposited cDNA or genomic clones, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the NKX3.1 protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of amino acid substitutions for any given NKX3.1 polypeptide will not be more than 50, 40, 30, 20, 10, 5, or 3.

Amino acids in the NKX3.1 protein of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or in vitro, or in vitro proliferative activity. Sites that are critical for NKX3.1-DNA binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

The polypeptides of the present invention are preferably provided in an isolated form, and preferably are substantially purified. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the NKX3.1 polypeptide can be substantially purified by the one-step method described in Smith and Johnson, *Gene* 67:31-40 (1988).

The polypeptides of the present invention include the polypeptide encoded by the deposited cDNA including the leader; a polypeptide comprising amino acids about 1 to about 234 in SEQ ID NOs:2 or 4; a polypeptide comprising amino acids about 2 to about 234 in SEQ ID NOs:2 or 4; a polypeptide comprising amino acids about 2 to about 234 in SEQ ID NOs:2 or 4 but lacking the homeodomain of the polypeptide of SEQ ID NOs:2 or 4 as well as polypeptides which are at least 95% identical, still more preferably at least 96%, 97%, 98% or 99% identical to the polypeptides encoded by the deposited clones, to the polypeptide of FIG. 1 or 2 (SEQ ID NOs:2 or 4), and also include portions of such polypeptides with at least 30 amino acids and more preferably at least 50 amino acids.

By a polypeptide having an amino acid sequence at least, for example, 95% "identical" to a reference amino acid sequence of a NKX3.1 polypeptide is intended that the amino acid sequence of the polypeptide is identical to the reference sequence except that the polypeptide sequence may include up to five amino acid alterations per each 100 amino acids of the reference amino acid of the NKX3.1 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in FIG. 1 or 2 (SEQ ID NOs:2 or 4) or to the amino acid sequence encoded by deposited clones can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767-778 (1984) at 777.

Antigenic epitope-bearing peptides and polypeptides of the invention preferably contain a sequence of at least seven, more preferably at least nine and most preferably between about at least about 15 to about 30 amino acids contained within the amino acid sequence of a polypeptide of the invention.

Non-limiting examples of antigenic polypeptides or peptides that can be used to generate NKX3.1-specific antibodies include: a polypeptide comprising amino acid residues from about 1 to about 13 in SEQ ID NO:2 or SEQ ID NO:4; a polypeptide comprising amino acid residues from about 18 to about 24 in SEQ ID NO:2 or SEQ ID NO:4; a polypeptide comprising amino acid residues from about 35 to about 89 in SEQ ID NO:2 or SEQ ID NO:4; a polypeptide comprising amino acid residues from about 103 to about 113 in SEQ ID NO:2 or SEQ ID NO:4; a polypeptide comprising amino acid residues from about 117 to about 130 in SEQ ID NO:2 or SEQ ID NO:4; and a polypeptide comprising amino acid residues from about 173 to about 185 in SEQ ID NO:2 or SEQ ID NO:4. As indicated above, the inventors have determined that the above polypeptide fragments are antigenic regions of the NKX3.1 protein.

The epitope-bearing peptides and polypeptides of the invention may be produced by any conventional means. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131-5135. This "Simultaneous Multiple Peptide Synthesis (SMPS)" process is further described in U.S. Pat. No. 4,631,211 to Houghten et al. (1986).

As one of skill in the art will appreciate, NKX3.1 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84-86 (1988)). Fusion proteins that have a disulfide-linked dimeric structure due to the IgG part can also be more efficient in binding and neutralizing other molecules than the monomeric NKX3.1 protein or protein fragment alone (Fountoulakis et al., J. Biochem 270:3958-3964 (1995)).

N-Terminal and C-Terminal Deletion Mutants

In one embodiment, the present invention provides polypeptides having one or more residues deleted from the amino terminus of the amino acid sequence of the NKX3 polypeptide depicted in FIG. 1, FIG. 2, or encoded by the cDNA of the deposited clone. Particularly, in one embodiment, N-terminal deletions of the NKX3 polypeptide can be described by the general formula m to 234, where m is any one of the integers from 2 to 233 corresponding to the position of the amino acid residue identified in SEQ ID NO:2 and, preferably, corresponds to one of the N-terminal amino acid residues identified in the N-terminal deletions specified herein. In specific embodiments, N-terminal deletions of the NKX3.1 polypeptide of the invention comprise, or alternatively consist of, amino acid residues: L-2 to G-234; R-3 to G-234; V-4 to G-234; P-5 to G-234; E-6 to G-234; P-7 to G-234; R-8 to G-234; P-9 to G-234; G-10 to G-234; E-11 to G-234; A-12 to G-234; K-13 to G-234; A-14 to G-234; E-15 to G-234; G-16 to G-234; A-17 to G-234; A-18 to G-234; P-19 to G-234; P-20 to G-234; T-21 to G-234; P-22 to G-234; S-23 to G-234; K-24 to G-234; P-25 to G-234; L-26 to G-234; T-27 to G-234; S-28 to G-234; F-29 to G-234; L-30 to G-234; 1-31 to G-234; Q-32 to G-234; D-33 to G-234; 1-34 to G-234; L-35 to G-234; R-36 to G-234; D-37 to G-234; G-38 to G-234; A-39 to G-234; Q-40 to G-234; R-41 to G-234; Q-42 to G-234; G-43 to G-234; G-44 to G-234; R-45 to G-234; T-46 to G-234; S-47 to G-234; S-48 to G-234; Q-49 to G-234; R-50 to G-234; Q-51 to G-234; R-52 to G-234; D-53 to G-234; P-54 to G-234; E-55 to G-234; P-56 to G-234; E-57 to G-234; P-58 to G-234; E-59 to G-234; P-60 to G-234; E-61 to G-234; P-62 to G-234; E-63 to G-234; G-64 to G-234; G-65 to G-234; R-66 to G-234; S-67 to G-234; R-68 to G-234; A-69 to G-234; G-70 to G-234; A-71 to G-234; Q-72 to G-234; N-73 to G-234; D-74 to G-234; Q-75 to G-234; L-76 to G-234; S-77 to G-234; T-78 to G-234; G-79 to G-234; P-80 to G-234; R-81 to G-234; A-82 to G-234; A-83 to G-234; P-84 to G-234; E-85 to G-234; E-86 to G-234; A-87 to G-234; E-88 to G-234; T-89 to G-234; L-90 to G-234; A-91 to G-234; E-92 to G-234; T-93 to G-234; E-94 to G-234; P-95 to G-234; E-96 to G-234; R-97 to G-234; H-98 to G-234; L-99 to G-234; G-100 to G-234; S-101 to G-234; Y-102 to G-234; L-103 to G-234; L-104 to G-234; D-105 to G-234; S-106 to G-234; E-107 to G-234; N-108 to G-234; T-109 to G-234; S-110 to G-234; G-111 to G-234; A-112 to G-234; L-113 to G-234; P-114 to G-234; R-115 to G-234; L-116 to G-234; P-117 to G-234; Q-118 to G-234; T-119 to G-234; P-120 to G-234; K-121 to G-234; Q-122 to G-234; P-123 to G-234; Q-124 to G-234; K-125 to G-234; R-126 to G-234; S-127 to G-234; R-128 to G-234; A-129 to G-234; A-130 to G-234; F-131 to G-234; S-132 to G-234; H-133 to G-234; T-134 to G-234; Q-135 to G-234; V-136 to G-234; 1-137 to G-234; E-138 to G-234; L-139 to G-234; E-140 to G-234; R-141 to G-234; K-142 to G-234; F-143 to G-234; S-144 to G-234; H-145 to G-234; Q-146 to G-234; K-147 to G-234; Y-148 to G-234; L-149 to G-234; S-150 to G-234; A-151 to G-234; P-152 to G-234; E-153 to G-234; R-154 to G-234; A-155 to G-234; H-156 to G-234; L-157 to G-234; A-158 to G-234; K-159 to G-234; N-160 to G-234; L-161 to G-234; K-162 to G-234; L-163 to G-234; T-164 to G-234; E-165 to G-234; T-166 to G-234; Q-167 to G-234; V-168 to G-234; K-169 to G-234; I-170 to G-234; W-171 to G-234; F-172 to G-234; Q-173 to G-234; N-174 to G-234; R-175 to G-234; R-176 to G-234; Y-177 to G-234; K-178 to G-234; T-179 to G-234; K-180 to G-234; R-181 to G-234; K-182 to G-234; Q-183 to G-234; L-184 to G-234; S-185 to G-234; S-186 to G-234; E-187 to G-234; L-188 to G-234; G-189 to G-234; D-190 to G-234; L-191 to G-234; E-192 to G-234; K-193 to G-234; H-194 to G-234; S-195 to G-234; S-196 to G-234; L-197 to G-234; P-198 to G-234; A-199 to G-234; L-200 to G-234; K-201 to G-234; E-202 to G-234; E-203 to G-234; A-204 to G-234; F-205 to G-234; S-206 to G-234; R-207 to G-234; A-208 to G-234; S-209 to G-234; L-210 to G-234; V-211 to G-234; S-212 to G-234; V-213 to G-234; Y-214 to G-234; N-215 to G-234; S-216 to G-234; Y-217 to G-234; P-218 to G-234; Y-219 to G-234; Y-220 to G-234; P-221 to G-234; Y-222 to G-234; L-223 to G-234; Y-224 to G-234; C-225 to G-234; V-226 to G-234; G-227 to G-234; S-228 to G-234; W-229 to G-234; of SEQ ID NO:2. Polynucleotides encoding these polypeptides are also encompassed by the invention.

Further embodiments of the invention are directed to C-terminal deletions of the NKX3 polypeptides of the invention, described by the general formula 1 to n, where n is any one of the integers from 2 to 233 corresponding to the position of amino acid residue identified in SEQ ID NO:2, and preferably corresponds to a residue identified in one of the C-terminal deletions specified herein. In specific embodiments, C-terminal deletions of the NKX3 polypeptides of the invention comprise, or alternatively, consist of, amino acid residues: M-1 to F-233; M-1 to A-232; M-1 to P-231; M-1 to S-230; M-1 to W-229; M-1 to S-228; M-1 to G-227; M-1 to V-226; M-1 to C-225; M-1 to Y-224; M-1 to L-223; M-1 to Y-222; M-1 to P-221; M-1 to Y-220; M-1 to Y-219; M-1 to P-218; M-1 to Y-217; M-1 to S-216; M-1 to N-215; M-1 to Y-214; M-1 to V-213; M-1 to S-212; M-1 to V-211; M-1 to L-210; M-1 to S-209; M-1 to A-208; M-1 to R-207; M-1 to S-206; M-1 to F-205; M-1 to A-204; M-1 to E-203; M-1 to E-202; M-1 to K-201; M-1 to L-200; M-1 to A-199; M-1 to P-198; M-1 to L-197; M-1 to S-196; M-1 to S-195; M-1 to H-194; M-1 to K-193; M-1 to E-192; M-1 to L-191; M-1 to D-190; M-1 to G-189; M-1 to L-188; M-1 to E-187; M-1 to S-186; M-1 to S-185; M-1 to L-184; M-1 to Q-183; M-1 to K-182; M-1 to R-181; M-1 to K-180; M-1 to T-179; M-1 to K-178; M-1 to Y-177; M-1 to R-176; M-1 to R-175; M-1 to N-174; M-1 to Q-173; M-1 to F-172; M-1 to W-171; M-1 to 1-170; M-1 to K-169; M-1 to V-168; M-1 to Q-167; M-1 to T-166; M-1 to E-165; M-1 to T-164; M-1 to L-163; M-1 to K-162; M-1 to L-161; M-1 to N-160; M-1 to K-159; M-1 to A-158; M-1 to L-157; M-1 to H-156; M-1 to A-155; M-1 to R-154; M-1 to E-153; M-1 to P-152; M-1 to A-151; M-1 to S-150; M-1 to L-149; M-1 to Y-148; M-1 to K-147; M-1 to Q-146; M-1 to H-145; M-1 to S-144; M-1 to F-143; M-1 to K-142; M-1 to R-141; M-1 to E-140; M-1 to L-139; M-1 to E-138; M-1 to 1-137; M-1 to V-136; M-1 to Q-135; M-1 to T-134; M-1 to H-133; M-1 to S-132; M-1 to F-131; M-1 to A-130; M-1 to A-129; M-1 to R-128; M-1 to S-127; M-1 to R-126; M-1 to K-125; M-1 to Q-124; M-1 to P-123; M-1 to Q-122; M-1 to K-121; M-1 to P-120; M-1 to T-119; M-1 to Q-118; M-1 to P-117; M-1 to L-116; M-1 to R-115; M-1 to P-114; M-1 to L-113; M-1 to A-112; M-1 to G-111; M-1 to S-110; M-1 to T-109; M-1 to N-108; M-1 to E-107; M-1 to S-106; M-1 to D-105; M-1 to L-104; M-1 to L-103; M-1 to Y-102;

M-1 to S-101; M-1 to G-100; M-1 to L-99; M-1 to H-98; M-1 to R-97; M-1 to E-96; M-1 to P-95; M-1 to E-94; M-1 to T-93; M-1 to E-92; M-1 to A-91; M-1 to L-90; M-1 to T-89; M-1 to E-88; M-1 to A-87; M-1 to E-86; M-1 to E-85; M-1 to P-84; M-1 to A-83; M-1 to A-82; M-1 to R-81; M-1 to P-80; M-1 to G-79; M-1 to T-78; M-1 to S-77; M-1 to L-76; M-1 to Q-75; M-1 to D-74; M-1 to N-73; M-1 to Q-72; M-1 to A-71; M-1 to G-70; M-1 to A-69; M-1 to R-68; M-1 to S-67; M-1 to R-66; M-1 to G-65; M-1 to G-64; M-1 to E-63; M-1 to P-62; M-1 to E-61; M-1 to P-60; M-1 to E-59; M-1 to P-58; M-1 to E-57; M-1 to P-56; M-1 to E-55; M-1 to P-54; M-1 to D-53; M-1 to R-52; M-1 to Q-51; M-1 to R-50; M-1 to Q-49; M-1 to S-48; M-1 to S-47; M-1 to T-46; M-1 to R-45; M-1 to G-44; M-1 to G-43; M-1 to Q-42; M-1 to R-41; M-1 to Q-40; M-1 to A-39; M-1 to G-38; M-1 to D-37; M-1 to R-36; M-1 to L-35; M-1 to 1-34; M-1 to D-33; M-1 to Q-32; M-1 to 1-31; M-1 to L-30; M-1 to F-29; M-1 to S-28; M-1 to T-27; M-1 to L-26; M-1 to P-25; M-1 to K-24; M-1 to S-23; M-1 to P-22; M-1 to T-21; M-1 to P-20; M-1 to P-19; M-1 to A-18; M-1 to A-17; M-1 to G-16; M-1 to E-15; M-1 to A-14; M-1 to K-13; M-1 to A-12; M-1 to E-1; M-1 to G-10; M-1 to P-9; M-1 to R-8; M-1 to P-7; M-1 to E-6; of SEQ ID NO:2. Polynucleotides encoding these polypeptides are also encompassed by the invention.

Further embodiments of the invention are directed to polypeptide fragments comprising, or alternatively, consisting of, amino acid residues described by the general formula III to n, where m and n correspond to any one of the amino acid residues specified above for these symbols, respectively. Polynucleotides encoding these polypeptides are also encompassed by the invention.

NKX3.1 is a Homeoprotein and has a Role in Prostate Function

NKX3.1 and its mouse counterpart represent the first mammalian homologues of the *drosophila* NK-3 gene. The human and mouse proteins are highly homologous, sharing 100 amino acid identity within the homeodomain regions, and are also identical to the *drosophila* gene within the homeodomain helix III and nearly identical within the N-terminal arm, regions which directly contact DNA and define DNA binding specificity in other homeodomains (Gehring et al., *Annu. Rev. Biochem.* 63:487-526 (1994)). Conservation of a tyrosine at position 54, which is conserved in the mouse and human homeodomains, largely defines the unique DNA binding specificity for a "CAAG" binding domain seen with NK family members, as opposed to the "TAAT" core which is preferentially bound by most other the homeodomain proteins (See, reviews in Harvey, *Dev. Biol.* 178:203-216 (1996)). NKX3.1 has NK family-like DNA binding properties in that the protein has binds preferentially to a "CAAG" DNA core, confirming that NKX3.1 similar to other NK family proteins in its DNA binding properties. (See, Example 7). The fact that the presumed DNA binding regions of the human and mouse homeodomain are essentially identical with the same region of *drosophila* NK-3, but not with NK-2 or NK4, may reflect a yet more refined DNA binding specificity that is unique to the NK-3-like homeodomains. Since it appears that NKX3.1 plays a central role in transcriptional regulation of prostate function (See, Examples below), this would provide an obvious mechanism for targeting transcriptional regulation to a unique set of genes as compared to those regulated by other NK-like proteins.

Outside the homeodomain the mouse and human gene sequences are also highly conserved but do not have strong homology with *drosophila* NK-3. Most intriguing is a C-terminal stretch of amino acids that is highly conserved between the mouse and human proteins and is exceptionally rich in tyrosine and serine residues. The fact that these are potential sites for post-transnational phosphorylation and that they are strongly conserved between that mouse and human suggests that they this region may play a role in regulating the function of the protein.

The highly restricted expression of NKX3.1 and the observed androgen regulation (See, Example 5 below), suggests that the gene may play a role in androgen-driven differentiation of prostatic and/or other urogenital tissues. Studies on the mouse NKX3.1 gene indicate that his gene is a strong candidate for playing a central role in maintenance of the prostatic phenotype in adults as well as its establishment during prostate development. NKX3.1 expression in mouse embryos during late gestation coincides with the beginning of prostatic bud formation, and situ localization studies indicate expression at this stage is restricted to epithelial cells within the prostatic buds, urogenital sinus, and testis. (See, Example 9 below) NKX3.1 is also expressed at and different stages and at lower levels in epithelial cell types of several other tissues (See, Examples 9 and 10 below) indicating a potentially broader role in epithelial cell development.

Embryonic expression of NKX3.1 occurs at a time when the prostatic epithelium is not androgen-responsive, indicating that expression of the gene during early development is not androgen dependent. However, later in development there is a surge in NKX3.1 expression which parallels the androgen-driven maturation of adult prostate and seminal vesicle expression (See, Example 9 below). These data are consistent with the fact that human NKX3.1 expression was only found in prostate, testis, and an androgen-dependent prostatic carcinoma line. In addition, a dramatic and immediate loss of expression was seen following castration of adult mice, which is again consistent with the requirement of androgens for NKX3.1 in LNCaP cells (and the absence of expression in prostatic cell lines which have lost androgen responsiveness). Taken together these studies suggest that NKX3.1 and its mouse counterpart, in addition to participating in early urogenital development, may play a role in the androgen-driven maintenance of the differentiated state of prostatic tissue.

Cancer Diagnosis and Prognosis

An intriguing observation is the fact that this new prostate-specific gene, NKX3.1, maps to a chromosomal locus whose loss is implicated in the progression of prostate cancer (See, Example 6, below) and may well be involved in the progression of other forms of cancer. In prostate cancer there is a transition from androgen-dependent growth to androgen-independent growth which is correlated with a loss of prostate tissue phenotype. Although, many studies have addressed this switch to androgen-independence, including several using both the androgen-dependent cell line, LNCaP, and androgen-independent cell lines, PC-3 and DU-145, the underlying mechanisms causing this fundamental transition remain unknown.

Studies have focused on cytogenetic changes and loss of heterozygosity (LOH) studies to identify genetic changes occurring during the progression of prostate cancer and have identified a region spanning 8p21-22 which is thought to contain at least two genes that are lost during the progression of prostate cancer. Detailed deletion mapping has defined a 1.2 Mb commonly deleted within bands 8p22-p21.3, while a second region of common deletion was identified between at 8p21-8p11.22, suggesting that at least 2 tumor suppressor genes are present on chromosome 8p (Suzuki et al., *Genes, Chromosomes, and Cancer* 13:168-174 (1995)). The distal deleted region overlaps with the region commonly deleted in hepatocellular carcinomas, colorectal cancers and non-small cell lung cancers (Emi et al., *Genomics* 15:530-534 (1992); Fujiwara et al., *Genes, Chromosomes, and Cancer* 10:7-14 (1994)). The proximal region, in which the NKX3.1 gene maps, is deleted in up 60-80% prostate cancers (Suzuki, et al., *Genes, Chromosomes and Cancer* 13:168-174 (1995), Bova et al., *Cancer Res.* 53:3869-3873 (1993), MacGrogan et al., *Genes, Chromosomes and Cancer* 10:151-159 (1994), Trapman et al, *Cancer Res.* 54:6061-6064 (1994), Macoska, et al., *Cancer Res.* 55:5390-5395 (1995), and Vocke et al., *Cancer Res.* 56:2411-2416 (1996) and overlaps with a region that is commonly deleted in colorectal cancers (Fujiwara et al., 1993). Recently, Vocke et al. (1996) using the most precise micro-dissection resources available for DNA analysis, found that the loss of markers within 8p12-21, is a very frequent event (62-75%) and is equally likely to occur in early and advanced disease. They interpret these data to indicate that loss at 8p12-21 may be a seminal early event in tumor development, likely prior to loss of androgen-responsiveness and associated loss of the differentiated prostatic phenotype.

Since the NKX3.1 gene appears to be located on 8p21 (see, Example 6 below), the data are consistent with a role for the gene in androgen-driven maintenance of prostate tissue phenotype.

Thus, it is believed that certain tissues in mammals with prostate cancer express significantly decreased levels of the NKX3.1 protein and mRNA encoding the NKX3.1 protein when compared to a corresponding "standard" mammal, i.e., a mammal of the same species not having the cancer. Further, it is believed that decreased levels of the NKX3.1 protein can be detected in certain body fluids (e.g., sera, plasma, urine, and spinal fluid) from mammals with prostate cancer when compared to sera from mammals of the same species not having the cancer. Thus, the invention provides a diagnostic method useful during prostate as well as other cancer diagnosis, which involves assaying the expression level of the gene encoding the NKX3.1 protein in mammalian cells or body fluid and comparing the gene expression level with a standard NKX3.1 gene expression level, whereby a decrease in the gene expression level over the standard is indicative of prostate tumors and other cancers.

Furthermore, the NKX3.1 gene could be used in PCR or other DNA based tests well known to those of skill in the art for mutations and/or loss of this gene during the progression of cancer which could be used diagnostically to monitor the progression and potential medication responsiveness to prostate and other forms of cancer. Similarly, an antibody directed against the NKX3.1 protein or mutant forms of the protein could be used as a marker to monitor the progression and potential medication responsiveness to prostate cancer using immunoassays well known to those of skill the art.

Where a tumor diagnosis has already been made according to conventional methods, the present invention is useful as a prognostic indicator, whereby patients exhibiting decreased NKX3.1 gene expression will experience a worse clinical outcome relative to patients expressing the gene at an enhanced level.

By "assaying the expression level of the gene encoding the NKX3.1 protein" is intended qualitatively or quantitatively measuring or estimating the level of the NKX3.1 protein or the level of the mRNA encoding the NKX3.1 protein in a first biological sample either directly (e.g., by determining or estimating absolute protein level or mRNA level) or relatively (e.g., by comparing to the NKX3.1 protein level or mRNA level in a second biological sample).

Preferably, the NKX3.1 protein level or mRNA level in the first biological sample is measured or estimated and compared to a standard NKX3.1 protein level or mRNA level, the standard being taken from a second biological sample obtained from an individual not having the cancer. As will be appreciated in the art, once a standard NKX3.1 protein level or mRNA level is known, it can be used repeatedly as a standard for comparison.

By "biological sample" is intended any biological sample obtained from an individual, cell line, tissue culture, or other source which contains NKX3.1 protein or mRNA. Biological samples include mammalian body fluids (such as sera, plasma, urine, synovial fluid and spinal fluid) which contain NKX3.1 protein, and ovarian, prostate, heart, placenta, pancreas liver, spleen, lung, breast and umbilical tissue.

The present invention is useful for detecting cancer in mammals. In particular the invention is useful during diagnosis of prostate cancers in mammals. Preferred mammals include monkeys, apes, cats, dogs, cows, pigs, horses, rabbits and humans. Particularly preferred are humans.

Total cellular RNA can be isolated from a biological sample using the single-step guanidinium-thiocyanate-phenol-chloroform method described in Chomczynski and Sacchi, *Anal Biochem.* 162:156-159 (1987). Levels of mRNA encoding the NKX3.1 protein are then assayed using any appropriate method. These include Northern blot analysis (Harada et al., *Cell* 63:303-312 (1990)), S1 nuclease mapping (Fujita et al., *Cell* 49:357-367 (1987)), the polymerase chain reaction (PCR), reverse transcription in combination with the polymerase chain reaction (RT-PCR) (Makino et al., *Technique* 2:295-301 (1990)), and reverse transcription in combination with the ligase chain reaction (RT-LCR).

Assaying NKX3.1 protein levels in a biological sample can occur using antibody-based techniques. For example, NKX3.1 protein expression in tissues can be studied with classical immunohistological methods (Jalkanen, M., et al., *J. Cell. Biol.* 101:976-985 (1985); Jalkanen, M., et al., *J. Cell. Biol.* 105:3087-3096 (1987)).

Other antibody-based methods useful for detecting NKX3.1 protein gene expression include immunoassays, such as the enzyme linked immunosorbent assay (ELISA) and the radioimmunoassay (RIA).

Suitable labels are known in the art and include enzyme labels, such as, Glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

Therapeutics

Since it appears that the loss of NKX3.1 activity plays a role in the loss of differentiated prostatic phenotype in prostate cancer, administration of this protein, or an NKX3.1 agonist, could be used to prevent or treat the loss of differentiated prostate tissue, and thereby prevent or treat prostate cancer. In addition, administration of this protein, or an NKX3.1 agonist, could be used to prevent or treat other forms of cancer.

Modes of Administration

It will be appreciated that conditions caused by a decrease in the standard or normal level of NKX3.1 activity in an individual, can be treated by administration of NKX3.1 protein, or an NKX3.1 agonist. Thus, the invention further provides a method of treating an individual in need of an increased level of NKX3.1 activity comprising administering to such an individual a pharmaceutical composition comprising an effective amount of an isolated NKX3.1 polypeptide of the invention, or an NKX3.1 agonist, effective to increase the NKX3.1 activity level in such an individual.

As a general proposition, the total pharmaceutically effective amount of NKX3.1 polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the NKX3.1 polypeptide is typically administered at a dose rate of about 1 µg/kg/hour to about 50 µg/kg/hour, either by 1-4 injections per day or by continuous subcutaneous infusions, for example, using a mini-pump. An intravenous bag solution may also be employed.

Pharmaceutical compositions containing the NKX3.1 of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Selection of Compounds Capable of Regulating Expression of NKX3.1

As the invention also includes isolated genomic DNA molecules comprising the 5' flanking region of NKX3.1, including the promoter for these splice variants, yet another aspect of the invention is related to a method for identifying compounds capable of enhancing or inhibiting expression of NKX3.1. In order to determine the effect of such compounds, reporter plasmids are constructed by linking a portion of the DNA located 5' to the transcription start site of any of NKX3.1 in front of a reporter gene. Such constructs are then transfected into appropriate cell lines. Compounds that are to be tested for their ability to increase or decrease expression from the NKX3.1 promoter are then administered to the cell bearing the reporter construct, and the effect of each compound on reporter gene expression is determined by comparing that level of expression to the expression level in a control cell bearing the reporter construct, where the test compound has not been administered to the control cell.

The DNA sequence of the 5' flanking region of the NKX3.1 gene is shown in FIG. 5 (SEQ ID NO:8) (ATCC™ No. 209005). Of course, since the nucleotide sequence is known, routine methods are available for producing such nucleic acid molecules synthetically (see, for example, *Synthesis and Application of DNA and RNA*, S. A. Narang, ed., 1987, Academic Press, San Diego, Calif.). Alternatively, such isolated nucleic acid molecules of the present invention can be generated as follows. The NKX3.1 gene promoter region is obtained by amplification using the polymerase chain reaction (PCR). The amplified fragment is then inserted into an appropriate plasmid (such as, for example, pCAT™ (PROMEGA™, Madison, Wis.)). Nested deletion plasmids are then generated using the commercially available "Erase-a-Base" System (PROMEGA™, Madison, Wis.) as described in Henikoff, *Gene* 28:351-359 (1984)). Thus, only routine experimentation would be required to generate any of the isolated nucleic acid molecules of the present invention which are capable of enhancing or inhibiting gene expression.

The nucleic acid molecules of the present invention can include the NKX3.1 promoter and cis-acting enhancer and/or silencer elements capable of affecting gene transcription. For simplicity, these isolated nucleic acid molecules of the present invention are referred to below as "NKX3.1 transcriptional regulatory elements" or "transcriptional elements." As indicated, to determine the effect of a transcriptional element of the present invention on gene expression, nested deletion reporter plasmids can be generated containing a transcriptional element of the present invention linked in front of the chloramphenicol acetyltransferase (CAT) reporter gene. Such recombinant DNA molecules of the present invention actually generated by the inventors include transcriptional elements inserted, in both orientations, into the XbaI site of pBLCAT2 vector (Luckow, B., Schütz, G., *Nucleic Acids Res.* 15:5490 (1987)).

By the invention, a recombinant DNA molecule containing a transcriptional element of the present invention is used to transiently transfect an appropriate cell line such as, for example, human choriocarcinoma cell lines (JEG-3 and JAR), the human prostate carcinoma cell line PC-3, or the monkey kidney cell line CV-1, all of which are available form the American Type Culture Collection. In addition to using the CAT system for reporter gene analyses, the hGH transient expression system can also be used (Selden et al., *Mol. Cell. Biol.* 6:3173-3179 (1986)) or other systems that are based on the expression of β-galactosidase (An et al., *Mol. Cell. Biol.* 2:1628-1632 (1982)) and xanthine-guanine phosphoribosyl transferase (Chu et al., *Nucleic Acids Res.* 13:2921-2930 (1985)).

A transcriptional element of the present invention may be inserted into an appropriate vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., et al., infra, and are well known in the art. Clones containing a transcriptional element of the present invention may be identified by any means which specifically selects for a NKX3.1 enhancer or silencer region DNA such as, for example by hybridization with an appropriate nucleic acid probe(s) containing a sequence complementary to all or part of the transcriptional element. Oligonucleotide probes specific for a transcriptional element of the present invention can be designed simply by reference to the sequences disclosed in FIG. 5. Techniques for nucleic acid hybridization and clone identification are disclosed by Maniatis, T., et al., (In: *Molecular Cloning, A Laboratory Manual*, Cold Spring Harbor Laboratories, Cold Spring Harbor, N.Y. (1982)), and by Hames, B. D., et al., (In: *Nucleic Acid Hybridization, A Practical Approach*, IRL Press, Washington, D.C. (1985)). To facilitate the detection of the desired clone containing a transcriptional element of the present invention, the above-described nucleic acid probe may be labeled with a detectable group. Such detectable groups can be any material having a detectable physical or chemical property. Such materials have been well-developed in the field of nucleic acid hybridization and in general most any label useful in such methods can be applied to the present invention. Particularly useful are radioactive labels, such as $^{32}$P, $^3$H, $^{14}$C, $^{35}$S, $^{125}$I, or the like. Any radioactive label may be employed which provides for an adequate signal and has a sufficient half-life. The oligonucleotide may be radioactively labeled, for example, by "nick-translation" by well-known means, as described in, for example, Rigby, P. J. W., et al., *J. Mol. Biol.* 113:237 (1977) and by T4 DNA polymerase replacement synthesis as described in, for example, Deen, K. C., et al., *Anal. Biochem.* 135:456 (1983). Alternatively, polynucleotides are also useful as nucleic acid hybridization probes when labeled with a non-radioactive marker such as biotin, an enzyme or a fluorescent group. See, for example, Leary, J. J., et al., *Proc. Natl. Acad. Sci. USA* 80:4045 (1983); Renz, M., et al., *Nucl. Acids Res.* 12:3435 (1984); and Renz, M., *EMBO J.* 6:817 (1983).

As used herein, "heterologous protein" is intended to refer to a peptide sequence that is heterologous to the transcriptional regulatory elements of the invention. A skilled artisan will recognize that, if desired, the teaching herein will also apply to the expression of genetic sequences encoding the NKX3.1 protein, or splice variants thereof, by such transcriptional regulatory elements. The reporter genes for use in the screening assay described below can code for either the NKX3.1 protein, or splice variants thereof, or a heterologous protein. Alternatively, detection of reporter gene expression can be at the mRNA level, such as, for example, detection of NKX3.1 mRNA.

To express a reporter gene under the control of the transcriptional regulatory elements of the invention, the gene must be "operably-linked" to the regulatory element. An operable linkage is a linkage in which a desired sequence is connected to a transcriptional or translational regulatory sequence (or sequences) in such a way as to place expression (or operation) of the desired sequence under the influence or control of the regulatory sequence.

Two DNA sequences (such as a reporter gene and a promoter region sequence linked to the 5' end of the reporter gene) are said to be operably linked if induction of promoter function results in the transcription of the reporter gene and if the nature of the linkage between the two DNA sequences does not (1) result in the introduction of a frame-shift mutation (if reporter protein activity is necessary for detection of reporter gene expression), (2) interfere with the ability of the expression regulatory sequences to direct reporter gene expression, or (3) interfere with the ability of reporter gene to be transcribed by the promoter region sequence. Thus, a promoter would be operably linked to a DNA sequence if the promoter were capable of affecting transcription of that DNA sequence.

In a similar manner, a transcriptional regulatory element of the present invention that enhances or represses gene expression may be operably-linked to such a promoter. Exact placement of the element in the nucleotide chain is not critical as long as the element is located at a position from which the desired effects on the operably linked promoter may be revealed. A nucleic acid molecule, such as DNA, is said to be "capable of expressing" a polypeptide if it contains expression control sequences which contain transcriptional regulatory information and such sequences are operably linked to the nucleotide sequence which encodes the polypeptide. For the complete control of gene expression, all transcriptional and translational regulatory elements (or signals) that are operably linked to a heterologous gene should be recognizable by the appropriate host. By "recognizable" in a host is meant that such signals are functional in such host.

The NKX3.1 transcriptional regulatory elements of the present invention, obtained through the methods described above, and preferably in a double-stranded form, may be operably linked to a heterologous gene (such as a reporter gene), preferably in an expression vector, and introduced into a host cell, preferably a eukaryotic cell, to assay reporter gene expression. Preferred eukaryotic cells include prostate cell lines, choriocarcinoma cell lines, breast cancer cell lines, prostate carcinoma cell lines and kidney cell lines.

As is widely known, translation of eukaryotic mRNA is initiated at the codon that encodes the first methionine. For this reason, it is preferable to ensure that the linkage between a eukaryotic promoter and a reporter gene does not contain any intervening codons that are capable of encoding a methionine. The presence of such codons results either in a formation of a fusion protein (if the AUG codon is in the same reading frame as the DNA encoding the heterologous protein) or a frame-shift mutation (if the AUG codon is not in the same reading frame as the reporter gene).

If desired, a fusion product of a reporter protein may be constructed. For example, the sequence coding for the reporter protein may be linked to a signal sequence which will allow secretion of the protein from, or the compartmentalization of the protein in, a particular host. Such signal sequences may be designed with or without specific protease sites such that the signal peptide sequence is amenable to subsequent removal. Alternatively, the native signal sequence for this protein may be used.

The transcriptional regulatory elements of the invention can be selected to allow for repression or activation, so that expression of the operably linked reporter genes can be modulated. Translational signals are not necessary when it is desired to express antisense RNA sequences or to assay reporter gene expression via mRNA detection.

If desired, the non-transcribed and/or non-translated regions 3' to the reporter gene can be obtained by the above-described cloning methods. The 3'-non-transcribed region may be retained for its transcriptional termination regulatory sequence elements; the 3'-non-translated region may be retained for its translational termination regulatory sequence elements, or for those elements that direct polyadenylation in eukaryotic cells. Where the native expression control sequences signals do not function satisfactorily host cell, then sequences functional in the host cell may be substituted.

To transform a mammalian cell with the DNA constructs of the invention many vector systems are available, depending upon whether it is desired to insert the reporter gene product into the host cell chromosomal DNA, or to allow it to exist in an extrachromosomal form. If the reporter gene and an operably linked promoter are introduced into a recipient eukaryotic cell as a non-replicating DNA (or RNA) molecule, which may either be a linear molecule or, more preferably, a closed covalent circular molecule that is incapable of autonomous replication, reporter gene expression may occur through the transient expression of the introduced sequence.

Genetically stable transformants may be constructed with vector systems, or transformation systems, whereby the reporter gene is integrated into the host chromosome. Such integration may occur de novo within the cell or, in a most preferred embodiment, be assisted by transformation with a vector that functionally inserts itself into the host chromosome. Vectors capable of chromosomal insertion include, for example, retroviral vectors, transposons or other DNA elements which promote integration of DNA sequences in chromosomes, especially DNA sequence homologous to a desired chromosomal insertion site.

Cells that have stably integrated the introduced DNA into their chromosomes are selected by also introducing one or more markers that allow for selection of host cells which that the desired sequence. For example, the marker may provide biocide resistance, e.g., resistance to antibiotics, or heavy metals, such as copper, or the like. The selectable marker gene can either be directly linked to the reporter gene, or introduced into the same cell by co-transfection. In another embodiment, the introduced sequence is incorporated into a plasmid or viral vector capable of autonomous replication in the recipient host. Any of a wide variety of vectors may be employed for this purpose, as outlined below. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include those derived from the bovine papilloma virus, vaccinia virus, and SV40. Such plasmids are well known in the art and are commonly or commercially available. For example, mammalian expression vector systems in which it is possible to cotransfect with a helper virus to amplify plasmid copy number, and, integrate the plasmid into the chromosomes of host cells have been described (Perkins, A. S. et al., *Mol. Cell Biol.* 3:1123 (1983); CLONTECH™, Palo Alto, Calif.). Particularly preferred are vectors derived from pCAT-Basic, pCAT-Enhancer and pCAT-Promoter vectors ( PROMEGA™, Madison, Wis.).

Once the vector or DNA sequence containing the construct(s) is prepared for expression, the DNA construct(s) is introduced into an appropriate host cell by any of a variety of suitable means, including transfection, electroporation or delivery by liposomes. DEAE dextran, calcium phosphate, and preferably, the transfection reagent DOTAP, may be useful in the transfection protocol.

After the introduction of the vector in vitro, recipient cells are grown in a selective medium, that is, medium that selects for the growth of vector-containing cells. Expression of the reporter gene results in the production mRNA and, if desired, reporter protein. According to the invention, this expression can take place in a continuous manner in the transformed cells, or in a controlled manner. If desired, in vitro culture, the reporter protein is isolated and purified in accordance with conventional conditions, such as extraction, precipitation, chromatography, affinity chromatography, electrophoresis, or the like. Alternatively, levels of reporter protein expression can be assayed according to conventional protein assays, such as, for example, the CAT expression system.

The NKX3.1 transcriptional regulatory elements of the present invention (i.e., the NKX3.1 promoter, as well as isolated nucleic acid molecules capable of enhancing and/or repressing gene expression) are useful for screening drugs, ligands and/or other trans-acting agents to determine which are capable of affecting expression of NKX3.1 or any splice variant thereof. By the invention, trans-acting factors can be identified by their ability to up-regulate or down-regulate NKX3.1 expression. As used herein, by "NKX3.1 trans-acting agent" is intended a drug, ligand, or other compound capable interacting, either directly or indirectly, with a NKX3.1 transcriptional regulatory element of the present invention to enhance or repress gene expression. Such NKX3.1 trans-acting elements which interact directly with a transcriptional regulatory element of the present invention include those, which, for example, bind directly to the element and either enhance or repress gene expression. NKX3.1 trans-acting agents which interact indirectly with a transcriptional regulatory element of the present invention include those which, for example, bind to and induce activity of a second trans-acting agent (e.g., a receptor molecule) which itself then, either alone or complexed to the first trans-acting agent, binds to the element and either enhances or represses gene expression. One type of trans-acting agent is a triplex-forming oligonucleotide. Administration of a suitable oligonucleotide will result in the formation of a triple helix between the oligonucleotide and the NKX3.1 promoter, which will inhibit transcription from that promoter (Ebbinghaus, S. W. et al., *Gene Therapy* 3: 287-297 (1996); Roy, C., *Eur. J. Biochem.* 220: 493-503 (1994)). Because the genomic sequence of the region 5' of the NKX3.1 gene is given herein (See FIG. 5 and SEQ ID NO:8), one of ordinary skill in the art will readily be able to design suitable oligonucleotides (also called "anti-sense" oligonucleotides) which can inhibit expression from the NKX3.1 promoter. One region which is especially useful for anti-sense design is the 5' untranslated region (*J. Biol. Chem.* 266: 18162-18171 (1991)), which of course is not included in a cDNA, but is included in the genomic sequence disclosed herein.

Thus, in one aspect, the invention provides a screening assay for determining whether any given compound is capable of up-regulating or down-regulating expression from the NKX3.1 promoter, leading to an increase or decrease of NKX3.1 production.

The screening assay involves (1) providing a host cell transfected with a recombinant nucleic acid molecule containing a NKX3.1 transcriptional regulatory element of the present invention and a reporter gene, wherein the transcriptional element is operably linked to the reporter gene; (2) administering a candidate NKX3.1 trans-acting agent to the transfected host cell; and (3) determining the effect on reporter gene expression.

In a preferred embodiment, the invention provides a screening assay for the identification of substances capable of altering the expression from the NKX3.1 promoter, comprising:

(a) measuring the level of expression of a reporter gene in a test cell, wherein said test cell is transformed with a recombinant DNA molecule comprising a reporter gene operably linked to a DNA molecule comprising the promoter of NKX3.1, and wherein a candidate NKX3.1 trans-acting agent is administered to said test cell;

(b) measuring the level of expression of said reporter gene in a control cell, wherein said control cell is transformed with the recombinant DNA molecule of step (a); and (c) comparing the level of expression of said reporter gene in said test cell to the level of said reporter gene in said control cell.

Suitable and preferred host cells, transfection methods, expression vectors, promoters, and reporter genes, are described above and will be known in the art.

Gene Therapy

Gene therapy has been proposed as a method for treating disease states and genetic disorders that lack effective therapies. Gene therapy techniques can also be applied as a method to control expression of a protein and to assess its ability to modulate cellular events.

The genomic clone for the NKX3.1 gene of the present invention has been isolated (FIG. 5). This clone contains the promoter region for the NKX3.1 gene which appears to be a prostate tissue specific promoter. Thus, the NKX3.1 promoter region could be useful as a prostate-specific DNA element to drive expression of any gene of interest in gene therapy techniques. Promoter elements are shown in FIG. 5.

Thus, for example, cells from a patient may be engineered with a polynucleotide, such as a DNA or RNA, encoding a polypeptide ex vivo, and the engineered cells then can be provided to a patient to be treated with a polypeptide. For example, cells may be engineered ex vivo by the use of a retroviral plasmid vector containing RNA encoding a desired polypeptide. Such methods are well-known in the art and their use in the present invention will be apparent from the teachings herein.

Similarly, cells may be engineered in vivo for expression of a polypeptide in vivo by procedures well-known in the art. For example, a polynucleotide may be engineered for expression in a replication defective retroviral vector, as discussed above.

The retroviral expression construct then may be isolated and introduced into a packaging cell which is tranduced with a retroviral plasmid vector containing RNA encoding a desired polypeptide such that packaging cell now produces infectious viral particles contain the gene of interest. These producer cells may be administered to a patient for engineering cells in vivo and expression of the polypeptide in vivo. These and other methods for administering a polypeptide of interest by such methods will be apparent to those skilled in the art from the teachings of the present invention.

Retroviruses from which the retroviral plasmid vectors mentioned above may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mouse mammary tumor virus. In one embodiment, the retroviral plasmid vector is derived from Moloney Murine Leukemia Virus.

The retroviral plasmid vector is employed to transduce packaging cell lines to form producer cell lines. Example of packaging cells which may be transfected include, but are not limited to, PE501, PA317, Y-2, Y-AM, PA12, T19-14x, VT-19-17-H2, YCRE, YCRIP, GP+E-86, GP+envAm12, and DAN cell lines as described in Miller A., *Human Gene Therapy* 1: 5-14 (1990). The vector may be transduced into the packaging cells though any means known in the art. Such means include, but are not limited to, electroporation, the use of liposomes, and $CaPO_4$ precipitation. In one alternative, the retroviral vector plasmid vector may be encapsulated into a liposome, or coupled to a lipid and then administered to a host.

The producer cell line will generate infectious retroviral vector particles, which include the nucleic acid sequence(s) encoding a desired polypeptide. Such retroviral particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well fibroblasts, epithelial cells and endothelial cells.

In addition to retroviral vectors, a variety of vectors have also been developed for gene delivery. These vectors derive from herpes simplex virus type 1 (HSV-1), adenovirus, adeno-associated virus (AAV) and retrovirus constructs (for review see Friedmann, T., *Trends Genet.* 10:210-214 (1994); Jolly, D., *Cancer Gene Therapy* 1 (1994); Mulligan, R. C., *Science* 260:926-932 (1993); Smith, F. et al., *Rest. Neurol. Neurosci.* 8:21-34 (1995)). Vectors based on HSV-1, including both recombinant virus vectors and amplicon vectors, as well as adenovirus vectors can assume an extrachromosomal state in the cell nucleus and mediate limited, long term gene expression. HSV-1 amplicon vectors can be grown to relatively high titers ($10^7$ transducing units/ml) and have the capacity to accommodate large fragments of foreign DNA (at least 15 kb, with 10 concatemeric copies per virion). AAV vectors (rAAV), available in comparable titers to amplicon vectors, can deliver genes (<4.5 kb) to postmitotic, as well as mitotic cells in combination with adenovirus or herpes virus as helper virus. Long term transgene expression is achieved by replication and formation of "episomal" elements and/or through integration into the host cell genome at random or specific sites (for review see Samulski, R. J., *Current Opinion in Genetics and Development* 3:74-80 (1993); Muzyczka, N., *Curr. Top. Microbiol. Immunol.* 158:97-129 (1992)). HSV, adenovirus and rAAV vectors are all packaged in stable particles. Retrovirus vectors can accommodate 7-8 kb of foreign DNA and integrate into the host cell genome. Recent studies have demonstrated that elements from different viruses can be combined to increase the delivery capacity of vectors. For example, incorporation of elements of the HIV virion, including the matrix protein and integrase, into retrovirus vectors allows transgene cassettes to enter the nucleus of non-mitotic, as well as mitotic cells and potentially to integrate into the genome of these cells (Naldini, L. et al., *Science* 272:263-267 (1996)); and inclusion of the vesicular somatitis virus envelope glycoprotein (VSV-G) increases stability of retrovirus particles (Emi, N. et al., *J. Virol.* 65:1202-1207 (1991)). As another example, inclusion of elements from Epstein Barr virus (EBV)—the DNA origin of replication, oriP, and the EBNA-1, within HSV vectors allows nuclear replication of vectors in dividing human cells (Wang and Vos, in press).

Both HSV and AAV can deliver genes to dividing and non-dividing cells. In general, HSV virions are considered more highly infectious than AAV virions, with a ratio of virus particles: infectious units in the range of 10 for HSV (Browne, H. et al., *J. Virol.* 70:4311-4316 (1996)) and up to thousands for AAV (Snyder, R. O. et al., In Current Protocols in Human Genetics, Eds. Dracopoli, N. et al., John Wiley and Sons: New York (1996), pp. 1-24), and both having a broad species range. These vectors deliver linear, double stranded DNA to the nucleus. If replication-competent HSV helper virus accompanies the vector DNA it commences replication as a rolling circle. If the helper virus is replication-defective or absent, the amplicon DNA is thought to exist as a linear extrachromosomal element without any defined episomal structure.

HSV-1 based vectors allow replication and packaging of DNA as a concatenate in HSV-1 virions in the presence of HSV-1 helper virus (Kwong, A. D. and Frenkel, N., *In Viral Vectors*, Eds. M. G, Kaplitt and A. D. Loewy, Academic Press: New York (1995), pp. 25-42). Vectors based on either HSV-1 or AAV can be generated using either HSV-1 or AAV helper virus packaging systems well known in the art. In addition, vectors can be generated free of helper virus using the helper virus-free packaging system described by Fraefel, C. et al., *J. Virol.* 70: 7190-7197 (1996).

These gene therapy vectors, when encapsulated in either a herpesviral particle coat or an adeno-associated viral particle coat, capable of binding to a target host cell and introducing into the target host cell the polynucleotide sequence carried by the vector.

For the treatment of cancers and tumors, gene therapy can be used to introduce a gene into the tumor cells that expresses a protein which is toxic or can trigger a toxic effect against tumor cells. Genes for transfer into the neoplastic cells by the vectors are selected from those which target host cell usually by expression of a gene product in the host neoplastic cells. "Gene product" broadly refers to proteins encoded by the particular gene. For the purposes of the invention, gene product also includes transcription products of the gene, particularly for use as antisense RNA. Genes are selected whose gene products serve to identify host cells, slow down or temporarily stimulate host cell growth in order to render the host cell more sensitive to chemotherapeutic agents and/or whose products target the host cell for cell death. Cell death can be accomplished by contacting the host cells, containing the gene product, with a subsequent treatment, either physical or chemical treatment. Alternatively, the gene products themselves may serve to kill the host cells or slow down cell growth. Such genes and gene products are known to those skilled in the art. The host cells targeted by the present hybrid vectors are those cells into which the hybrid vector infects and expresses the desired gene product and thus can constitute neoplastic cells infected by the hybrid vectors.

Useful gene products comprise: tumor suppressor genes, which encode transcription factors which suppress cell growth, such as the Rb gene for retinoblastoma or the p53 gene in colon cancer (Huang et al., *Science* 242: 1563-1566 (1988); Barker, et al., *Science* 249: 912-915 (1980); toxic proteins that are released by cells, such as a fusion protein comprising a toxin coupled to EGF ligand (Heinbrook et al., *Proc. Natl. Acad. Sci. USA* 87: 4697 (1990)); products which themselves are capable of selective cell killing, such as antisense nucleic acid for essential cell proteins, such as replication proteins which serve to render the host cells incapable of further cell growth and division (Rosengberg et al., *Nature* 313: 703-706 (1985); Preiss et al., Nature 313:27-32 (1985) McGarry et al., *Proc. Natl. Acad. Sci. USA* 83: 399-403 (1986); and prodrug activating genes such as thymidine kinase (Kramm et al., *Brain Pathology* 5:345-381 (1995)).

Thus, one embodiment of the invention provides for a nucleic acid sequence encoding the polypeptide of interest contained in either the retroviral or amplicon vectors described above and placed under the control of the NKX3.1 promoter region of the present invention. Thus, such a vector having the NKX3.1 prostate-specific promoter element(s) operably linked to a gene of interest, provides a vector that can specifically target the expression of such a gene to prostate tissue.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a NKX3.1 protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15-25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

The NKX3.1 gene appears to be located on 8p21, a region which is deleted in up to 60-80% of prostate cancers and which suggests a role for the gene in androgen-driven maintenance of prostate tissue phenotype. (See, Example 6 below).

Having generally described the invention, the same will be more readily understood by reference to the following examples, which are provided by way of illustration and are not intended as limiting.

EXAMPLES

Example 1

Expression and Purification of NKX3.1 in *E. coli*

The bacterial expression vector pQE9 (pD10) is used for bacterial expression in this example. (QIAGEN, Inc., 9259 Eton Avenue, Chatsworth, Calif., 91311). pQE9 encodes ampicillin antibiotic resistance ("Amp'") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag")) covalently linked to the amino terminus of that polypeptide.

The DNA sequence encoding the desired portion NKX3.1 protein lacking the hydrophobic leader sequence is amplified from the deposited cDNA clone using PCR oligonucleotide primers which anneal to the amino terminal sequences of the desired portion of the NKX3.1 protein and to sequences in the deposited construct 3' to the cDNA coding sequence. Additional nucleotides containing restriction sites to facilitate cloning in the pQE9 vector are added to the 5' and 3' primer sequences, respectively.

For cloning the mature protein, the 5' primer has the sequence 5' GCG<u>GGATCC</u>ATGCTCAGGGTTCCGGAG 3' (SEQ ID NO: 15) containing the underlined BamHI restriction site followed by 18 nucleotides complementary to the amino terminal coding sequence of the NKX3.1 sequence in FIG. 1. One of ordinary skill in the art would appreciate, of course, that the point in the protein coding sequence where the 5' primer begins may be varied to amplify a DNA segment encoding any desired portion of the complete NKX3.1 protein shorter or longer than the complete sequence. The 3' primer has the sequence 5' GCG <u>AGCTTT</u>TACCCAAAAGCTGGGCT 3' (SEQ ID NO: 16) containing the underlined HindIII restriction site followed by 18 nucleotides complementary to the non-coding sequence of the NKX3.1 DNA sequence in FIG. 1.

The amplified NKX3.1 DNA fragment and the vector pQE9 are digested with BamHI and HindIII and the digested DNAs are then ligated together. Insertion of the NKX3.1 DNA into the restricted pQE9 vector places the NKX3.1 protein coding region downstream from the IPTG-inducible promoter and in-frame with an initiating AUG and the six histidine codons.

The ligation mixture is transformed into competent *E. coli* cells using standard procedures such as those described in Sambrook et al, *Molecular Cloning: a Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan'"), is used in carrying out the illustrative example described herein. This strain, which is only one of many that are suitable for expressing NKX3.1 protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 µg/ml) and kanamycin (25 µg/ml). The O/N culture is used to inoculate a large culture, at a dilution of approximately 1:25 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3-4 hours at 4° C. in 6M guanidine-HCl, pH8. The cell debris is removed by centrifugation, and the supernatant containing the NKX3.1 is loaded onto a nickel-nitrilo-tri-acetic acid ("NiNTA") affinity resin column (available from QIAGEN, Inc., supra). Proteins with a 6×His tag bind to the NI-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH8, the column is first washed with 10 volumes of 6 M guanidine-HCl, pH8, then washed with 10 volumes of 6 M guanidine-HCl pH6, and finally the NKX3.1 is eluted with 6 M guanidine-HCl, pH5.

The purified protein is then renatured by dialyzing it against phosphate buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH6 buffer plus 200 mM NaCl. The purified protein is stored at 4° C. or frozen at −80° C.

Example 2

Cloning and Expression of NKX3.1 Protein in a Baculovirus Expression System

In this illustrative example, the plasmid shuttle vector pA2 GP is used to insert the cloned DNA encoding the protein into a baculovirus to express the NKX3.1 protein, using a baculovirus leader and standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by the secretory signal peptide (leader) of the baculovirus gp67 protein and convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31-39.

The cDNA sequence encoding the NKX3.1 protein in the deposited clone shown in FIG. 1 (SEQ ID NO:2), is amplified using PCR oligonucleotide primers corresponding to the 5' and 3' sequences of the gene.

The 5' primer has the sequence 5' GCG GGATCCCATGCTCAGGGTTCCGGAG 3' (SEQ ID NO: 17) containing the underlined BamHI restriction enzyme site followed by 18 bases of the sequence of the mature NKX3.1 protein shown in FIG. 1, beginning with the indicated N-terminus of the mature protein. The 3' primer has the sequence 5'GCGGATCCTTACCCAAAAGCTGGGCT 3' (SEQ ID NO: 18) containing the underlined BamHI restriction site followed by 18 nucleotides complementary to the 3' noncoding sequence in FIG. 1.

The amplified fragment is isolated from a 1% agarose gel using a commercially available kit ("GENECLEAN™," BIO 101 Inc., La Jolla, Calif.). The fragment then is digested with BamHI and again is purified on a 1% agarose gel. This fragment is designated herein "F1".

The plasmid is digested with the restriction enzymes BamHI and optionally, can be dephosphorylated using calf intestinal phosphatase, using routine procedures known in the art. The DNA is then isolated from a 1% agarose gel using a commercially available kit ("GENECLEAN™" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue ( STRATAGENE™ Cloning Systems, La Jolla, Calif.) cells are transformed with the ligation mixture and spread on culture plates. Bacteria are identified that contain the plasmid with the human NKX3.1 gene using the PCR method, in which one of the primers that is used to amplify the gene and the second primer is from well within the vector so that only those bacterial colonies containing the NKX3.1 gene fragment will show amplification of the DNA. The sequence of the cloned fragment is confirmed by DNA sequencing. This plasmid is designated herein pBacNKX3.1.

Five µg of the plasmid pBacNKX3.1 is co-transfected with 1.0 µg of a commercially available linearized baculovirus DNA ("BACULOGOLD™ baculovirus DNA", Pharmingen, San Diego, Calif.), using the lipofection method described by Felgner et al., *Proc. Natl. Acad. Sci. USA* 84:7413-7417 (1987). 1 µg of BACULOGOLD™ virus DNA and 5 µg of the plasmid pBacNKX3.1 are mixed in a sterile well of a microtiter plate containing 50 µl of serum-free Grace's medium (Life Technologies Inc., Gaithersburg, Md.). Afterwards, 10 µl LIPOFECTIN™ plus 90 µl Grace's medium are added, mixed and incubated for 15 minutes at room temperature. Then the transfection mixture is added drop-wise to Sf9 insect cells (ATCC™ CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-NKX3.1.

To verify the expression of the NKX3.1 gene, Sf9 cells are grown in Grace's medium supplemented with 10% heat inactivated FBS. The cells are infected with the recombinant baculovirus V-NKX3.1 at a multiplicity of infection ("MOI") of about 2. Six hours later the medium is removed and is replaced with SF900 II medium minus methionine and cysteine (available from Life Technologies Inc., Rockville, Md.). If radiolabeled proteins are desired, 42 hours later, 5 µCi of $^{35}$S-methionine and 5 µCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

Example 3

Cloning and Expression of NKX3.1 in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (PHARMACIA™, Uppsala, Sweden), pRSVcat (ATCC™ 37152), pSV2dhfr (ATCC™ 37146) and pBC12MI (ATCC™ 67109). Mammalian host cells that could be used include, human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277-279 (1991); Bebbington et al., *Bio/Technology* 10: 169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology,* 438-447 (March, 1985)) plus a fragment of the CMV-enhancer (Boshart et al., *Cell* 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3A

Cloning and Expression in COS Cells

The expression plasmid, pNKX3.1 HA, is made by cloning a cDNA encoding NKX3.1 into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the NKX3.1 is cloned into the polylinker region of the vector so that recombinant protein expression is directed by the CMV promoter. The plasmid construction strategy is as follows. The NKX3.1 cDNA of the deposited clone is amplified using primers that contain convenient restriction sites, much as described above for construction of vectors for expression of NKX3.1 in *E. coli.* Suitable primers include the following, which are used in this example. The 5' primer, containing the underlined BamHI site, a Kozak sequence, an AUG start codon and 18 bases of the 5' coding region of the complete NKX3.1 has the following sequence: 5'GCG GGATCCCATGCTCAGGGTTCCGGAG 3' (SEQ ID NO:17). The 3' primer, containing the underlined BamHI site, a stop codon, and 18 bases of 3' coding sequence has the following sequence (at the 3' end): 5'GCG GATCCTTACCCAAAAGCTGGGCT 3' (SEQ ID NO:18).

The PCR amplified DNA fragment and the vector, pcDNAI/Amp, are digested with BamHI and then ligated. The ligation mixture is transformed into *E. coli* strain SURE (available from STRATAGENE™ Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the NKX3.1-encoding fragment.

For expression of recombinant NKX3.1, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of NKX3.1 by the vector.

Expression of the NKX3.1-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3B

Cloning and Expression in CHO Cells

The vector pC4 is used for the expression of NKX3.1 protein. Plasmid pC4 is a derivative of the plasmid pSV2-dhfr (ATCC™ Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, LIFE TECHNOLOGIES™) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J Biol. Chem.* 253:1357-1370, Hamlin, J. L. and Ma, C. 1990, *Biochem. et Biophys. Acta*, 1097:107-143, Page, M. J. and Sydenham, M. A. 1991, *Biotechnology* 9:64-68). Cells grown in increasing concentrations of MTX develop resistance to the drug by overproducing the target enzyme, DHFR, as a result of amplification of the DHFR gene. If a second gene is linked to the DHFR gene, it is usually co-amplified and overexpressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., *Molecular and Cellular Biology*, March 1985:438-447) plus a fragment isolated from the enhancer of the immediate early gene of human cytomegalovirus (CMV) (Boshart et al., *Cell* 41:521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the NKX3.1 in a regulated way in mammalian cells (Gossen, M., & Bujard, H. 1992, *Proc. Natl. Acad. Sci. USA* 89: 5547-5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and then dephosphorylated using calf intestinal phosphatase by procedures known in the art. The vector is then isolated from a 1% agarose gel.

The DNA sequence encoding the complete NKX3.1 protein including its leader sequence is amplified using PCR oligonucleotide primers corresponding to the 5' and 3' sequences of the gene. The 5' primer has the sequence 5'GCG GGATCCCATGCTCAGGGTTCCGGAG 3' (SEQ ID NO: 17) containing the underlined BamHI restriction enzyme site followed by an efficient signal for initiation of translation in eukaryotes, as described by Kozak, M., *J. Mol. Biol.* 196:947-950 (1987), and 18 bases of the coding sequence of NKX3.1 shown in FIG. 1 (SEQ ID NO:1). The 3' primer has the sequence 5' GCGGATCCTTACCCAAAAGCTGGGCT 3' (SEQ ID NO: 19) containing the underlined BamHI restriction site followed by 18 nucleotides complementary to the non-translated region of the NKX3.1 gene shown in FIG. 1 (SEQ ID NO: 1).

The amplified fragment is digested with the endonuclease BamHI and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5 μg of the plasmid pSV2-neo using LIPOFECTIN™ (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100-200 µM. Expression of the desired gene product is analyzed, for instance, by SDS-PAGE and Western blot or by reverse phase HPLC analysis.

Example 4

Tissue Distribution of NKX3.1 mRNA Expression

To examine the tissue specificity of NKX3.1 expression, two separate Northern analyses were performed using mRNA derived from overlapping sets of human tissues using methods described by, among others, Sambrook et al., cited above.

Materials and Methods

A cDNA probe containing the entire nucleotide sequence of the NKX3.1 protein (SEQ ID NO: 1) was labeled with $^{32}$P using the REDIPRIME™ DNA labeling system (Amersham Life Science), according to manufacturer's instructions. After labeling, the probe was purified using a CHROMA SPIN-100™ column (CLONTECH™ Laboratories, Inc.), according to manufacturer's protocol number PT1200-1. The purified labeled probe was then used to examine various human tissues for NKX3.1 mRNA.

Multiple Tissue Northern (MTN) blots containing various human tissues (H) or human immune system tissues (IM) are obtained from CLONTECH™ and are examined with the labeled probe using EXPRESSHYB™ hybridization solution (CLONTECH™) according to manufacturer's protocol number PT1190-1. Following hybridization and washing, the blots are mounted and exposed to film at −70° C. overnight, and films developed according to standard procedures.

Cell lines were grown in medium containing 10% fetal bovine serum. Human peripheral blood lymphocytes (HuPBL) were isolated from a normal donor (FICOLL™-Paque, PHARMACIA™). Total cellular RNA was isolated from each of the cell lines using the TRIZOL™ RNA isolation reagent (Gibco BRL). Ten microgram aliquots were resolved on a 1% agarose-formaldehyde gels and transferred to a nylon membrane (Hybond-N, Amersham) essentially as described (Sambrook et al., 1988). Filters were prehybridized for 1 hour in SLURP (7 mM Tris-HCl pH 7.5, 4×SSC, 10% dextran sulfate, 0.8×Denhardts solution, 40% formamide, 20 mg/mL salmon sperm DNA and 0.5% SDS). NKX3.1 or glyceraldehyde-3-phosphate dehydrogenase (GAPDH) cDNAs were labeled with $^{32}$P dCTP by random priming, denatured, added to the prehybridization mix, and hybridized overnight at 42° C. Filters were washed at 42° C. for 10 min, then at room temperature, in 2×SSC/0.1% SDS, followed by a high stringency wash at 65° C. for 40 min 0.2×SSC/0.1% SDS. Washed filters were then dried and exposed to X-ray film.

Results

An abundant 3.5 kb NKX3.1 mRNA was detected in prostate and at much lower level in testis. NKX3.1 mRNA was not detected in several other adult tissues including brain, kidney, small intestine, pancreas, heart, liver, lung, thymus, spleen, placenta, colon, lymphocytes and ovary. We also examined the expression of NKX3.1 mRNA in a variety of cultured cells including both transformed and non-transformed human cell lines (Table 2, below). NKX3.1 expression was seen only in the hormone-responsive, androgen receptor-positive LNCaP prostate cancer cell line. However NKX3.1 expression was not observed in either of the two androgen receptor-negative cell lines, PC-3 and DU-145, nor in eleven other cell lines of varied tissue origin. Interestingly, other HOX genes tested were expressed in several of the same cell-lines indicating even more strongly that NKX3.1 exhibits a uniquely restricted tissue expression pattern. These findings indicate that NKX3.1 is indeed a new prostate-specific gene. Since NKX3.1 is a member of the homeobox family, it may be involved in establishing the developmental cascade of specific cell types, suggesting that this gene may have a role in the development and differentiation of prostatic tissue. It is also intriguing that the NKX3.1 expression has apparently been lost in both of the androgen independent cell lines tested, but not in the androgen-dependent cell line LNCaP, indicating that expression of the gene may be androgen-regulated.

TABLE 2

Cell lines used for Northern blot analysis
Cell Line (Tissue)

| | |
|---|---|
| FS4 (Human diploid fibroblast)[1] | RT-4 (Bladder Carcinoma)[5] |
| HuPBL (Peripheral Blood Lymphocyte) | HTB-44 (Kidney Carcinoma)[5] |
| DAOY (Medulloblastoma)[2] | OVCAR-3 (Ovarian Carcinoma)[5] |
| BHM22 (B cell Leukemia)[3] | CATES-1B (Embryonal Carcinoma)[2] |
| 8392 (EBV-Transformed B-cell)[3] | PC3 (Prostate Carcinoma)[6] |
| HELA (Cervical Carcinoma)[4] | LNCaP (Prostate Carcinoma)[6] |
| SW480 (Colon Carcinoma)[3] | DU-145 (Prostate Carcinoma)[2] |

Cell lines were obtained from the following sources and/or generously provided by the following laboratories:
[1]J. Vilcek, NYU Medical Center;
[2]ATCC ™;
[3]A. Rabson, Center for advanced Biotechnology and Medicine;
[4]C. Gelinas, Center for Advanced Biotechnology and Medicine;
[5]The Cancer Institute of New Jersey;
[6]S. Ward, University of Medicine and Dentistry New Jersey.

Example 5A

Androgen Regulation of NKX3.1

Since NKX3.1 was expressed in LNCaP cells, which are dependent on the presence of physiologic levels of androgen for growth and tumorigenesis (Burnes et al., *Prostate* 9:247-259 (1986); Olea et al., *Endocrinology* 126:1457-1463 (1990)), we examined whether NKX3.1 mRNA levels are responsive to androgen stimulation.

Materials and Methods

For the androgen regulation experiments, parallel cultures of PC3 or LNCaP cells were incubated in fetal bovine serum (10%) containing medium or were incubated in medium containing 10% charcoal dextran treated human serum (SIGMA™) as indicated. The synthetic androgen R1881 (NEN-DUPONT™) was dissolved in 100% ethanol. Mock induced cultures were treated with an equal volume of 100% ethanol alone. Northern analysis was then performed as described above in Example 4.

Results

In standard serum-containing growth medium (control cells), NKX3.1 mRNA was detected in Northern analyses at a level similar to that seen in the previous cell-line survey. However, when cells were grown in the absence of androgen stimulation, NKX3.1 message was reduced to undetectable levels. Addition of the synthetic androgen R1881 to these cultures in concentrations as low an 0.3 nm resulted in an restoration NKX3.1 mRNA to control levels and higher concentrations of R1881 resulted in a dose-dependent increase in the expression gene. In contrast, NKX3.1 mRNA was not detected in the androgen-independent prostate carcinoma line PC-3 in either the absence or presence of R1881. Experiments have demonstrated that NKX3.1 expression in LNCaP cells is exquisitely sensitive to the presence or absence of androgens and that androgen stimulation is at the transcription level and does not require synthesis of additional cellular proteins upon stimulation of the hormone. These results raise the possibility that NKX3.1 is part of the prostate cell's primary response to androgen stimulation and indicate that the gene is a candidate for playing a central role in the differentiation of normal prostatic tissue and the reversal of normal differentiation seen during cancer progression.

Example 5B

NKX3.1 Regulation in Response to Orchidectomy

The maintenance of differentiated functions within the prostate is well-established to be androgen-dependent (Davis, P. and Eaton, C. L., *J. Endocrinol.* 131:5-17 (1991)). Castration-induced androgen deprivation leads to a rapid shut-off of genes encoding prostate-specific secretary proteins (Mills, L. S. et al., *EMBO J.* 6:3711-3717 (1987)). To determine whether Nkx-3.1 was regulated in response to orchidectomy, RNA was extracted from prostates harvested at various time-points after castration, but prior to the onset of an atrophic state.

Materials and Methods

Orchidectomy was performed on 6-week old CD-1 mice as described for rats (Waynforth, H. B., *Experimental and Surgical Techniques in the Rat*, Academic Press Inc., San Diego, Calif. (1980)). RNA was extracted from total prostate, pooled from two mice, at each time-point after castration. Densitometric analysis of Northern blot autoradiograms was performed using Bioimage Software version 4.6P (Bioimage Inc., Ann Arbor, Mich.).

Results

Northern blot analysis of the RNA extracted from prostates revealed that by 24 hours after castration, the steady-state level of NKX3.1 mRNA was decreased nearly 10-fold. By 96 hours, the level was decreased 30-fold. These data suggest that the maintenance of a high level of expression of NKX3.1 requires testicular androgens. The same RNA blot was subsequently hybridized with a probe that detected the mRNA encoding a secreted protease inhibitor, mp12, that has been demonstrated to be androgen-dependent (Mills, L. S. et al., *EMBO J.* 6:3711-3717 (1987)). A comparison of the kinetics and extent of downregulation showed that the level of mp12 mRNA was decreased by more than 70-fold by 24 hours after castration. At 96 hours, mp12 mRNA was no longer detectable by Northern analysis, whereas NKX3.1 mRNA fell to a basal level that was maintained for at least several more days. These data suggest that NKX3.1 expression is androgen-responsive, but also show a low, basal level of expression that may not be androgen-dependent.

Example 6

Chromosomal Mapping of NKX3.1

To demonstrate the chromosomal location of the NKX3.1 gene, a 20 kb genomic NKX3.1 clone was used as a probe for fluorescence in situ hybridization to human chromosome metaphase spreads (Lawrence et al., *Cell* 52:51-61 (1988)).

Materials and Methods

An NKX3-1 lambda genomic clone was isolated by standard techniques (Sambrook et al., 1989). This DNA was nick-translated using digoxigenin-11-dUTP (Boehringer Mannheim) and in situ hybridization was done as detailed in Johnson et al., *Methods in Cell Biol.* 35:73-99 (1991). Individual chromosomes were counterstained with DAPI and color digital images, containing both DAPI and gene signal were recorded using a triple-band pass filter set (Chroma Technology, Inc. Brattleboro, Vt.) in combination with a charged couple-device camera (Photometrics, Inc. Tucson, Ariz.) and variable excitation wave length filters, which allows for recording multi-color images without image shift (Johnson et al., *Genetic analysis: Techniques and applications* 8:75-76 (1991)). In experiments analyzing the position of more than one gene or marker on 8p, each DNA probe was labeled separately with either digoxigenin or biotin (Gibco/BRL) and the two were mixed at different ratios for each DNA probe during hybridization in the triple-label experiments. The hybridized signal was subsequently detected using Rhodamine-conjugated anti-digoxigenin antibodies and FITC-streptavidin (Boehringer-Mannheim). Individual probes were identified based on the red:green ratio of the recorded signal. Images were analyzed using the ISEE software package (Inovision Corp. Durham, N.C.) and in some cases the gene signal was pseudo-colored in the final image for clarity.

Results

Approximately 20 metaphase chromosome spreads were analyzed by eye, most of which had a doublet signal characteristic of genuine hybridization on at least one chromosome 8. Doublet signal was not detected on any other chromosome. Detailed analysis of 10 individual chromosomes, using a combination of fractional length measurements and fluorescence banding, combined with high-resolution image analysis, indicated that the NKX3.1 gene is positioned within band 8p21. Allelic deletions associated with this region of 8p are frequently reported in prostate cancer tissue and are thought to occur at two sites, one within band 8p22 and other within 8p21, making the precise assignment of the NKX3.1 band position of critical importance. Therefore, the position of the NKX3.1 was confirmed by co-mapping the gene with markers on 8p21 and preliminary evidence indicates that the gene is within a no more than a few megabases of the 8p21 site that is frequently deleted in prostate cancer cells. Because a gene within this region of 8p21 is thought to be involved in the loss of androgen-driven differentiated prostatic phenotype it is reasonable to suggest that this might be that gene. This is consistent with a role for NKX3.1 in the maintenance of prostate differentiation.

Example 7

NKX3.1 Homeodomain Exhibits NK-Like DNA Binding Specificity

The human and mouse NKX3.1 cDNAs have a high degree of sequence similarity of its homeodomain with that of Drosophila NK-3. Particularly well conserved are residues in helix III and the N-terminal arm, which are known to determine the DNA binding specificity of other homeodomains (Damante, G. and Di Lauro, R., Proc. Natl. Acad. Sci. USA 88:5388-5392 (1991); Ebu Isaac, V. et al., Biochem. 34:7127-7134 (1995)), and to contact DNA directly (Gehring, W. J. et al., Cell 78:211-223 (1994)). NKX3.1 homeodomain contains a tyrosine residue at position 54, which is the most distinguishing feature of NK homeodomains, and is largely responsible for the atypical DNA binding specificities of this class of homeodomains relative to the prototypic (e.g., Antennadia-like) homeodomains (Chen, C. Y. and Schwartz, R. J., J. Biol. Chem. 270:15626-15633 (1995); Damante, G. and Di Lauro, R., Proc. Natl. Acad. Sci. USA 88:5388-5392 (1991); Damante, G. et al., Nucleic Acids Res. 22:3075-3083 (1994); Guazzi, S. et al., EMBO J. 9:3631-3639 (1990); Harvey, R. P., Dev. Biol. 178:203-216 (1996)). In particular, NK-2 have been shown to interact preferentially with DNA sites that contain a "CAAG" core, rather than the prototype "TAAT" core recognized by most other homeodomains (Chen, C. Y. and Schwartz, R. J., J. Biol. Chem. 270:15626-15633 (1995); Damante, G. and Di Lauro, R., Proc. Natl. Acad. Sci. USA 88:5388-5392 (1991)).

To investigate the DNA binding specificity of the murine NKX3.1 homeodomain, gel mobility shift analyses were performed using highly purified recombinant protein. Given its high content of proline and arginine residues (which are inefficiently translated in E. coli), it was predicted that the full length murine NKX3.1 would be poorly expressed in bacterial cells (Abate, C. et al., Mol. Cell. Biol. 11:3624-3632 (1991)). Therefore, the region containing the murine homeodomain (NKX3.1 HD) was expressed as a hexahistidine fusion polypeptide in E. coli, and obtained highly purified protein by nickel affinity chromatography. Human NKX3.1HD was also produced and purified, and as anticipated, these proteins behaved identically with respect to their expression, purification and DNA binding properties.

Materials and Methods

In vitro transcription/translation was performed using the pBLUESCRIPT™-NKX3.1 plasmid as a template with the TnT coupled transcription/translation system (PROMEGA™) according to the protocol of the manufacturer.

To produce the NKX3.1 homeodomain (NKX3.1 HD) in E. coli, sequences encoding amino acids 122 to 188 were amplified by PCR using the primers that contained restriction sites for cloning into the BamHI and HindIII sites of the bacterial expression plasmid, pQE-9 (Qiagen). Polypeptides were produced in E. coli as hexahistidine fusion proteins and purified by nickel affinity chromatography as previously described (Catron, K. M. et al., Mol. Cell. Biol. 13; 2354-2365 (1993)).

The DNA binding experiments were performed as follows. Briefly, increasing amounts of protein were incubated in binding buffer [10 mM Tris-HCl (pH 0.6), 50 mM NaCl, 5% glycerol, 5% sucrose, 0.2 mM EDTA, 7.5 mM MgCl$_2$, 0.5 mg/mL bovine serum albumin, 0.1% NP-40, 10 mM DTT, 500 μg of poly-didC] with 4×10$^4$ cpm of $^{32}$P-labeled, double stranded oligonucleotide for 20 min at room temperature. The sequences of the DNA binding sites were as follows (top strand shown):

5'CACTGCCCAGTCAAGTGTTCTTGA 3' [C site, Guazzi, S. et al., EMBO J. 9:3631-3639 (1990))] (SEQ ID NO:20)
5'CACTGCCCAGTCACGTGTTCGTGA 3' (SEQ ID NO:21)
5' ACACTAATTGGAGGC 3' [site 6, (Catron, K. M. et al., Mol. Cell. Biol. 13; 2354-2365 (1993))] (SEQ ID NO:22)
5' ACACTACTTGGAGGC 3' [site 6-19, (Catron, K. M. et al., Mol. Cell. Biol. 13; 2354-2365 (1993))] (SEQ ID NO:23)
5'CTCTAATGGCTTTTTTCTC 3' [site BS2, (Guazzi, S. et al., EMBO J. 9:3631-3639 (1990))] (SEQ ID NO:24)

Results

The DNA binding specificity of NKX3.1HD was examined by gel mobility shift analysis using various DNA sites identified for NK-like and Antennapedia-like homeodomains. The DNA sites were as follows: (i) the consensus DNA site for the NKX2.1 homeodomain (TCAAGTG) (Guazzi, S. et al., EMBO J. 9:3631-3639 (1990)) and a mutated version of this site that contains nucleotide substitutions within the CAAG core (TCACGTG); and (ii) the consensus DNA site identified for an Antennapedia-like homeodomain (Msx1) (CTAATTG), a mutated version of this site that contains nucleotide substitutions within the TAAT core (CTACTTG), or one that contains nucleotide substitutions 3' of the TAAT core (CTAATGG) (Catron, K. M. et al., Mol. Cell. Biol. 13; 2354-2365 (1993); Guazzi, S. et al., EMBO J. 9:3631-3639 (1990)). To compare the relative DNA binding affinity of NKX3.1 HD for these DNA sites, gel mobility shift analysis was performed with varying concentrations of the purified protein, using equimolar amounts of each site. Of the various DNA sites tested, NKX3.1HD interacted preferentially with the site containing the "CAAG" core. NKX3.1HD also bound to DNA sites containing the "TAAT" core, albeit with lower apparent affinity. The specificity of the interaction was apparent from the lack of NKX3.1HD binding to DNA sites containing substitutions within the "CAAG" or "TAAT" cores. These results demonstrate that NKX3.1HD exhibits similar DNA binding specificity as NK-2 homeodomains; namely a preferential association with DNA sites containing a "CAAG" core and relatively low affinity interaction with DNA sites containing a "TAAT" core.

Example 8

Expression of Murine NKX3.1 within the Prostate

The mouse prostate is comprised of four paired components that are heterogeneous both in morphology and function (Frohman, M., Meth. Enzymol. 218:340-356 (1993)). To further characterize expression of NKX3.1 expression within the prostate, the ventral prostate, the dorsolateral prostate, and the coagulating gland (anterior prostate) were dissected from adult animals. Microdissection of prostate glands into component lobes was performed as described (Sugimura, Y. et al., Biol. Reprod. 34:961-971 (1986)). The dorsolateral prostate was further subdivided into its dorsal and lateral components (Sugimura, Y. et al., Biol. Reprod. 34:961-971 (1986)).

To determine whether NKX3.1 mRNA was differentially distributed among the four lobes, Northern blot analysis was performed on RNA extracted from pools of individual lobes. All four lobes expressed NKX3.1 at a similar steady-state level relative to the housekeeping gene β-actin, suggesting that this gene may be important for regulating functions that are shared between them.

To characterize the cellular distribution of NKX3.1 within the prostate gland, in situ hybridization to histological sections of all four components was performed. In situ hybridization was performed essentially as described (Bogarad, L. D. et al., *Develop. Biol.* 133; 537-549 (1989)), using a 530-bp Bgl II-Pst I fragment derived entirely from the mouse NKX3.1 3' noncoding region. The architecture of the adult prostate is relatively simple, consisting principally of a series of branching ducts lined with secretary epithelial cells (Sugimura, Y. et al., *Biol. Reprod.* 34:961-971 (1986)). The ducts are wrapped by condensed stromal sleeves with sparse connective tissue interspersed between the ducts. Analysis of serial sections hybridized with antisense and control sense probes, showed signal only with the antisense probe, confirming the specificity of hybridization. Within sections of each lobe, hybridization signal was detected exclusively over the epithelial cells lining the ducts. Stromal cells did not show detectable expression of NKX3.1. There was no distinguishable difference in the intensity of the signal over epithelial cells derived from individual lobes. These observations demonstrate that NKX3.1 mRNA is confined to epithelial cells in the adult prostate and are consistent with a role for this gene in the maintenance of differentiated functions in the prostate gland.

These observation strongly implicate NKX3.1 in the differentiation of the urethral epithelium into the highly-specialized prostate epithelium. Given that the NKX3.1 protein is likely to function as a transcription factor and its expression is restricted to the prostate anlage, it seems likely that the NKX3.1 gene is playing a primary role in driving the differentiation of the prostate gland. The continued expression of this gene in all four component lobes in adult animals suggests that it may further be involved in the maintenance of this tissue.

Example 9

NXK3.1 Expression During Mouse Development

To gain insights into the potential roles of NKX3.1, its expression in embryonic and adult tissues was examined. First, RNAse protection analysis was performed using tissues obtained from late-gestation embryos and adults. Several tissues from day 17.5 p.c. embryos were surveyed and were found low levels to have of NKX3.1 expression in the kidney and developing gonad, barely detectable levels in the thyroid, and no detectable levels of expression in several other tissues examined. Given NKX3.1 expression in the developing urogenital system, tissues obtained from sexually immature (2-4 weeks old) male, sexually mature (8-12 weeks old) male, and sexually immature and mature female mice were also surveyed. NKX3.1 expression was observed in the prostate, seminal vesicle, and testis of sexually immature and mature male mice. Moreover, significantly higher levels of NKX3.1 were detected in the prostate and seminal vesicles of the sexually mature, versus immature, mice. In contrast, NKX3.1 was not detectable in tissues from the immature or mature female urogenital system.

To further verify these observations, the expression of NKX3.1 was examined by Northern blot analysis, using tissues obtained from adult male mice (8-12 weeks old). A transcript of about 3.2 kB was detected in total RNA prepared from seminal vesicle or a pooled sample of bladder and prostate, but not from several other tissues. Together with the results of RNAse protection analysis, these findings demonstrate that NKX3.1 exhibits a limited tissue distribution in the developing urogenital system, and that its expression is most elevated in sexually mature males.

Both the prostate and seminal vesicles, which express high levels of NKX3.1, require androgens for their growth and development (Cunha, G. R., *Cancer* 74:1030-1044 (1994); Cunha, G. R. et al., *Endocrine Reviews* 8:338-362 (1987)). Since expression of NKX3.1 was essentially undetectable in the prostate of castrated mice, together with results showing the human NKX3.1 is androgen-regulated in prostate carcinoma cells, these data suggest that androgen stimulation is required for maintenance of NKX3.1 expression.

Localized Expression of NKX3.1 During Murine Embryogenesis

To further delineate the expression pattern of NKX3.1 during murine embryogenesis, in situ hybridization was performed on cryosections from mouse embryos at days 14.5 through 17.5 of gestation. Based on the RNAse protection results, the analysis was focused on the development of the male urogenital system.

Materials and Methods

Isolation of RNA and analysis of expression: Tissues were obtained by dissection from male or female Swiss-Webster mice, or day 17.5 p.c. embryos and freshly frozen (−70° C.), or were purchased from Pel-Freez Biologicals, Inc. Frozen tissues from sham operated or castrated mice, at 2 days post surgery, were obtained from Taconic Farms, Inc. RNA was prepared using TRIZOL™ RNA isolation reagent (GIBCO-BRL) according to the protocol of the manufacturer. RNAse protection analysis was performed essentially as described (Krieg, P. A. and Melton, D. A., *Meth. Enzymol.* 155:397-415 (1987)) using antisense or sense riboprobes prepared from various subcloned fragments of the NKX3.1 cDNA. The antisense riboprobe specific for the L32 ribosomal protein gene was described in (Shen, M. M. and Leder, P., *Proc. Natl. Acad. Sci. USA* 89:8240-8244 (1992)). The RNAse protection assays were performed using probe A which spans the intron-exon splice junction; similar results were obtained using probes B or C. Northern blot analysis was performed essentially as described (Ausubel, F. et al., *In Current Protocols in Molecular Biology*, K. Janssen, Ed., John Wiley and Sons, Inc., New York, N.Y. (1995)) using a nylon filter membrane (Hybond-N, Amersham). Filters were prehybridized at 42° C. for 1 hour in SLURP (7 mM Tris-HCl (pH 7.5), 4×SSC, 10% dextran sulfate, 0.8×Denhardt's solution, 40% formamide, 20 mg/mL salmon sperm DNA and 0.5% SDS). Probes were labeled with $^{32}$P-dCTP by random priming (Ausubel, F. et al., *In Current Protocols in Molecular Biology*, K. Janssen, Ed., John Wiley and Sons, Inc., New York, N.Y. (1995)), and filters were hybridized overnight at 42° C. Filters were washed in 2×SSC/0.1% SDS at 42° C. for 10 min, then at room temperature for 10 min, followed by a high stringency wash in 0.2×SSC/0.1% SDS at 65° C. for 40 min.

In situ hybridization: Digoxigenin-labeled riboprobes, corresponding to regions of the Nkx3.1 cDNA (probes D, E, F) were synthesized as described (Catron, K. M. et al., *Mech. Dev.* 55:185-199 (1996)). To determine the sex of Swiss Webster mouse embryos, genomic DNA was isolated from tails and PCR was performed using primers directed against the Sry gene (Hogan, B. et al., *Manipulating the mouse embryo*, Cold Spring Harbor Laboratory Press, Cold Spring Harbor (1994)). Embryos were fixed with 4% paraformaldehyde/phosphate buffered saline (PBS) at 4° C. for two days and transferred to a solution of 30% sucrose/PBS plus 0.1% Tween (PBT), bleached with 6% $H_2O^2$/PBT, then washed three times with PBT. Sections were treated with 1 μg/ml proteinase K/PBT, followed by sequential washes with 2 mg/ml glycine/PBT and PBT. Sections were incubated in prehybridization solution (50% formamide, 5×SSC (pH 4.5), 50 μg/ml yeast tRNA, 1% SDS, 50 μg/ml heparin) at 65° C. for 1 hr. followed by hybridization with digoxigenin-labeled riboprobes overnight at 65° C. Sections were washed three times each in: 50% formamide/5×SSC (pH 4.5)/1% SDS at 70° C.; 50% formamide/5×SSC (pH 4.5) at 65° C.; Tris-HCl buffered saline/0.1% Tween(TBST)/2 mM levimasole at room temperature. Sections were then blocked in 5% sheep serum/TBST, and incubated in anti-digoxigenin-AP Fab fragment antibody (Boehringer) at 4° C. overnight. Sections were washed four times each in TBST, then in NTMT [100 mM NaCl, 100 mM Tris-HCl (pH 9.5), 50 mM $MgCl_2$, 0.1% Tween, 2 mM levimasole and developed in 4-nitro blue tetrazolium chloride/5-bromo-4-chloro-3-indolyl-phosphate, dissolved in 10% polyvinyl alcohol/NTMT for 16 hr, and subsequently mounted.

Results

The in situ hybridization results demonstrate that NKX3.1 was expressed by several sexually dimorphic tissues of the male urogenital system, as well as by non-sexually dimorphic tissues including the dorsal aorta, lung, and intestine. Interestingly, NKX3.1 is primarily expressed by tissues that are derived from the endoderm, and is often found in epithelial cells that have a secretory function.

Within the male urogenital system, expression of NKX3.1 was observed in the developing urogenital sinus at day 14.5 p.c., and in the ventral prostatic buds at day 17.5 p.c. During the development of the male urogenital system, the primitive urogenital sinus is subdivided into three regions, which give rise to the urinary bladder, the prostatic and membranous parts of the urethra, and the penile urethra. Outbuddings of the central (pelvic) region of the urogenital sinus are responsible for formation of the prostate gland at late stages of embryogenesis. Thus, at day 14.5 of gestation, NKX3.1 expression was observed in outbuddings of the pelvic region of the urogenital sinus, with lower levels of expression in the prospective urethra. Notably, expression is confined to the epithelial cells that are invaginating into the surrounding mesenchyme, with highest levels observed at the leading edge. Later, at day 17.5 p.c., expression of NKX3.1 is found in the developing ventral prostatic buds. NKX3.1 expression was also observed in the dorsolateral and anterior prostatic buds, but not in the epithelial lining of the bladder. In addition, NKX3.1 expression was also observed in the developing tests at days 14.5 and 17.5 of gestation. Expression was localized to the medullary cords, which form the seminiferous tubules, and was not observed in the interstitial mesenchyme or in the cells forming the fibrous outer layer of the testis. No expression of NKX3.1 was observed in the ductus deferens or in the epididymis.

Furthermore, NKX3.1 expression was observed in several non-sexually dimorphic tissues, such as in the endothelial cells that line the dorsal aorta at day 14.5 of gestation. Interestingly, NKX3.1 is not expressed by endothelial cells in general, but instead its expression is confined to regions of the dorsal aorta that are in proximity to the developing metanephric kidneys, as well as to the renal arteries that arise from the dorsal aorta. In other non-sexually dimorphic tissues, low-level expression of NKX3.1 was observed in the epithelial cells that line the bronchi of the lung. Finally, expression of NKX3.1 was also observed in the small intestine, where expression is localized to a limited population of cells that appear to correspond to the mucus-secreting goblet cells.

Example 10

Temporal and Spatial Pattern of NKX3.1 Expression During Embryo genesis

To gain further insight into its potential developmental functions, the expression of NKX3.1 in pregastrulation through organogenesis stage embryos (e6.5-e10.5) and at a later stage of organogenesis (e15.5) was examined. These studies have revealed an intriguing pattern of expression that is markedly different from the Hox and other known homeobox genes, and implicate NKX3.1 in the differentiation of distinct populations of epithelial cells.

Materials and Methods

A 530-base $^{35}$S-labeled antisense RNA probe derived from the 3' noncoding region of murine NKX3.1 was hybridized to serial paraffin sections of paraformaldehyde-fixed FVB/N embryos as described (Bogard et al., 1989). The corresponding sense probe used on alternating sections did not hybridize in a specific pattern.

Results

To determine the temporal and spatial pattern of expression of NKX3.1 during embryogenesis, serial sections of mouse embryos at various stages were analyzed by in situ hybridization using an antisense RNA probe derived from the 3' non-coding region of the mRNA. Analysis of sections of e6.5 and e7.5 embryos did not reveal any hybridization above background, indicating that this gene is not activated during gastrulation. Prominent expression of NKX3.1 was first detected in e8.5 embryos, and was localized to anterior paraxial mesenchyme. Mesenchyme adjacent to the developing midbrain and hindbrain expressed NKX3.1, with an apparent anterior boundary just posterior to the level of the foregut diverticulum. This head paraxial mesenchyme is the source of all voluntary muscles of the head and, in addition, makes contributions to skeletal elements, the dermis, and meninges in the chick (Noden, D. M., Am. J. Anat. 168257-276 (1983); Noden, D. M., Develop. Biol. 96:144-165 (1983)). Compared to somites which are patterned in large measure by Hox genes, little is known about the genetic mechanisms that specify the fate of anterior paraxial mesenchyme. Expression of NKX3.1 in this tissue provides the first insight into potential pathways to determine cell specification in this tissue.

Expression of NKX3.1 was also seen in more mature anterior somites in e8.5 embryos, while newly-condensed somites and the unsegmented presomitic mesoderm did not show hybridization signal. This pattern of expression suggests that NKX3.1 is activated in a cranio-caudal sequence, in an manner that parallels somite differentiation. Within the labeled somites, expression was not uniform, but was restricted to the ventral region. The onset of NKX3.1 expression in somites correlated well with the compartmentalization of the epithelial somite into the dermamyotome, which initially retains an epithelial arrangement, and the sclerotome, which is clearly distinguishable by the mesenchymal phenotype of its cells, with NKX3.1 being confined to sclerotomal cells. This spatiotemporal pattern of expression is distinct from that of the Hox genes which are activated first in presomitic mesoderm, with expression spreading anteriorly to a discrete somitic boundary (Krumlauf, R., Cell 78:191-201 (1994)). The contrasting patterns of Hox versus NKX3.1 expression in somites likely reflect different functions for these genes in the differentiation of paraxial mesoderm. The regionally-restricted, overlapping patterns of Hox gene expression may form the basis of a molecular "code" that is translated into specific vertebral phenotypes (Kessel and Gruss, 1991). Patterning functions attributed to Hox genes, such as growth of ribs, have been suggested based on transplant studies to be established prior to the onset of overt segmentation into somites (Kieny et al., *Develop. Biol.* 28:142-161 (1972)). On the other hand, NKX3.1 may have a more general function in somite differentiation, for example by conferring a mesenchymal phenotype on somitic cells. The division of the somite into sclerotome and dermamyotome is an essential step in vertebral development that may be regulated by NKX3.1.

The pattern of expression at e9.5 was similar to that observed in e8.5 embryos. NKX3.1 mRNA continued to be expressed in the unsegmented paraxial mesenchyme anterior to the region of somite formation, but at a reduced level compared to e8.5, and in the sclerotome of differentiating somites. An anteroposterior gradient of expression was apparent in somites, with the more mature anterior somites showing less signal than those more posterior and just beginning to undergo differentiation. Highest levels of NKX3.1 expression appeared to correlate with early stages of sclerotome development, and expression was clearly absent from the dermamyotome. The down-regulation of NKX3.1 in more mature somites also argues for an early function in somite differentiation.

Analysis of e10.5 embryos revealed continued NKX3.1 expression in sclerotomal cells and head mesenchyme, as well as several new sites, most notably the axial mesenchyme. The axial mesenchyme consists of a loose meshwork of cells surrounding the notochord, directly beneath the neural tube, and is histologically distinct from the more dense paraxial mesenchyme from which somites derive (Verbout, A. J., "Advances in anatomy, embryology and cell biology," in *The Development of the Vertebral Column*, Vol. 90, Springer-Verlag, New York (1985)). NKX3.1 expression was observed in axial mesenchyme along the entire anteroposterior axis. Although these cells are contiguous with the sclerotomal cells, they are morphologically distinct, prompting the suggestion of different embryonic origins (Dawes, B., *Mus Musculus. philos. Trans. R. Soc. Lond. [Biol.]* 218:115-170 (1931)). More recent authors have argued for a common somitic origin for sclerotomal and axial mesenchyme, based solely on histologic criteria (Verbout, A. J., "Advances in anatomy, embryology and cell biology," in *The Development of the Vertebral Column*, Vol. 90, Springer-Verlag, New York (1985)). Detection of NKX3.1 mRNA in both cell populations strongly supports the latter hypothesis by providing a genetic link between the two. NKX3.1 may play a role in specifying an axial mesenchyme fate in differentiating somitic cells.

A second new site of expression seen in e10.5 embryos is the wall of the abdominal aorta. The abdominal aorta develops in close apposition to the axial mesenchyme. In fact, there is no clear morphologic boundary which separates sclerotome, axial mesenchyme, and the wall of the aorta (Verbout, A. J., "Advances in anatomy, embryology and cell biology," in *The Development of the Vertebral Column*, Vol. 90, Springer-Verlag, New York (1985)). Scattered cells along the length of the abdominal aorta expressed NKX3.1 with an apparent anterior boundary just caudal to the level of the heart. These cells could represent axial mesenchymal cells that have been recruited to participate in vessel wall formation. Although the embryonic origin of endothelial cells has been well-characterized, the origin of vascular smooth muscle cells in developing vessels is poorly-defined and no markers that identify precursor cells have been reported (Owens, G. K., *Physiol. Rev.* 75:487-509 (1995)). NKX3.1 may represent an early marker of vascular smooth muscle cell differentiation in the abdominal aorta.

By e15.5, expression of NKX3.1 in somitic derivatives was no longer detectable. However, strong expression was observed in the abdominal aorta and in the developing renal vasculature. Although the limited cellular resolution of in situ hybridization precludes an unequivocal interpretation, NKX3.1 appears to be absent from the endothelial lining of the aorta. Immunostaining to detect smooth muscle $\alpha$-actin, an early marker of smooth muscle cell differentiation (Owens, G. K., *Physiol. Rev.* 75:487-509 (1995)), revealed a perfect overlap with expression of NKX3.1 in these vessels in serial sections. Based on these observations, it appears that NKX3.1 is involved in specifying a smooth muscle cell phenotype in cells recruited from the axial mesenchyme into the wall of the aorta. Expression in the wall of the aorta was stronger posterior and faded out towards the heart. Consistent with our observations on e10.5 embryos, NKX3.1 was not detected in vessels anterior to the level of the heart.

Prominent expression of NKX3.1 was also detected in the developing incisors and molars in e15.5 embryos. The first evidence of tooth development is a thickening of the oral epithelium detectable in e12.5 embryos (Cohn, S. A., *Am. J. Anat.* 101:295-320 (1957)). This dental lamina develops into an epithelial bud that becomes surrounded by mesenchymal cells derived from the neural crest that constitute the dental papilla. By e15.5, invaginations of the dental lamina mark the beginning of the cap stage of development. The dental lamina also begins to differentiate into two distinct layers, the inner and outer enamel layers. NKX3.1 is expressed predominantly in the deep invaginations of the dental lamina at the junction between the inner and outer enamel layers. The surrounding mesenchyme of the dental papilla did not express NKX3.1. This restricted pattern of expression in the developing teeth suggests that NKX3.1 is involved in regional differentiation of cells within the dental epithelium.

The presence of a homeobox in the coding region of NKX3.1 provides presumptive evidence that this gene encodes a transcription factor that, by analogy to other homeodomain proteins, likely regulates genes involved in establishing a specific state of cellular differentiation. The onset of expression of NKX3.1 in somites seems to occur in concert with the transition from an entirely epithelial structure to one with two morphologically distinct components; it is possible that NKX3.1 may regulate the epithelial to mesenchymal transition that gives rise to the sclerotomal cell population where it is expressed. The observation of NKX3.1 expression in axial mesoderm and the wall of the abdominal aorta may indicate that NKX3.1 is involved in directing a subset of somitic cells toward a particular cell fate. The distribution of NKX3.1 in specific regions of developing teeth is also consistent with a role in the commitment of epithelial cells.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated antibody that specifically binds a NKX3.1 protein having an amino acid sequence consisting of either amino acid residues 1 to 234 in SEQ ID NO:2 or amino acid residues 124 to 183 in SEQ ID NO:2.

2. The antibody of claim 1 wherein said NKX3.1 protein has an amino acid sequence consisting of amino acid residues 1 to 234 in SEQ ID NO:2.

3. The antibody of claim 1 wherein said NKX3.1 protein has an amino acid sequence consisting of amino acid residues 124 to 234 in SEQ ID NO:2.

4. The antibody of claim 2 wherein said antibody specifically binds a NKX3.1 protein having an amino acid sequence consisting of amino acid residues 124 to 234 in SEQ ID NO:2.

5. The antibody of claim 3, wherein said protein bound by said antibody is glycosylated.

6. The antibody of claim 3, wherein said antibody is monoclonal.

7. The antibody of claim 3, wherein said antibody is polyclonal.

8. The antibody of claim 3 that is labeled.

9. The antibody of claim 3, wherein said antibody specifically binds to said protein in a Western blot or an Enzyme Linked Immunosorbent Assay (ELISA).

10. An isolated cell that produces the antibody of claim 3.

11. A method of detecting NKX3.1 protein in a biological sample comprising:
(a) contacting the biological sample, a positive control sample and a negative control sample with the antibody of claim 3; and
(b) detecting the binding of the antibody to said samples; wherein the detection of binding to the biological sample and positive control sample, but not to the negative control sample, is indicative of the presence of the NKX3.1 protein in the biological sample.

12. An isolated antibody that specifically binds a NKX3.1 protein purified from a cell culture, wherein said NKX3.1 protein is encoded by a polynucleotide encoding amino acids residues 1 to 234 of SEQ ID NO:2.

13. The antibody of claim 12, wherein said antibody is monoclonal.

14. The antibody of claim 12, wherein said antibody is polyclonal.

15. The antibody of claim 12, wherein said antibody specifically binds to said protein in a Western blot or an ELISA.

16. The antibody of claim 12, wherein the amino acid sequence of said NKX3.1 protein consists of amino acids residues 124 to 183 of SEQ ID NO:2.

* * * * *

SEQUENCE LISTING (1) GENERAL INFORMATION:

(iii) NUMBER OF SEQUENCES: 30

(2) INFORMATION FOR SEQ ID NO: 1:

(i) SEQUENCE CHARACTERISTICS:
       (A) LENGTH: 705 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 1:

```
ATGCTCAGGG TTCCGGAGCC GCGGCCCGGG GAGGCGAAAG CGGAGGGGGC CGCGCCGCCG    60

ACCCCGTCCA AGCCGCTCAC GTCCTTCCTC ATCCAGGACA TCCTGCGGGA CGGCGCGCAG   120

CGGCAAGGCG CCGCACGAG CAGCCAGAGA CAGCGCGACC CGGAGCCGGA GCCAGAGCCA   180

GAGCCAGAGG GAGGACGCAG CCGCGCCGGG GCGCAGAACG ACCAGCTGAG CACCGGGCCC   240

CGCGCCGCGC CGGAGGAGGC CGAGACGCTG GCAGAGACCG AGCCAGAAAG GCACTTGGGG   300

TCTTATCTGT TGGACTCTGA AAACACTTCA GGCGCCCTTC CAAGGCTTCC CCAAACCCCT   360

AAGCAGCCGC AGAAGCGCTC CCGAGCTGCC TTCTCCCACA CTCAGGTGAT CGAGTTGGAG   420

AGGAAGTTCA GCCATCAGAA GTACCTGTCG GCCCCTGAAC GGGCCCACCT GGCCAAGAAC   480

CTCAAGCTCA CGGAGACCCA AGTGAAGATA TGGTTCCAGA ACAGACGCTA TAAGACTAAG   540

CGAAAGCAGC TCTCCTCGGA GCTGGGAGAC TTGGAGAAGC ACTCCTCTTT GCCGGCCCTG   600

AAAGAGGAGG CCTTCTCCCG GCCTCCCTG GTCTCCGTGT ATAACAGCTA TCCTTACTAC   660

CCATACCTGT ACTGCGTGGG CAGCTGGAGC CCAGCTTTTG GGTAA                   705
```

(2) INFORMATION FOR SEQ ID NO: 2:

(i) SEQUENCE CHARACTERISTICS:
       (A) LENGTH: 234 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 2:

```
Met Leu Arg Val Pro Glu Pro Arg Pro Gly Glu Ala Lys Ala Glu Gly
1               5                   10                  15

Ala Ala Pro Pro Thr Pro Ser Lys Pro Leu Thr Ser Phe Leu Ile Gln
                20                  25                  30

Asp Ile Leu Arg Asp Gly Ala Gln Arg Gln Gly Gly Arg Thr Ser Ser
                35                  40                  45

Gln Arg Gln Arg Asp Pro Glu Pro Glu Pro Glu Pro Glu Pro Glu Gly
            50                  55                  60

Gly Arg Ser Arg Ala Gly Ala Gln Asn Asp Gln Leu Ser Thr Gly Pro
65                  70                  75                  80

Arg Ala Ala Pro Glu Glu Ala Glu Thr Leu Ala Glu Thr Glu Pro Glu
                85                  90                  95

Arg His Leu Gly Ser Tyr Leu Leu Asp Ser Glu Asn Thr Ser Gly Ala
                100                 105                 110

Leu Pro Arg Leu Pro Gln Thr Pro Lys Gln Pro Gln Lys Arg Ser Arg
```

-continued

```
            115                 120                 125
Ala Ala Phe Ser His Thr Gln Val Ile Glu Leu Glu Arg Lys Phe Ser
    130                 135                 140

His Gln Lys Tyr Leu Ser Ala Pro Glu Arg Ala His Leu Ala Lys Asn
145                 150                 155                 160

Leu Lys Leu Thr Glu Thr Gln Val Lys Ile Trp Phe Gln Asn Arg Arg
                165                 170                 175

Tyr Lys Thr Lys Arg Lys Gln Leu Ser Ser Glu Leu Gly Asp Leu Glu
            180                 185                 190

Lys His Ser Ser Leu Pro Ala Leu Lys Glu Glu Ala Phe Ser Arg Ala
        195                 200                 205

Ser Leu Val Ser Val Tyr Asn Ser Tyr Pro Tyr Tyr Pro Tyr Leu Tyr
    210                 215                 220

Cys Val Gly Ser Trp Ser Pro Ala Phe Gly
225                 230
```

(2) INFORMATION FOR SEQ ID NO: 3:

(i) SEQUENCE CHARACTERISTICS:
       (A) LENGTH: 705 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 3:

```
ATGCTCAGGG TTCCGGAGCC GCGGCCCGGG GAGGCGAAAG CGGAGGGGGC CGCGCCGCCG     60

ACCCCGTCCA AGCCGCTCAC GTCCTTCCTC ATCCAGGACA TCCTGCGGGA CGGCGCGCAG    120

CGGCAAGGCG GCCGCACGAG CAGCCAGAGA CAGTGCGACC CGGAGCCGGA GCCAGAGCCA    180

GAGCCAGAGG GAGGACGCAG CCGCGCCGGG GCGCAGAACG ACCAGCTGAG CACCGGGCCC    240

CGCGCCGCGC CGGAGGAGGC CGAGACGCTG GCAGAGACCG AGCCAGAAAG GCACTTGGGG    300

TCTTATCTGT TGGACTCTGA AAACACTTCA GGCGCCCTTC CAAGGCTTCC CCAAACCCCT    360

AAGCAGCCGC AGAAGCGCTC CCGAGCTGCC TTCTCCCACA CTCAGGTGAT CGAGTTGGAG    420

AGGAAGTTCA GCCATCAGAA GTACCTGTCG CCCCTGAAC GGGCCCACCT GGCCAAGAAC     480

CTCAAGCTCA CGGAGACCCA AGTGAAGATA TGGTTCCAGA ACAGACGCTA TAAGACTAAG    540

CGAAAGCAGC TCTCCTCGGA GCTGGGAGAC TTGGAGAAGC ACTCCTCTTT GCCGGCCCTG    600

AAAGAGGAGG CCTTCTCCCG GGCCTCCCTG GTCTCCGTGT ATAACAGCTA TCCTTACTAC    660

CCATACCTGT ACTGCGTGGG CAGCTGGAGC CCAGCTTTTG GGTAA                   705
```

(2) INFORMATION FOR SEQ ID NO: 4:

(i) SEQUENCE CHARACTERISTICS:
       (A) LENGTH: 234 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 4:

```
Met Leu Arg Val Pro Glu Pro Arg Pro Gly Glu Ala Lys Ala Glu Gly
1               5                   10                  15

Ala Ala Pro Pro Thr Pro Ser Lys Pro Leu Thr Ser Phe Leu Ile Gln
            20                  25                  30
```

```
Asp Ile Leu Arg Asp Gly Ala Gln Arg Gln Gly Gly Arg Thr Ser Ser
            35                  40                  45

Gln Arg Gln Cys Asp Pro Glu Pro Glu Pro Glu Pro Glu Pro Glu Gly
 50                  55                  60

Gly Arg Ser Arg Ala Gly Ala Gln Asn Asp Gln Leu Ser Thr Gly Pro
 65                  70                  75                  80

Arg Ala Ala Pro Glu Glu Ala Glu Thr Leu Ala Glu Thr Glu Pro Glu
                 85                  90                  95

Arg His Leu Gly Ser Tyr Leu Leu Asp Ser Glu Asn Thr Ser Gly Ala
                100                 105                 110

Leu Pro Arg Leu Pro Gln Thr Pro Lys Gln Pro Gln Lys Arg Ser Arg
            115                 120                 125

Ala Ala Phe Ser His Thr Gln Val Ile Glu Leu Glu Arg Lys Phe Ser
130                 135                 140

His Gln Lys Tyr Leu Ser Ala Pro Glu Arg Ala His Leu Ala Lys Asn
145                 150                 155                 160

Leu Lys Leu Thr Glu Thr Gln Val Lys Ile Trp Phe Gln Asn Arg Arg
                165                 170                 175

Tyr Lys Thr Lys Arg Lys Gln Leu Ser Ser Glu Leu Gly Asp Leu Glu
            180                 185                 190

Lys His Ser Ser Leu Pro Ala Leu Lys Glu Glu Ala Phe Ser Arg Ala
            195                 200                 205

Ser Leu Val Ser Val Tyr Asn Ser Tyr Pro Tyr Pro Tyr Leu Tyr
            210                 215                 220

Cys Val Gly Ser Trp Ser Pro Ala Phe Gly
225                 230

(2) INFORMATION FOR SEQ ID NO: 5:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

Lys Lys Arg Ser Arg Ala Ala Phe Ser His Ala Gln Val Phe Glu Leu
 1               5                  10                  15

Glu Arg Arg Phe Ala Gln Gln Arg Tyr Leu Ser Gly Pro Glu Arg Ser
                20                  25                  30

Glu Met Ala Lys Ser Leu Arg Leu Thr Glu Thr Gln Val Lys Ile Trp
            35                  40                  45

Phe Gln Asn Arg Arg Tyr Lys Thr Lys Arg Lys Gln
 50                  55                  60

(2) INFORMATION FOR SEQ ID NO: 6:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

Lys Lys Arg Lys Arg Arg Val Leu Phe Thr Lys Ala Gln Thr Tyr Glu
 1               5                  10                  15
```

Leu Glu Arg Arg Phe Arg Gln Gln Arg Tyr Leu Ser Ala Pro Glu Arg
            20                  25                  30

Glu His Leu Ala Ser Leu Ile Arg Leu Thr Pro Thr Gln Val Lys Ile
            35                  40                  45

Trp Phe Gln Asn His Arg Tyr Lys Thr Lys Arg Ala
50                  55                  60

(2) INFORMATION FOR SEQ ID NO: 7:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

Lys Arg Lys Pro Arg Val Leu Phe Ser Gln Ala Gln Val Leu Glu Leu
1               5                   10                  15

Glu Cys Arg Phe Arg Leu Lys Lys Tyr Leu Thr Gly Ala Glu Arg Glu
            20                  25                  30

Ile Ile Ala Gln Lys Leu Asn Leu Ser Ala Thr Gln Val Lys Ile Trp
            35                  40                  45

Phe Gln Asn Arg Arg Tyr Lys Ser Lys Arg Gly Asp
50                  55                  60

(2) INFORMATION FOR SEQ ID NO: 8:

(i) SEQUENCE CHARACTERISTICS:
        (A) LENGTH: 3488 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 8:

```
AATTAACCCT CACTAAAGGG AACAAAAGCT GGAGCTCCAC CGCGGTGGCG GCCGCGTAAT      60

ACGACTCACT ATAGGGCGAA GAATTCGGAT CTATCAATCT GCATCCTTGT TTCAGAACCA     120

TTTGATGTAA GTTTCATAAA TCTTGTGCCT TTGCTCCTAC TTACTTCAGT GTTTATTTCC     180

TAAAAATATT CTCTTGTACA CTGACAGTAC AATGTGCAAT TCAGTAAAT TTAACATTAA      240

TTCAATACTT CCATCATCGA CCTGACACTG AGACTCATGC CTGTAGTCCT GGCACTTTGA     300

GAGGCCAAGG CAGGAGGATC ACTTGAATCC AGGAAATCGA GGCTGCAGTG AGTTATGATG     360

GCATCACTGC ACTCCAGCCT GGGCGGCAGA GGGAGACCCT GTCCGTAAAA AACAGAAGAG     420

AAAAGACAAG GAAAGAAAAT ACTTCCATCA TCTCTGTTCC ACTTTCGTCT GTTGTCACGG     480

TACCGTCCAG TCCAGTCACA GTACCGGTTG GACCAATCTG GCTAACCCAT TGTTTAGCCA     540

ATGGGTTACA TGTTAACAGT TGGTAATCTG CAAAAAGAGT ATGCTGATGT TCTTTTGAAC     600

TACTTTTTTA AATGCAGTTT TTGCATTTGT CCCTGGCCTA AAACGCCTTC CATCCGTCTG     660

GAAACTTTTC AAAAGGATGG TATGTCATGT GTCTGGGAG GAAGGAAAGT TAACAGGTTA      720

TTGCGGATAA AGGAACCACC AAAGAAAACC ACTTCTGCAA CGGGAAAAGG CTTTGGCAAA     780

GGTGTTTTCC TTCTTTCAGC CTGGGGTCTG GCTGCACCTA CTTGTCATGC CTCTTTGAGG     840

TCGTAGATAT TGCAGATCTG AGTTTGCACC ATCTCTCCCA GAGAGAGAGA GCACCCAGAA     900

CTCTCACGGT ACCGCGCGGC TGCAGTGACT GCGTGCTCAT CCCCTGTAAT TGGCTCTGAC     960
```

```
GGTCCTGAAG AGCTAACTGG ACTGTTTGTC TTGATCGTCC CATCCCCAGG AGCTTCTCTC    1020
TGCTGCGGGT GGGTTGGGGC AGAGGAGCCC CGCTTTGGGG TGCGCTCCTG GCCTGGGAAA    1080
ACGGCTCAGG GCGGAGGGAG GAGAGCTGGA GAAGGAGAGG AAATTGGGGA AGGAGAGGGA    1140
ATTGGGGAAG GAGAGGGAAC TGGGGAAGGA ATCCCCTAGG GAGGAGCGGA GCGGGGCAGT    1200
GCTCAGGGCT CGCAGATCGG CGGGGTCACC TGGGGCTCAG GGCGGCCAAT CCGCGGCGCG    1260
GCCCGTCCCG CGGCCAATGG GAGGGCGGCG CGGCCCGCTC CCCTGGGCTA TAAGCGAGCC    1320
GGGAGGCGGA AAGTGAAAGC GGTGCGGGCC GGGCGGGTGC ATTCAGGCCA AGGCGGGGCC    1380
GCCGGGATGC TCAGGGTTCC GGAGCCGCGG CCCGGGGAGG CGAAAGCGGA GGGGGCCGCG    1440
CCGCCGACCC CGTCCAAGCC GCTCACGTCC TTCCTCATCC AGGACATCCT GCGGGACGGC    1500
GCGCAGCGGC AAGGCGGCCG CACGAGCAGC CAGAGACAGC GCGACCCGGA GCCGGAGCCA    1560
GAGCCAGAGC CAGAGGGAGG ACGCAGCCGC GCCGGGGCGC AGAACGACCA GCTGAGCACC    1620
GGGCCCCGCG CCGCGCCGGA GGAGGCCGAG ACGCTGGCAG AGACCGAGCC AGGTAAGCGG    1680
CGAGGCCGGG GAAGGGGGGC AGCCCAAGGC GGACCCCCAG AGCTCGGGGT GCAGGGACGC    1740
GGGGCTCCGC GGCGACAGGC AGAGGGACCT TCCCGCCTCC GCAGCCACGC GCGCGCCCCC    1800
GGAATGAACC CTGAGCCCCA GCGTCAGGGC GGCGCAGGAT TCTGACACCG CAGGATTCGC    1860
CCGGTTCCGT GCCTTCCGTT CCCTGGGGCT CAGAAGCCGG CGCGACTGCA GCGCCACCGC    1920
CTTCCACCGT CCCAGGAGCG GATCCCGCCC CGCGCCACCC GCGATCGGCG CCAGCCCCCC    1980
GGTAGTTATG AGAANTAATA ATAACTTATT AACAGTGACA AGCAGGGGT TGACCAGCAA    2040
AGCCTCCGTG TGCTTCCCAA TCCCGTGGGC AGTAAAGCGG TATATTCGGG GTTCCCTCCG    2100
GTGTCCAGGA GAGAGAGTCC ACTTATTTTC TTTCCTGTCA CTTCTGATGA GGCGACCGAA    2160
CGCCTCGTTT AGCGAAGAGG GAATTAAAGC CCAGAATGAG CCTGCCTCTG CGTCTCCAGT    2220
GGCACAAGCC CTCTCTTGCC CACCTGGATC CTAACACCGG ATGTCTTTTG GTCTGGCCTT    2280
CCCGGGTATC TTGTTCCACG GCATTTTCCC TGCCTCCCTC TCCCGCCTCT CCTCAGCACA    2340
CAGATCCAGA ATCCCCATAT AATTCTACTA GACAGTAGGG AGAAAGTTCA ACCACGAAAC    2400
GTCTCTAACT TTGGGTTCTT GATGATTCTT AGCAAATGAA TGCGTAATAA ACATATTTAC    2460
TCACTCTTCA CTCCGGAGAG CTCCTTAGTC ATGTGAAAAA AGTGAAATGT ATCCACGATG    2520
ACAGTGGGCT GTTTGTTCAC TCACTAAAGA GATAAGGGTG GATTGAATTC TCTTCTCTTC    2580
CCTGCTAACA TGTAACTTTT GTCTTCCCAT CCCTCCTTCC CCACTCTCCT TTCCAGAAAG    2640
GCACTTGGGG TCTTATCTGT TGGACTCTGA AAACACTTCA GGCGCCCTTC CAAGGCTTCC    2700
CCAAACCCCT AAGCAGCCGC AGAAGCGCTC CCGAGCTGCC TTCTCCCACA CTCAGGTGAT    2760
CGAGTTGGAG AGGAAGTTCA GCCATCAGAA GTACCTGTCG GCCCCTGAAC GGGCCCACCT    2820
GGCCAAGAAC CTCAAGCTCA CGGAGACCCA AGTGAAGATA TGGTTCCAGA ACAGACGCTA    2880
TAAGACTAAG CGAAAGCAGC TCTCCTCGGA GCTGGGAGAC TTGGAGAAGC ACTCCTCTTT    2940
GCCGGCCCTG AAAGAGGAGG CCTTCTCCCG GGCCTCCCTG GTCTCCGTGT ATAACAGCTA    3000
TCCTTACTAC CCATACCTGT ACTGCGTGGG CAGCTGGAGC CCAGCTTTTG GGTAATGCCA    3060
GCTCAGGTGA CAACCATTAT GATCAAAAAC TGCCTTCCCC AGGGTGTCTC TATGAAAAGC    3120
ACAAGGGGCC AAGGTCAGGG AGCAAGAGGT GTGCACACCA AAGCTATTGG AGATTTGCGT    3180
GGAAATCTCA GATTCTTCAC TGGTGAGACA ATGAAACAAC AGAGACAGTG AAAGTTTTAA    3240
TACCTAAGTC ATTCCTCCAG TGCATACTGT AGGTCATTTT TTTTGGTTCT GGCTACCTGT    3300
```

```
TTGAAGGGGA GAGAGGGAAA ATCAAGTGGT ATTTTCCAGC ACTTTGTATG ATTTTGGATG    3360

AGTTGTACAC CCAAGGATTC TGTTATGCAA CTCCATCCTC CTGTGTCACT GAATATCAAC    3420

TCTGAAAGAG CAAACCTAAC AGGAGAAAGG ACAACCAGGA TGAGGATGTC ACCAACTGAA    3480

TTAAACTC                                                             3488
```

(2) INFORMATION FOR SEQ ID NO: 9:

(i) SEQUENCE CHARACTERISTICS:
        (A) LENGTH: 124 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

```
Met Leu Arg Val Ala Glu Pro Arg Glu Pro Arg Val Glu Ala Gly Gly
1               5                   10                  15

Arg Ser Pro Trp Ala Ala Pro Pro Thr Gln Ser Lys Arg Leu Thr Ser
            20                  25                  30

Phe Leu Ile Gln Asp Ile Leu Arg Asp Arg Ala Glu Arg His Gly Gly
        35                  40                  45

His Ser Gly Asn Pro Gln His Ser Pro Asp Pro Arg Arg Asp Ser Ala
    50                  55                  60

Pro Glu Pro Asp Lys Ala Gly Gly Arg Gly Val Ala Pro Glu Asp Pro
65                  70                  75                  80

Pro Ser Ile Arg His Ser Pro Ala Glu Thr Pro Thr Glu Pro Glu Ser
                85                  90                  95

Asp Ala His Phe Glu Thr Tyr Leu Leu Asp Cys Glu His Asn Pro Gly
            100                 105                 110

Asp Leu Ala Ser Ala Pro Gln Val Thr Lys Gln Pro
        115                 120
```

(2) INFORMATION FOR SEQ ID NO: 10:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

```
Met Leu Arg Val Pro Glu Pro Arg Pro Gly Glu Ala Lys Ala Glu Gly
1               5                   10                  15

Ala Ala Pro Pro Thr Pro Ser Lys Pro Leu Thr Ser Phe Leu Ile Asp
            20                  25                  30

Ile Leu Arg Asp Gly Ala Gln Arg Gln Gly Gly Arg Thr Ser Ser Gln
        35                  40                  45

Arg Gln Cys Asp Pro Glu Pro Glu Pro Glu Pro Glu Pro Glu Gly Gly
    50                  55                  60

Arg Ser Arg Ala Gly Ala Gln Asn Asp Gln Leu Ser Thr Gly Pro Arg
65                  70                  75                  80

Ala Ala Pro Glu Glu Ala Glu Thr Leu Ala Glu Thr Glu Pro Glu Arg
                85                  90                  95

His Leu Gly Ser Tyr Leu Leu Asp Ser Glu Asn Thr Ser Gly Ala Leu
            100                 105                 110
```

```
Pro Arg Leu Pro Gln Thr Pro Lys Gln Pro
        115                 120

(2) INFORMATION FOR SEQ ID NO: 11:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11:

Gln Lys Arg Ser Arg Ala Ala Phe Ser His Thr Gln Val Ile Glu Leu
1               5                   10                  15

Glu Arg Lys Phe Ser His Gln Lys Tyr Leu Ser Ala Pro Glu Arg Ala
                20                  25                  30

His Leu Ala Lys Asn Leu Lys Leu Thr Glu Thr Gln Val Lys Ile Trp
            35                  40                  45

Phe Gln Asn Arg Arg Tyr Lys Thr Lys Arg Lys Gln
    50                  55                  60

(2) INFORMATION FOR SEQ ID NO: 12:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 12:

Gln Lys Arg Ser Arg Ala Ala Phe Ser His Thr Gln Val Ile Glu Leu
1               5                   10                  15

Glu Arg Lys Phe Ser His Gln Lys Tyr Leu Ser Ala Pro Glu Arg Ala
                20                  25                  30

His Leu Ala Lys Asn Leu Lys Leu Thr Glu Thr Gln Val Lys Ile Trp
            35                  40                  45

Phe Gln Asn Arg Arg Tyr Lys Thr Lys Arg Lys Gln
    50                  55                  60

(2) INFORMATION FOR SEQ ID NO: 13:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 13:

Leu Ser Glu Asp Leu Gly Val Leu Glu Lys Asn Ser Pro Leu Ser Leu
1               5                   10                  15

Pro Ala Leu Lys Asp Asp Ser Leu Pro Ser Thr Ser Leu Val Ser Val
                20                  25                  30

Tyr Thr Ser Tyr Pro Tyr Tyr Pro Tyr Leu Tyr Cys Leu Gly Ser Trp
            35                  40                  45

His Pro Ser Phe Trp
    50
```

(2) INFORMATION FOR SEQ ID NO: 14:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 14:

Leu Ser Ser Glu Leu Gly Asp Leu Glu Lys His Ser Ser Leu Pro Ala
1               5                   10                  15

Leu Lys Glu Glu Ala Phe Ser Arg Ala Ser Leu Val Ser Val Tyr Asn
            20                  25                  30

Ser Tyr Pro Tyr Tyr Pro Tyr Leu Tyr Cys Val Gly Ser Trp Ser Pro
        35                  40                  45

Ala Phe Gly
    50

(2) INFORMATION FOR SEQ ID NO: 15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

GCGGGATCCA TGCTCAGGGT TCCGGAG                                    27

(2) INFORMATION FOR SEQ ID NO: 16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

GCGAGCTTTT ACCCAAAAGC TGGGCT                                     26

(2) INFORMATION FOR SEQ ID NO: 17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GCGGGATCCC ATGCTCAGGG TTCCGGAG                                   28

(2) INFORMATION FOR SEQ ID NO: 18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

GCGGATCCTT ACCCAAAAGC TGGGCT                                       26

(2) INFORMATION FOR SEQ ID NO: 19:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 19:

GCGGATCCTT ACCCAAAAGC TGGGCT                                       26

(2) INFORMATION FOR SEQ ID NO: 20:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 20:

CACTGCCCAG TCAAGTGTTC TTGA                                         24

(2) INFORMATION FOR SEQ ID NO: 21:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 21:

CACTGCCCAG TCACGTGTTC GTGA                                         24

(2) INFORMATION FOR SEQ ID NO: 22:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 22:

ACACTAATTG GAGGC                                                   15

(2) INFORMATION FOR SEQ ID NO: 23:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 23:

ACACTACTTG GAGGC                                                   15

(2) INFORMATION FOR SEQ ID NO: 24:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

```
CTCTAATGGC TTTTTTCTC                                              19
```

(2) INFORMATION FOR SEQ ID NO: 25:

(i) SEQUENCE CHARACTERISTICS:
        (A) LENGTH: 3974 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 25:

```
GGTACCTAAG TGAGTAGGGC GTCCGATCGA CGGACGCCTT TTTTTTGAAT TCGTAATCAT    60
GGTCATAGCT GTTTCCTGTG TGAAATTGTT ATCCGCTCAC AATTCCACAC AACATACGAG   120
CCGGAAGCAT AAAGTGTAAA GCCTGGGGTG CCTAATGAGT GAGCTAACTC ACATTAATTG   180
CGTTGCGCTC ACTGCCCGCT TTCCAGTCGG GAAACCTGTC GTGCCAGCTG CATTAATGAA   240
TCGGCCAACG CGCGGGGAGA GGCGGTTTGC GTATTGGGCG CTCTTCCGCT TCCTCGCTCA   300
CTGACTCGCT GCGCTCGGTC GTTCGGCTGC GGCGAGCGGT ATCAGCTCAC TCAAAGGCGG   360
TAATACGGTT ATCCACAGAA TCAGGGGATA ACGCAGGAAA GAACATGTGA GCAAAAGGCC   420
AGCAAAAGGC CAGGAACCGT AAAAAGGCCG CGTTGCTGGC GTTTTTCCAT AGGCTCCGCC   480
CCCCTGACGA GCATCACAAA AATCGACGCT CAAGTCAGAG GTGGCGAAAC CCGACAGGAC   540
TATAAAGATA CCAGGCGTTT CCCCCTGGAA GCTCCCTCGT GCGCTCTCCT GTTCCGACCC   600
TGCCGCTTAC CGGATACCTG TCCGCCTTTC TCCCTTCGGG AAGCGTGGCG CTTTCTCATA   660
GCTCACGCTG TAGGTATCTC AGTTCGGTGT AGGTCGTTCG CTCCAAGCTG GGCTGTGTGC   720
ACGAACCCCC CGTTCAGCCC GACCGCTGCG CCTTATCCGG TAACTATCGT CTTGAGTCCA   780
ACCCGGTAAG ACACGACTTA TCGCCACTGG CAGCAGCCAC TGGTAACAGG ATTAGCAGAG   840
CGAGGTATGT AGGCGGTGCT ACAGAGTTCT TGAAGTGGTG GCCTAACTAC GGCTACACTA   900
GAAGAACAGT ATTTGGTATC TGCGCTCTGC TGAAGCCAGT TACCTTCGGA AAAAGAGTTG   960
GTAGCTCTTG ATCCGGCAAA CAAACCACCG CTGGTAGCGG TGGTTTTTTT GTTTGCAAGC  1020
AGCAGATTAC GCGCAGAAAA AAAGGATCTC AAGAAGATCC TTTGATCTTT TCTACGGGGT  1080
CTGACGCTCA GTGGAACGAA AACTCACGTT AAGGGATTTT GGTCATGAGA TTATCGTCGA  1140
CAATTCGCGC GCGAAGGCGA AGCGGCATGC ATTTACGTTG ACACCATCGA ATGGTGCAAA  1200
ACCTTTCGCG GTATGGCATG ATAGCGCCCG GAAGAGAGTC AATTCAGGGT GGTGAATGTG  1260
AAACCAGTAA CGTTATACGA TGTCGCAGAG TATGCCGGTG TCTCTTATCA GACCGTTTCC  1320
CGCGTGGTGA ACCAGGCCAG CCACGTTTCT GCGAAAACGC GGGAAAAAGT GGAAGCGGCG  1380
ATGGCGGAGC TGAATTACAT TCCCAACCGC GTGGCACAAC AACTGGCGGG CAAACAGTCG  1440
TTGCTGATTG GCGTTGCCAC CTCCAGTCTG GCCCTGCACG CGCCGTCGCA AATTGTCGCG  1500
```

-continued

```
GCGATTAAAT CTCGCGCCGA TCAACTGGGT GCCAGCGTGG TGGTGTCGAT GGTAGAACGA    1560

AGCGGCGTCG AAGCCTGTAA AGCGGCGGTG CACAATCTTC TCGCGCAACG CGTCAGTGGG    1620

CTGATCATTA ACTATCCGCT GGATGACCAG GATGCCATTG CTGTGGAAGC TGCCTGCACT    1680

AATGTTCCGG CGTTATTTCT TGATGTCTCT GACCAGACAC CCATCAACAG TATTATTTTC    1740

TCCCATGAAG ACGGTACGCG ACTGGGCGTG GAGCATCTGG TCGCATTGGG TCACCAGCAA    1800

ATCGCGCTGT TAGCGGGCCC ATTAAGTTCT GTCTCGGCGC GTCTGCGTCT GGCTGGCTGG    1860

CATAAATATC TCACTCGCAA TCAAATTCAG CCGATAGCGG AACGGAAGG CGACTGGAGT     1920

GCCATGTCCG GTTTTCAACA AACCATGCAA ATGCTGAATG AGGGCATCGT TCCCACTGCG    1980

ATGCTGGTTG CCAACGATCA GATGGCGCTG GGCGCAATGC GCGCCATTAC CGAGTCCGGG    2040

CTGCGCGTTG GTGCGGATAT CTCGGTAGTG GGATACGACG ATACCGAAGA CAGCTCATGT    2100

TATATCCCGC CGTTAACCAC CATCAAACAG GATTTTCGCC TGCTGGGCA AACCAGCGTG     2160

GACCGCTTGC TGCAACTCTC TCAGGGCCAG GCGGTGAAGG GCAATCAGCT GTTGCCCGTC    2220

TCACTGGTGA AAAGAAAAAC CACCCTGGCG CCCAATACGC AAACCGCCTC TCCCCGCGCG    2280

TTGGCCGATT CATTAATGCA GCTGGCACGA CAGGTTTCCC GACTGGAAAG CGGGCAGTGA    2340

GCGCAACGCA ATTAATGTAA GTTAGCGCGA ATTGTCGACC AAAGCGGCCA TCGTGCCTCC    2400

CCACTCCTGC AGTTCGGGGG CATGGATGCG CGGATAGCCG CTGCTGGTTT CCTGGATGCC    2460

GACGGATTTG CACTGCCGGT AGAACTCCGC GAGGTCGTCC AGCCTCAGGC AGCAGCTGAA    2520

CCAACTCGCG AGGGGATCGA GCCCGGGGTG GGCGAAGAAC TCCAGCATGA GATCCCCGCG    2580

CTGGAGGATC ATCCAGCCGG CGTCCCGGAA AACGATTCCG AAGCCCAACC TTTCATAGAA    2640

GGCGGCGGTG GAATCGAAAT CTCGTGATGG CAGGTTGGGC GTCGCTTGGT CGGTCATTTC    2700

GAACCCCAGA GTCCCGCTCA GAAGAACTCG TCAAGAAGGC GATAGAAGGC GATGCGCTGC    2760

GAATCGGGAG CGGCGATACC GTAAAGCACG AGGAAGCGGT CAGCCCATTC GCCGCCAAGC    2820

TCTTCAGCAA TATCACGGGT AGCCAACGCT ATGTCCTGAT AGCGGTCCGC CACACCCAGC    2880

CGGCCACAGT CGATGAATCC AGAAAAGCGG CCATTTTCCA CCATGATATT CGGCAAGCAG    2940

GCATCGCCAT GGGTCACGAC GAGATCCTCG CCGTCGGGCA TGCGCGCCTT GAGCCTGGCG    3000

AACAGTTCGG CTGGCGCGAG CCCCTGATGC TCTTCGTCCA GATCATCCTG ATCGACAAGA    3060

CCGGCTTCCA TCCGAGTACG TGCTCGCTCG ATGCGATGTT TCGCTTGGTG GTCGAATGGG    3120

CAGGTAGCCG GATCAAGCGT ATGCAGCCGC CGCATTGCAT CAGCCATGAT GGATACTTTC    3180

TCGGCAGGAG CAAGGTGAGA TGACAGGAGA TCCTGCCCCG GCACTTCGCC CAATAGCAGC    3240

CAGTCCCTTC CCGCTTCAGT GACAACGTCG AGCACAGCTG CGCAAGGAAC GCCCGTCGTG    3300

GCCAGCCACG ATAGCCGCGC TGCCTCGTCC TGCAGTTCAT TCAGGGCACC GGACAGGTCG    3360

GTCTTGACAA AAAGAACCGG GCGCCCCTGC GCTGACAGCC GGAACACGGC GGCATCAGAG    3420

CAGCCGATTG TCTGTTGTGC CCAGTCATAG CCGAATAGCC TCTCCACCCA AGCGGCCGGA    3480

GAACCTGCGT GCAATCCATC TTGTTCAATC ATGCGAAACG ATCCTCATCC TGTCTCTTGA    3540

TCAGATCTTG ATCCCCTGCG CCATCAGATC CTTGGCGGCA AGAAAGCCAT CCAGTTTACT    3600

TTGCAGGGCT TCCCAACCTT ACCAGAGGGC GCCCCAGCTG GCAATTCCGG TTCGCTTGCT    3660

GTCCATAAAA CCGCCCAGTC TAGCTATCGC CATGTAAGCC CACTGCAAGC TACCTGCTTT    3720

CTCTTTGCGC TTGCGTTTTC CCTTGTCCAG ATAGCCCAGT AGCTGACATT CATCCGGGGT    3780

CAGCACCGTT TCTGCGGACT GGCTTTCTAC GTGTTCCGCT TCCTTTAGCA GCCCTTGCGC    3840

CCTGAGTGCT TGCGGCAGCG TGAAGCTTAA AAAACTGCAA AAATAGTTT GACTTGTGAG     3900
```

```
CGGATAACAA TTAAGATGTA CCCAATTGTG AGCGGATAAC AATTTCACAC ATTAAAGAGG      3960

AGAAATTACA TATG                                                        3974

(2) INFORMATION FOR SEQ ID NO: 26:

(i) SEQUENCE CHARACTERISTICS:
         (A) LENGTH: 112 base pairs
         (B) TYPE: nucleic acid
         (C) STRANDEDNESS: both
         (D) TOPOLOGY: both (ii) MOLECULE TYPE: cDNA (xi) SEQUENCE DESCRIPTION: SEQ ID NO: 26:

AAGCTTAAAA AACTGCAAAA AATAGTTTGA CTTGTGAGCG GATAACAATT AAGATGTACC        60

CAATTGTGAG CGGATAACAA TTTCACACAT TAAAGAGGAG AAATTACATA TG              112

(2) INFORMATION FOR SEQ ID NO: 27:

(i) SEQUENCE CHARACTERISTICS:
         (A) LENGTH: 415 base pairs
         (B) TYPE: nucleic acid
         (C) STRANDEDNESS: both
         (D) TOPOLOGY: linear (ii) MOLECULE TYPE: cDNA (xi) SEQUENCE DESCRIPTION: SEQ ID NO: 27:

GCTCGAGCTT TCCACGCAAA TCTCCAATAG CGTTGGTGTG CACACTCTTG CTCCCTGACC       60

TTGGCCCCTT GTGCTTTTCA TAGAGACACC CTGGGGAAGG CAGTTTTTGA TCATAATGGT      120

TGTCACCTGA GCTGGCATTA CCAAAAAGCT GGGCTCCACT GCCCACGCAG TACAGGTATG      180

GGTAGTAAGG ATAGCTGTTA TACACGGAGA CCAGGGAGGC CCGGGAGAAG GCCTCTCTTT      240

CAGGGCCGGC AAAGAGGAGT GCTTCTCCAA GTCTCCCAGC TCCGAGGAGA GCTGCTTTCG      300

CTTAGTCTTA TAGCGTCTGT TCTGGAACCA TATCTTCACT TGGGTCTCCG TGAGCTTGAG      360

GTTCTTGGCC AGGTGGGCCG TTCAGGGCGA TCAGGTACTT CTGATGGCTG AACTT           415

(2) INFORMATION FOR SEQ ID NO: 28:

(i) SEQUENCE CHARACTERISTICS:
         (A) LENGTH: 507 base pairs
         (B) TYPE: nucleic acid
         (C) STRANDEDNESS: both
         (D) TOPOLOGY: linear (ii) MOLECULE TYPE: cDNA (xi) SEQUENCE DESCRIPTION: SEQ ID NO: 28:

TTTTTTTCCC GTCCGACCCT CCGGAGTTTA TTCACTTCCA GCGGTACTGG GCTGGACCGA       60

GCCTTGGTGG CATCCGATTC AGCTCCAGCA GCATCCCAGG TCCTATCCAG CATGGGCGGG     120

GCACCGCTGG TCAGAGCTCT GGCCTTCAGG AATCTTCGGA CTCGTCCCTT TCCTCGAAGT     180

CGGGCTCGGG CTCTGGGTCC GGTTCTGGCT CCAGTTCCGG CTCTGGTTCT GCTTCAGCCT     240

CGGGTTCCAG CTCTGGCTCT GGCTCCGGCT CCGGTTCAGC CTCTTTAGAG GCCTCAGCTT     300

CCAGCTCTGG CTCTGGCTCC TCCGGGGTCC GGATTGCAC CGCCTCGGAG CGCTCAGGCC     360

CTCCGGCTAC GTCAGGGTCT GAAGCTCTGG GCAACCCGGG GCATGTGGTC ACCGAGCCGG    420

GTGCCTCCGG GTCCAGTGGC CTGGGCATGG AGGGTCATAG CTGCGGTCGC GGTAGCCCGG    480

ACCCACGTAC TGCGAGTCGA AAGCGGG                                        507
```

(2) INFORMATION FOR SEQ ID NO: 29:

(i) SEQUENCE CHARACTERISTICS:
        (A) LENGTH: 533 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 29:

```
NGCACAGCAG NNAGGCACTT GGAGGTCTTA TCTGTTNGAC TTGNTNAACA CTTCAGGCGC      60

CCTTCCAAGG CTTCCCCAAA CCCCTAAGCA GCCGCANAAG CGCTCCCGAG CTGCCTTCTC     120

CCACACTCAG GTGATCGAGT TGGAGAGGAA GTTCAGCCAT CAGAAGTACC TGTCGGCCCC     180

TGGAACGGGC CCACCTGGCC AAGAACCTCA AGCTCACGGA GACCCAAGTG AAGATATGGT     240

TCCAGAACAG ACGCTATAAG ACTAAGCGAA ACAGCTCTCC TCGGANCTGG GGAGACTTGG     300

AGAAGCACTC CTCTTTGNCC GGCCCTGAAN GAGGAGGCCN TCNCCCGGGC CNNCCTGGTC     360

NCCGTGTAAT AACAGCGANC CTTNANTACC CATACNTGTA ANGCNTGGGG CANNGGGAAG     420

CCCAGTTTNT TGGTAAANGG CCAGCTCCAG GTGAACAACC ATTAAGGATC AAAANGGCCT     480

TNCCCCAGGG TGTTNCATGG AAAAGCACAA GGGGCAAGGT CAGGAGCAAA AGN           533
```

(2) INFORMATION FOR SEQ ID NO: 30:

(i) SEQUENCE CHARACTERISTICS:
        (A) LENGTH: 318 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 30:

```
GGGAGCTGGA GCCAGAGCCA GAGCCAGATC TCAGGAAACT GGGGTCATTG CATAGAGGCT      60

GCCAGACAGT CTGCAGAGCT CAGCGGCCTG GGTTCAAACC TTCTCGCACA CTGCCACTGT     120

CGGTTACTTT GGCTTTCTAG AGCCAGATTC CTTGGCCATG AAATGGGTAC TGCTTACTTC     180

CCAGGTTATT TGAGAATGA AGTGAGATGA AGTCAACAGT AGATGTATCT GTCCGTTGTC     240

CCTGCCCTGC TGTGGGGATG ACAGAGTGAT TTTGGACAAG ACCCAAGGNC TCGCTGGGCA     300

TCACTGGTCT TTCTTCAG                                                   318
```